(12) United States Patent
Liu et al.

(10) Patent No.: US 6,990,715 B2
(45) Date of Patent: Jan. 31, 2006

(54) FLEXIBLE MANUFACTURING SYSTEM

(75) Inventors: Vincent Bardina Liu, Cincinnati, OH (US); Donald Louis Wires, Loveland, OH (US); Michael Joseph Lamping, Cincinnati, OH (US); Albert Michael Fischer, Fairfield, OH (US); Gary Lee Miller, Fairfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 499 days.

(21) Appl. No.: 10/203,038

(22) PCT Filed: Jan. 31, 2001

(86) PCT No.: PCT/US01/03188

§ 371 (c)(1),
(2), (4) Date: Aug. 5, 2002

(87) PCT Pub. No.: WO01/56523

PCT Pub. Date: Aug. 9, 2001

(65) Prior Publication Data

US 2003/0004594 A1    Jan. 2, 2003

Related U.S. Application Data

(60) Provisional application No. 60/179,895, filed on Feb. 2, 2000.

(51) Int. Cl.
    *B23P 19/00*    (2006.01)
(52) U.S. Cl. .......................... 29/428; 29/430; 29/783; 29/791; 156/538; 156/349; 700/95; 700/117

(58) Field of Classification Search .................. 29/428, 29/430, 561, 564, 705, 709, 711, 783, 791; 156/538, 349, 539, 543, 552, 343; 700/95, 700/117

See application file for complete search history.

(56) References Cited

U.S. PATENT DOCUMENTS

| | | |
|---|---|---|
| 3,860,003 A | 1/1975 | Buell |
| 4,218,815 A | 8/1980 | Cumming |
| 4,342,314 A | 8/1982 | Radel et al. |
| 4,381,781 A | 5/1983 | Sciaraffa et al. |
| 4,463,045 A | 7/1984 | Ahr et al. |
| 4,472,783 A | 9/1984 | Johnstone et al. |
| 4,492,297 A | 1/1985 | Sticht |

(Continued)

FOREIGN PATENT DOCUMENTS

EP          0267861 A2        5/1988

(Continued)

*Primary Examiner*—David P. Bryant
*Assistant Examiner*—Jermie E. Cozart
(74) *Attorney, Agent, or Firm*—Michael P. Hayden; Jack L. Oney; Michael S. Kolodesh

(57) ABSTRACT

A flexible manufacturing system having a feature section including at least one module, at least one operational unit mounted to the module and a local controller operatively connected to the operational unit. The local controller is adapted to receive a reference signal and to control the operation of the operational unit based upon the reference signal.

4 Claims, 47 Drawing Sheets

U.S. PATENT DOCUMENTS

| | | |
|---|---|---|
| 4,789,039 A | 12/1988 | Bjork |
| 4,807,420 A | 2/1989 | Barker |
| 4,857,067 A | 8/1989 | Wood et al. |
| 4,938,753 A | 7/1990 | Van Gompel et al. |
| 5,062,195 A | 11/1991 | Binder |
| 5,083,364 A | 1/1992 | Olbrich et al. |
| 5,151,092 A | 9/1992 | Buell et al. |
| 5,155,679 A | 10/1992 | Jain et al. |
| 5,212,645 A | 5/1993 | Wildes et al. |
| 5,221,274 A | 6/1993 | Buell et al. |
| 5,235,515 A * | 8/1993 | Ungpiyakul et al. ........ 700/125 |
| 5,353,490 A | 10/1994 | Kukuljan |
| 5,361,486 A | 11/1994 | Harmsen et al. |
| 5,383,988 A | 1/1995 | Herrmann et al. |
| 5,460,623 A | 10/1995 | Emenaker et al. |
| 5,492,591 A | 2/1996 | Herrmann et al. |
| 5,518,801 A | 5/1996 | Chappell et al. |
| 5,539,975 A | 7/1996 | Kukuljan et al. |
| 5,554,145 A | 9/1996 | Roe et al. |
| 5,569,234 A | 10/1996 | Buell et al. |
| 5,580,411 A | 12/1996 | Nease et al. |
| 5,615,468 A | 4/1997 | Chubbuck |
| 5,657,529 A | 8/1997 | Bohn et al. |
| 5,669,897 A | 9/1997 | Lavon et al. |
| 5,868,899 A * | 2/1999 | Gundersen .................. 156/538 |
| 5,914,880 A | 6/1999 | Yasojima et al. |
| 6,004,306 A | 12/1999 | Robles et al. |
| 6,185,469 B1 | 2/2001 | Lewis et al. |
| 6,273,165 B1 | 8/2001 | Gundersen et al. |
| 6,349,237 B1 | 2/2002 | Koren et al. |

FOREIGN PATENT DOCUMENTS

| | | |
|---|---|---|
| EP | 0 589 859 A1 | 3/1994 |
| WO | WO 95/13775 | 5/1995 |
| WO | WO 95/32695 A1 | 12/1995 |

* cited by examiner

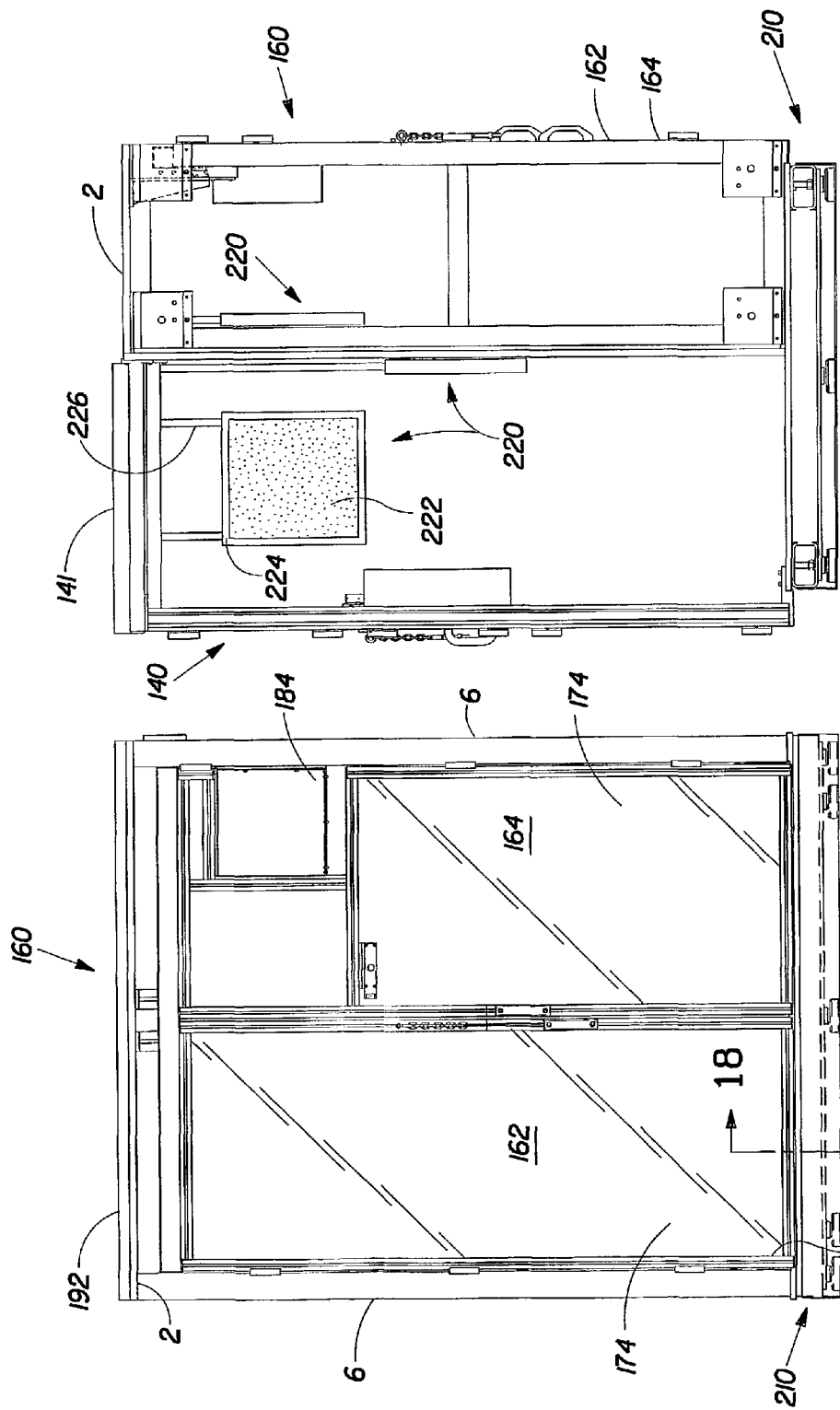

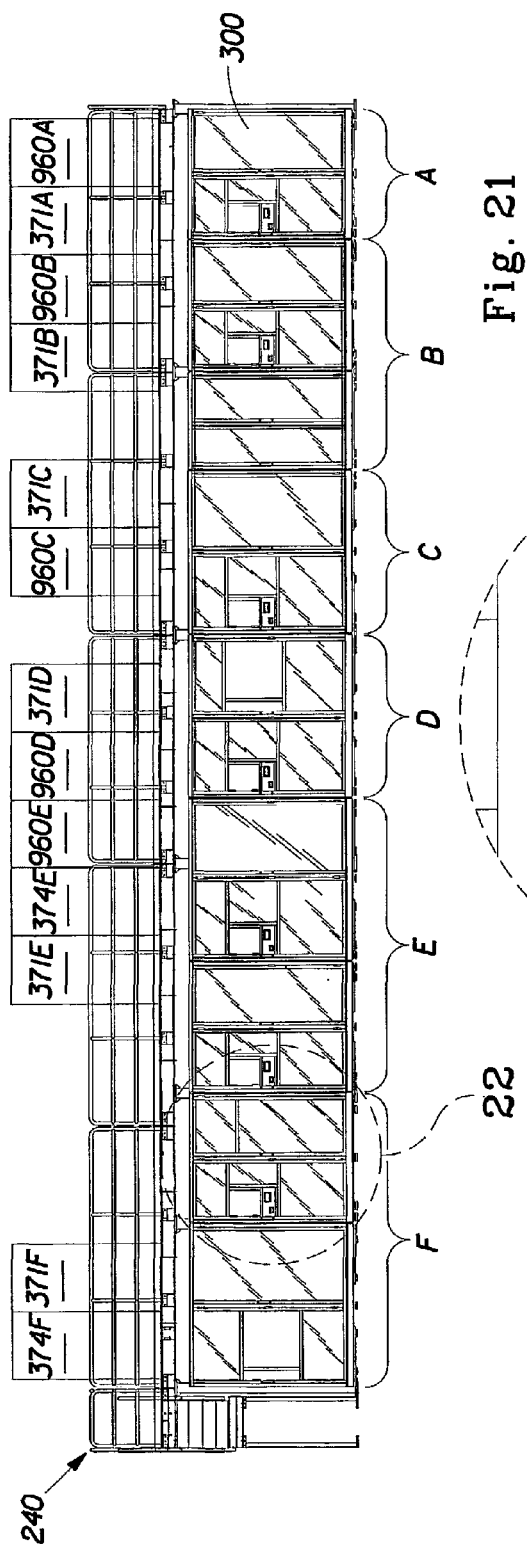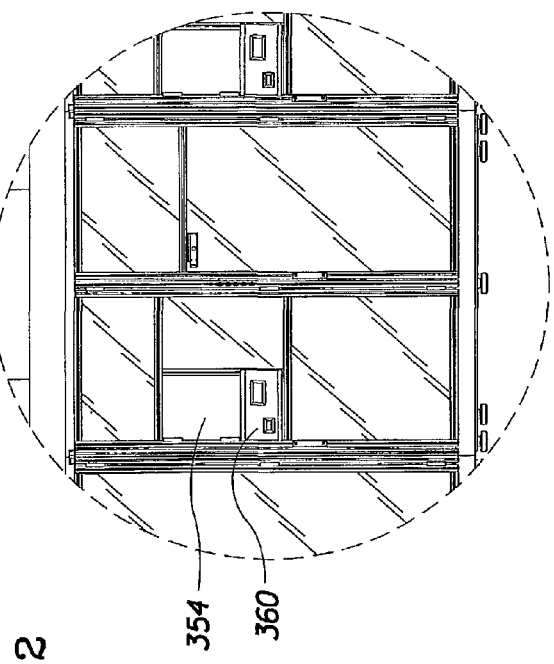
Fig. 21
Fig. 22

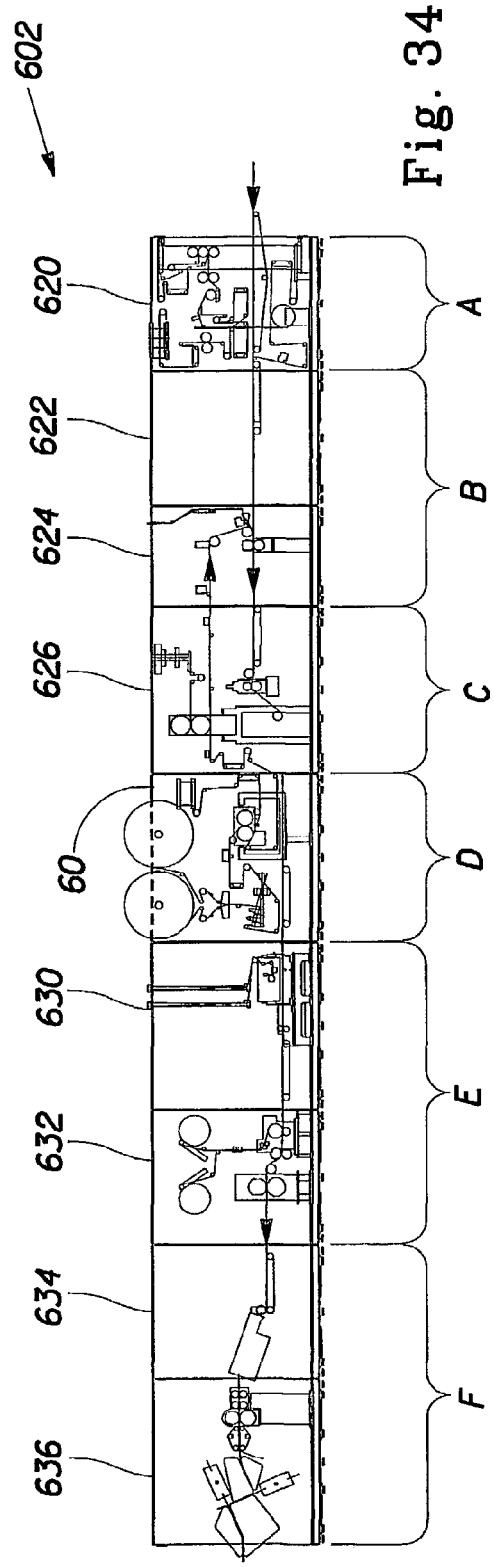
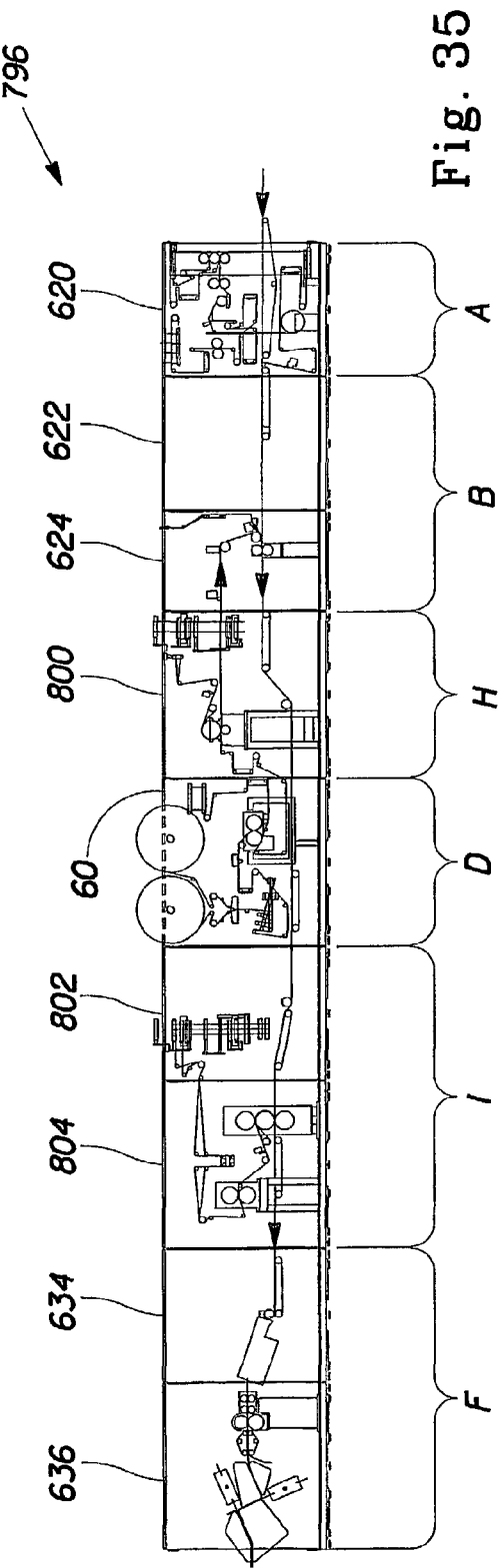

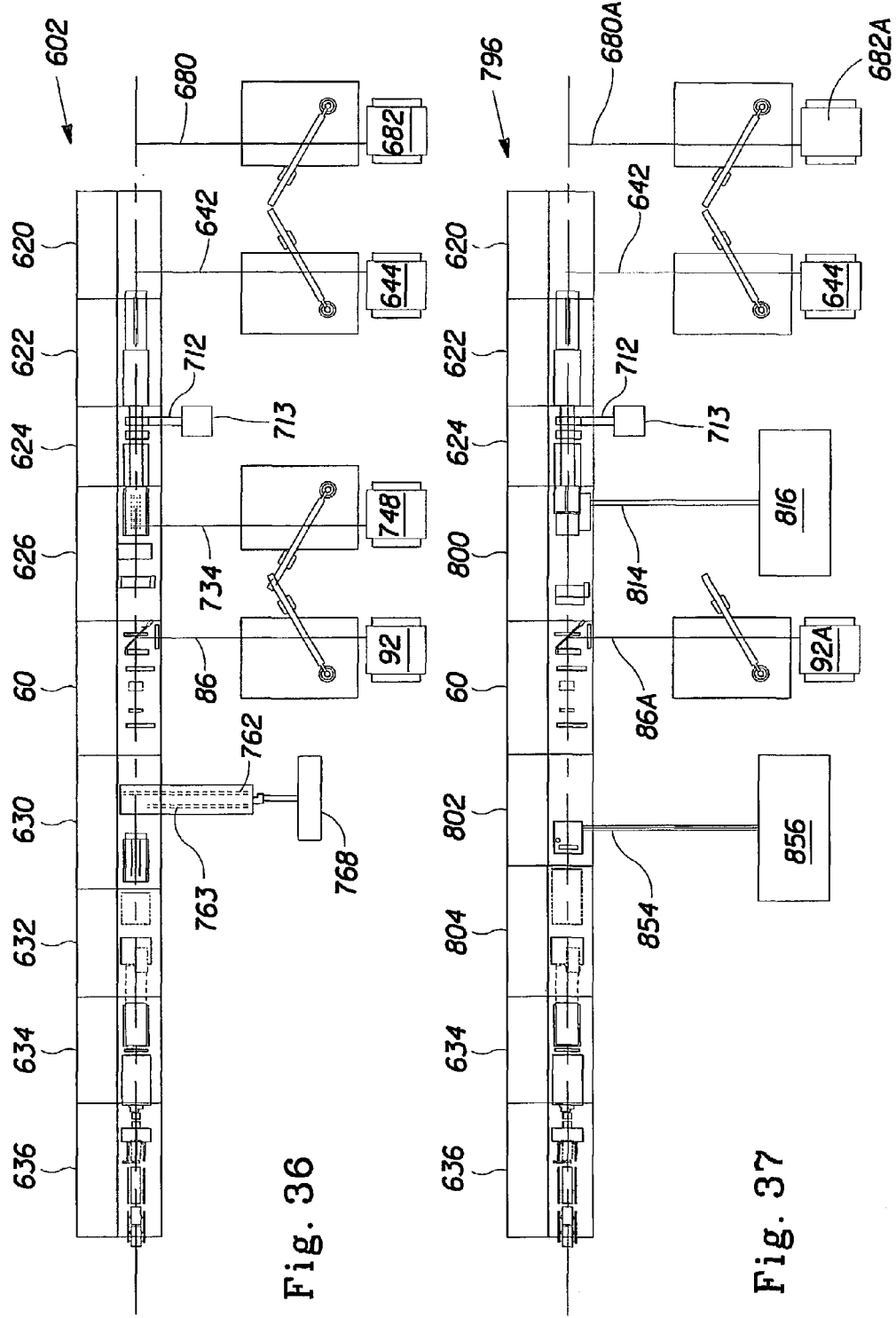

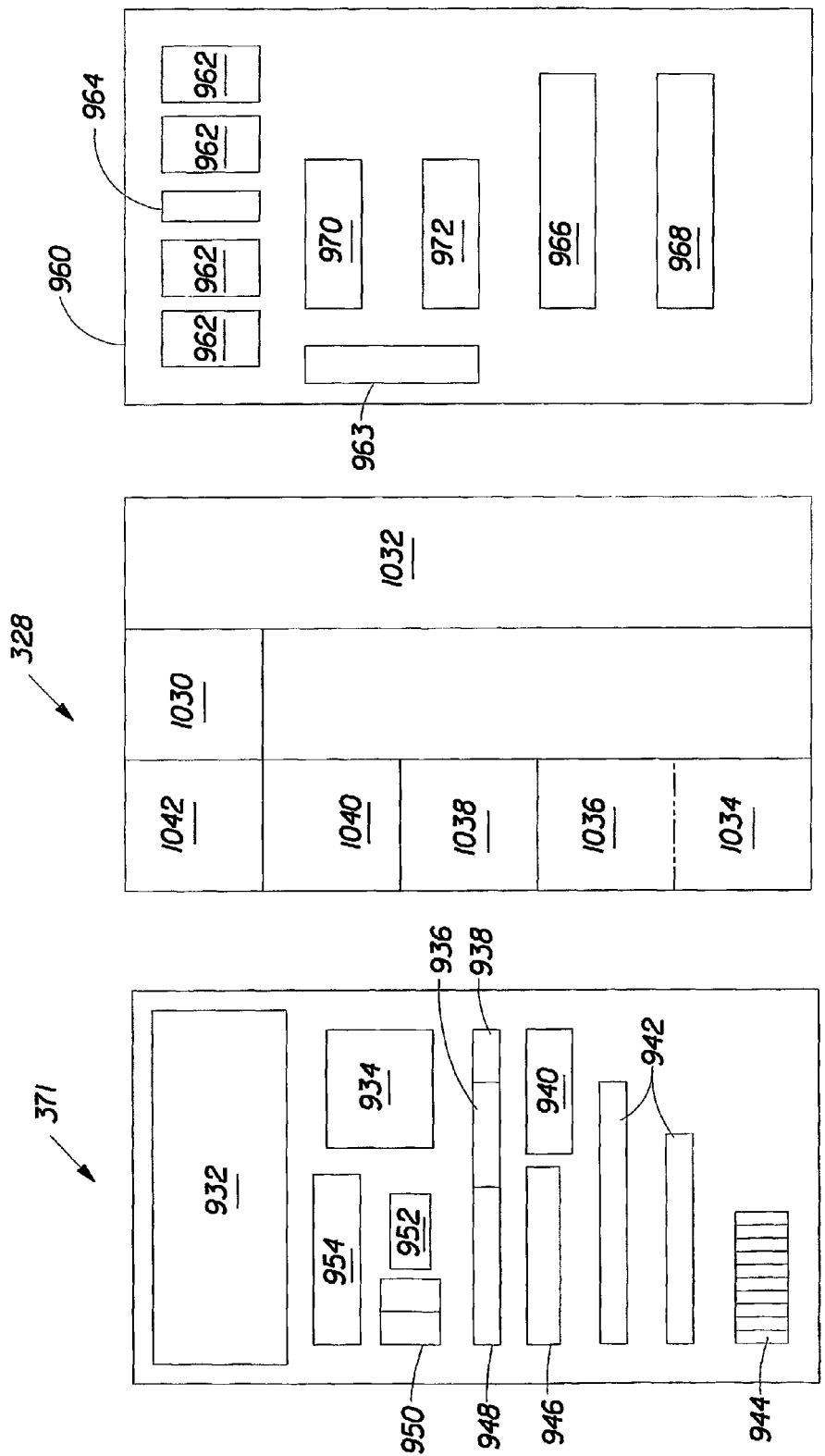

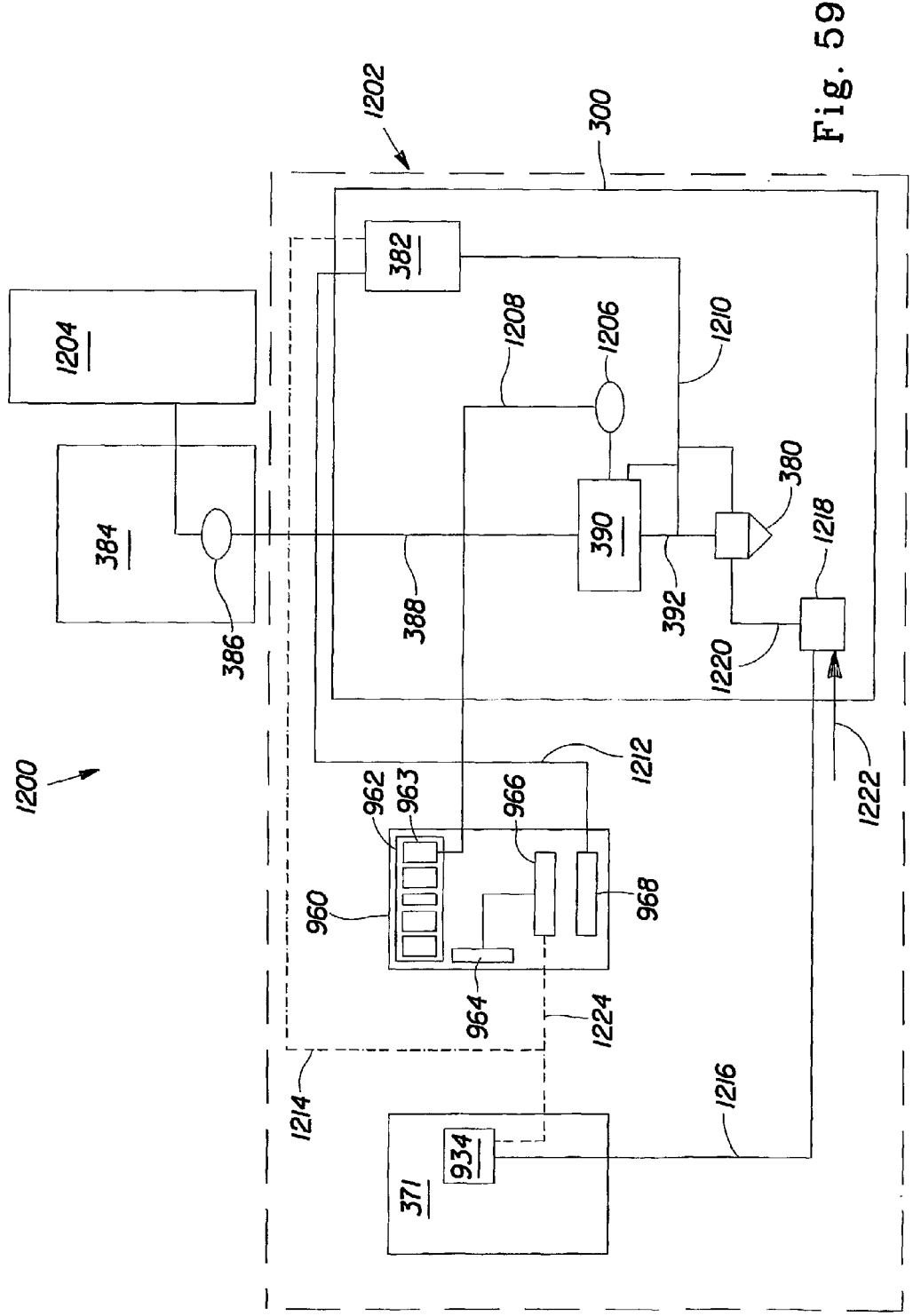

FLEXIBLE MANUFACTURING SYSTEM

FILING REFERENCE

This Application claims priority under Title 35, United States Code 119(e) from Provisional Application Ser. No. 60/179,895, filed Feb. 2, 2000.

FIELD OF THE INVENTION

This invention relates to a flexible manufacturing system. More particularly, this invention relates to a flexible manufacturing system that allows for efficient product development and line changes to accommodate changes in product design.

BACKGROUND OF THE INVENTION

Disposable and durable products such as diapers, adult incontinence articles, feminine hygiene tampons, sanitary napkins, bandages, underpants, shirts, shorts, swimsuits, gowns, pants, coats, gloves, scarves, surgical drapes, bibs, blankets, sheets, pillow cases, mops, etc. may be manufactured on high speed converting lines. A converting line utilizes a web-based carrier to which many source materials, whether in a continuous web or discrete pieces, are processed and/or attached to the web to create a finished product.

Although a converting line may allow for high speed production, typical converting lines are inflexible in that line changes are time consuming and expensive. Product development and implementation of product upgrades usually require extensive testing and construction efforts. A product upgrade may, for example, require the following steps: constructing manual or handmade products incorporating the upgrade in order to test the concept and determine consumer acceptance of such an upgrade; constructing a machine production unit that may manufacture the product upgrade and/or the entire product incorporating the upgrade in order to determine product and process feasibility; constructing a high speed test stand that may manufacture the product upgrade in isolation at high speeds in order to test the feasibility of high speed manufacturing; constructing a prototype line that is able to make complete prototype products at high speeds; reconstructing a high speed production line to implement the process changes necessary for the product upgrade; and testing and debugging the production line. These efforts may be expensive and time consuming, especially when the reconstruction, testing and debugging steps lead to down time of a high speed production line. Then, when a product upgrade is rolled out on multiple production lines, the time and money required to implement even a small change in each individual line may increase dramatically. Often, the time and money required will be prohibitive, and highly desirable product upgrades may be delayed or even eliminated.

Attempts to increase the flexibility of a converting line have been made. U.S. Pat. No. 5,383,988 entitled "Modular Apparatus for Fabricating an Absorbent Article," issued to Thomas R. Herrmann et al. on Jan. 24, 1995 and U.S. Pat. No. 5,492,591 entitled "Modular Apparatus for Fabricating an Absorbent Article," issued to Thomas R. Herrmann et al. on Feb. 20, 1996, for example, describe a system for fabricating absorbent articles that includes a linear array of substantially identical frame modules joined together. A plurality of substantially identical, removable panels that support working devices are mounted to one face of the modules. The Herrmann references describe that mounting the working devices to the removable panels facilitates rapid installation, servicing, adjustment of the working devices and accommodates convenient observation of the operation of such devices.

Another attempt to increase the flexibility of a converting line is disclosed in U.S. Pat. No. 5,868,899 entitled "Process Line for the Production of Absorbent Disposable Products," issued to Dag H. Gundersen on Feb. 9, 1999, which describes a converting line for manufacturing disposable absorbent articles in which removable rectangular carrier plates that carry working devices are attached to vertical and horizontal posts. The posts are arranged sequentially in a framework on the same side of and parallel to a conveyor path movement. The Gundersen reference describes that the working devices in the converting line may be removed from, replaced or inserted into the converting line by removing, replacing or inserting the carrier plate to or from the framework of vertical and horizontal posts.

Although these efforts may allow for quicker physical construction or reconstruction of a converting line once the process for manufacturing a newly developed product has been developed off-line, the steps of constructing a machine production unit that may manufacture the product upgrade and/or the entire product incorporating the upgrade in order to determine product and process feasibility; constructing a high speed test stand that may manufacture the product upgrade in isolation at high speeds in order to test the feasibility of high speed manufacturing; and constructing a prototype line that is able to make complete prototype products at high speeds are still required. Also, the lines disclosed in the Herrmann and Gundersen references, once constructed, still require significant testing and debugging time before the line may be used for production of products. Thus, a method allowing for quicker product and process development is desired. Minimizing down time due to testing and debugging a production converting line after construction or reconstruction is also desirable.

Further, a typical product upgrade may be product-focused and includes changing one or more particular product features. In a disposable diaper, for example, a product upgrade may include making a multiple-layer back ear extensible. On a typical diaper converting line, each layer that ultimately forms part of the back ear may be introduced into the line, processed at various points along the line, combined together and attached to a carrier web. Various other operations that form other parts of the finished disposable diaper may be physically interspersed with these operations. Thus, the operations that produce a particular feature of the disposable diaper such as a multiple-layer back ear are located at various locations throughout the converting line. A product upgrade that makes the back ear extensible, for example, may involve changes to multiple operations that are spread throughout the converting line.

In addition, the control programming that controls each operation for producing the particular feature of the disposable product may be dispersed throughout the code for the entire converting line. Changing the control code for the particular upgrade may often include making changes in many different sections of the code that control particular operations that form the particular product feature being altered. Changes to multiple operations interspersed between operations not related to the product upgrade may also require changes to the control programming that handles any synchronization between each of these operations.

Changing out particular operations in different physical locations throughout the line as well as tracking down and changing code sections that control those operations in a program that controls the entire converting line may be time consuming, may result in inefficient problem-solving and may result in expensive down time of a high-speed production line. In contrast, however, bringing the physical operations that form a particular feature together and/or bringing the software code sections together that control the formation of the particular product feature together may result in efficiencies that cut both development time and change-over time for developing and implementing a product upgrade. These efficiencies may result in faster innovation, and quicker, more frequent and less expensive product upgrades.

SUMMARY OF THE INVENTION

The present invention comprises a flexible manufacturing system having a control system and a physical arrangement that allows for efficient line changes to accommodate changes in product design. The flexible manufacturing system includes at least one "feature section." Each feature section may include all or substantially all of the operational units that needed to fabricate a particular product feature. Each of the operational units of the feature section may be physically co-located in one portion of the converting line. The feature section may also have at least one distinct control routine that commonly controls the operation of substantially each operational unit in the feature section.

In one embodiment of the present invention, the feature section may comprise one or more modules that include all or substantially all of the operational units for that feature section. In a further embodiment, the modules may be standard modules that may be configured to support different types of operational units. The operational units of a feature section may be grouped together in one or more modules that may be located together in the converting line and may be commonly controlled.

One or more modules may be run off-line in a standalone operation, such as for a test stand, including the one or more modules and one or more local controllers that may be tested, adjusted or modified to perform product development work. In a particular embodiment, the one or more modules may comprise one or more feature sections that each has its own feature local controller. The one or more feature sections may be run off-line so that all or a portion of the operational units that comprise the feature section may be tested, adjusted or modified until a suitable process for forming a new product feature has been developed. Once a process for forming a product upgrade has been developed off-line, the module or modules that comprise a newly developed feature section may be inserted into a converting line or one or more modules already in the converting line may be replaced with the module or modules that comprise the newly developed feature section.

In an alternative embodiment, the feature section may comprise a portion of a conventional converting line or a converting line such as the ones described in the Herrmann and Gundersen references. In either case, all or substantially all of the operational units for that feature section are preferably commonly controlled and physically co-located in one region of the converting line. In this embodiment, a test stand including substantially each of the operational units that make up the feature section may be developed so that not only the operation of each particular operational unit or only a few operational units may be analyzed, adjusted and modified, but the interactions between each of the operational units for the particular feature section may be analyzed, adjusted and modified. In this way, a complete prototype of the product feature may be assembled on the test stand.

The flexible manufacturing system of the present invention also includes a method of synchronizing the operation of the feature section with the rest of the converting line. In one embodiment, the flexible manufacturing system may also include a central computer or a local controller that synchronizes the operation of the feature section with the rest of the converting line.

BRIEF DESCRIPTION OF THE DRAWINGS

While the specification concludes with claims particularly pointing out and distinctly claiming the subject matter which is regarded as the present invention, it is believed that the invention will be better understood from the following drawings, in which:

FIG. 15 is a rear view from the drive side of a module frame of an embodiment of an enclosure for a sound suppression system enclosing the drive side of the module frame.

FIG. 16 is a side view of the module with enclosures shown in FIGS. 13 and 15.

FIG. 21 is a simplified view front from the operator side of a modular converting line of a flexible manufacturing system of the present invention including a cabinet support structure.

FIG. 22 is an enlarged front view of a module shown in FIG. 21.

FIG. 34 is a simplified front view from the operator side of a modular converting operation which in conjunction with the core making operation shown in FIG. 33 could be used to manufacture the diaper shown in FIG. 30.

FIG. 35 is a modified modular converting operation shown in FIG. 34 which in conjunction with the core making operation shown in FIG. 33 could be used to manufacture the diaper shown in FIG. 31.

FIG. 36 is a simplified top view of the modular converting operation shown in FIG. 34.

FIG. 37 is a simplified top view of the modular converting operation shown in FIG. 35.

FIG. 56 is an example of one embodiment of a standard main control panel.

FIG. 57 is an example of one embodiment of a power distribution center.

FIG. 58 is an example of one embodiment of a standard adhesive panel.

FIG. 59 is a block diagram of an adhesive control system.

DETAILED DESCRIPTION OF THE INVENTION

The present invention is directed to a flexible manufacturing system for manufacturing disposable, reusable and durable products. This application contains non-limiting examples of particular disposable absorbent articles. The manufacturing principles of the present invention, however, may be reapplied by one skilled in the art to manufacturing systems for the manufacture of many other types of disposable, reusable and durable products. Other embodiments of a flexible manufacturing system of the present invention are also disclosed in copending U.S. application Ser. No. 09/496,480 (P&G Case No. 7939) entitled "Flexible Manufacturing System" filed on Feb. 2, 2000 by Vincent B. Lie et al, which is incorporated by reference in this application. As used herein, the term "absorbent article" refers to devices which absorb and contain body exudates, and more specifically, refers to devices that are placed against or in proximity to the body of the wearer to absorb and contain the various exudates discharged from the body. The term "disposable" is used to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) One product that may be manufactured by a flexible manufacturing system of the present invention is the disposable absorbent article, diaper 500, shown in FIG. 30. As used herein, the term "diaper" refers to an absorbent article generally worn by infants and incontinent persons about the lower torso.

Figure 30:
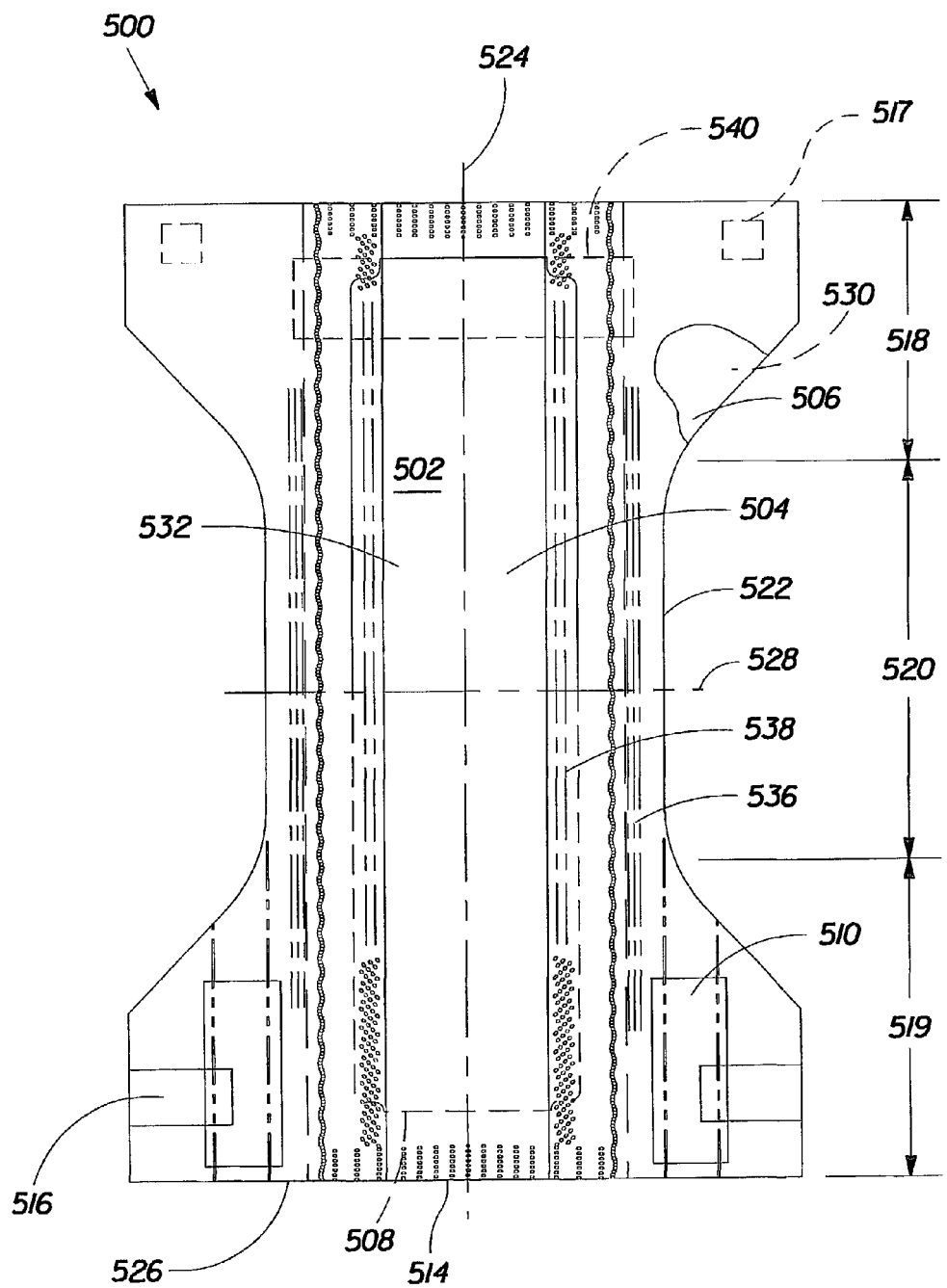
FIG. 30 is a plan view of a disposable diaper which could be manufactured using the present invention, the diaper having portions cut away to reveal the underlying structure of the diaper.

FIG. 30 is a plan view of a unibody diaper 500, which may be manufactured by a flexible manufacturing system of the present invention, in a flat-out state with portions of the structure being cut-away to more clearly show the construction of the diaper 500. The portion of the diaper 500 which faces the wearer is oriented towards the viewer. As shown in FIG. 30, the diaper 500 preferably comprises a liquid pervious topsheet 504; a liquid impervious backsheet 506; an absorbent core 508, which is preferably positioned between at least a portion of the topsheet 504 and the backsheet 506; side panels 510; gasketing leg cuffs 536; barrier leg cuffs 538; an elastic waist 514; a primary fastening system generally designated as 516; and a secondary fastener 517. Diaper 500 is shown in FIG. 30 to have a first waist region 518, a second waist region 519 opposed to the first waist region 518 and a crotch region 520 located between the first waist region 518 and the second waist region 519. The periphery of the diaper 500 is defined by the outer edges of the diaper 500 in which the longitudinal edges 522 run generally parallel to a longitudinal centerline 524 of the diaper 500 and the end edges 526 run between the longitudinal edges 522 generally parallel to a lateral centerline 528 of the diaper 500.

A chassis 502 of the diaper 500 comprises the main body of the diaper 500. The chassis 502 comprises at least a portion of the absorbent core 508 and preferably an outer covering layer including the topsheet 504 and the backsheet 506. While the topsheet 504, the backsheet 506, and the absorbent core 508 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The diaper 500 may also comprise side panels 510. The side panels 510 may be elastic or extensible to provide a more comfortable and contouring fit by initially conformably fitting the diaper 500 to the wearer and sustaining this fit throughout the time of wear well past when the diaper 500 has been loaded with exudates since the elasticized side panels 510 allow the sides of the diaper 500 to expand and contract. The side panels 510 may also provide more effective application of the diaper 500 because even if the diaperer pulls one elasticized side panel 510 farther than the other during application, the diaper 500 will "self-adjust" during wear.

Figure 31:
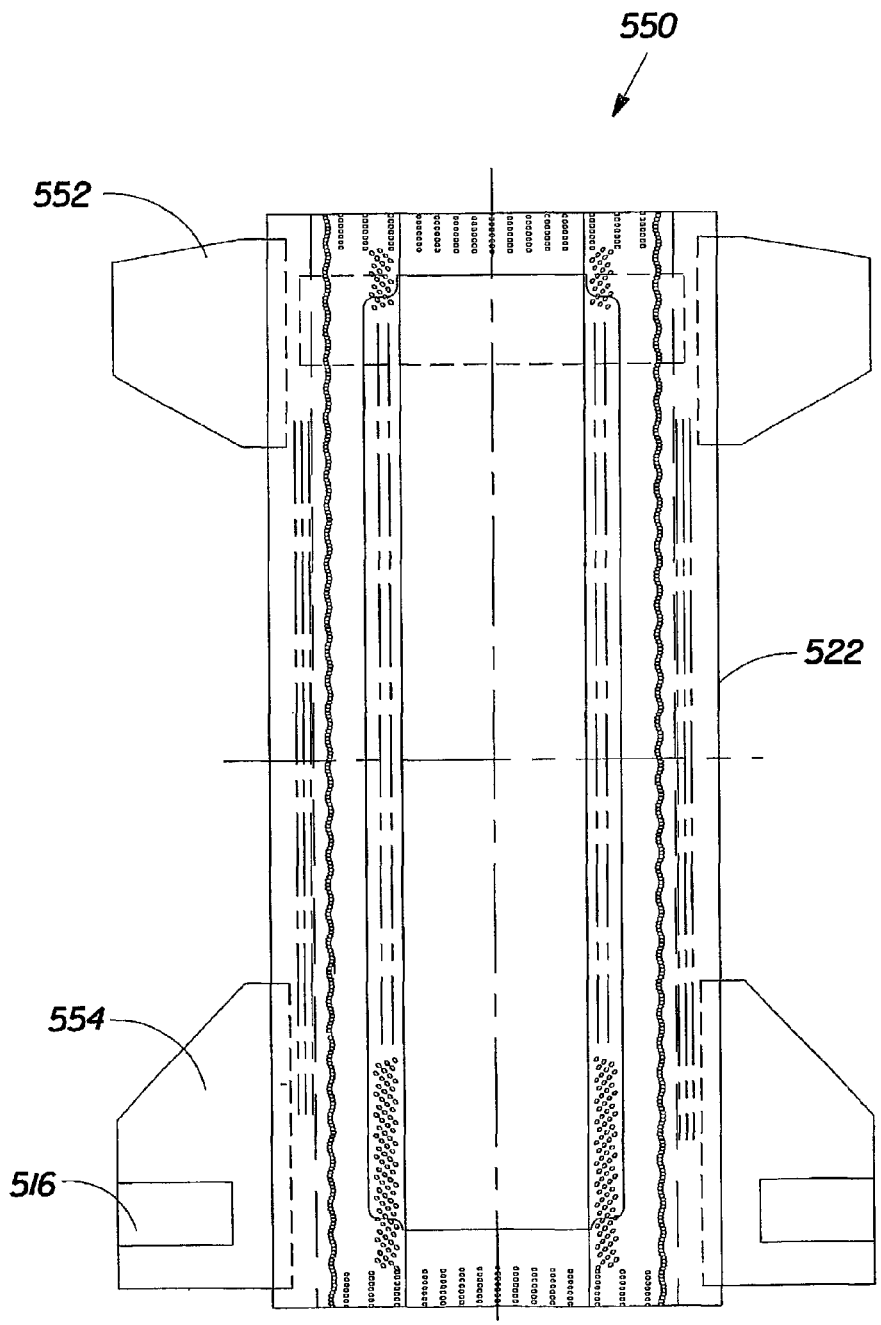
FIG. 31 is a plan view of an alternative design disposable diaper which could be manufactured using the present invention.

An example of a multi-piece disposable diaper 550 is shown in FIG. 31. The diaper 550 includes new features such as front ears 552 and back ears 554. The front ears 552 may be constructed from any single or more than one stock materials and may be joined to the chassis 502 by any means known in the art, including, but not limited to those means recited above. The back ears 554 may be elastic or extensible to provide a more comfortable and contouring fit. The back ears 554 may be constructed in various configurations. Examples of diapers with elasticized ears (or also known as side panels) are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

Figure 32:
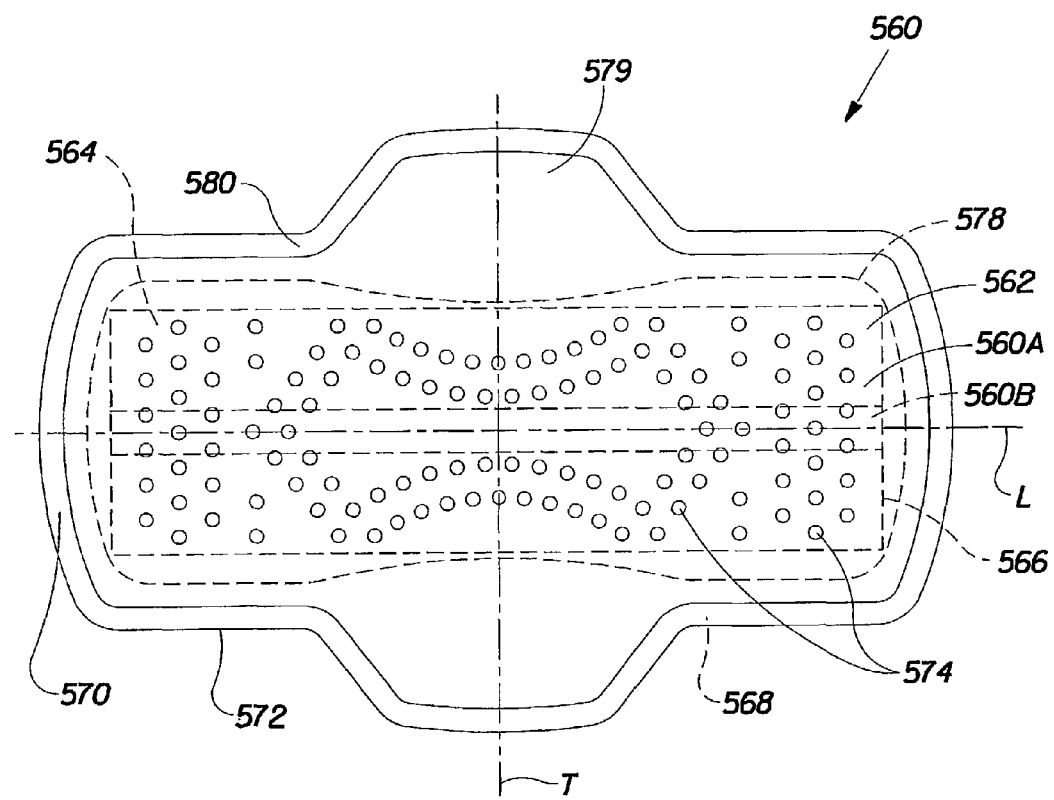
FIG. 32 is a plan view of a disposable feminine protection product which could be manufactured using the present invention.

FIG. 32 shows a plan view of a sanitary napkin 560, that may be manufactured using the present invention. The sanitary napkin 560 has two surfaces, a liquid pervious body-contacting surface or "body surface" 560A and a liquid impervious garment surface 560B. The sanitary napkin 560 is shown in FIG. 32 as viewed from its body surface 560A. The sanitary napkin 560 basically comprises a liquid pervious topsheet 562, a liquid impervious backsheet 564, and an absorbent core 566 positioned between the topsheet 562 and the backsheet 564.

Suitable materials for the various components of the sanitary napkin 560 shown in FIG. 32 are described in greater detail in U.S. Pat. No. 5,460,623 issued to Emenaker, et al. and in the patent publications which are incorporated by reference herein. Preferably, the materials comprising at least the topsheet and backsheet are thermoplastic. In a particularly preferred embodiment, the topsheet 562 comprises the apertured thermoplastic film sold on sanitary napkins by The Procter & Gamble Company of Cincinnati, Ohio, under the trademark DRI-WEAVE, which is manufactured under U.S. Pat. No. 4,342,314 issued to Radel, et al. on Aug. 3, 1982, and U.S. Pat. No. 4,463,045 issued to Ahr, et al. on Jul. 31, 1984. In one particularly preferred embodiment, the absorbent core 566 comprises the absorbent core described in U.S. Pat. No. 5,460,623 issued to Emenaker, et al. The absorbent core 566 preferably comprises absorbent gelling material particles. The backsheet 564 preferably comprises a polyethylene film. Preferably, the sanitary napkin 560 further comprises an optional secondary topsheet 578 positioned between the topsheet 562 and the absorbent core 566.

The term "source material," as used in this application, includes any material supplied to the production machine regardless of the form in which it is supplied, e.g., a single layer or a multiple-layer laminate; a continuous web or discrete pieces; in a roll or in a box, etc., for the purpose of fabricating a disposable article or part of a disposable article. An "element" of a disposable article includes a manipulation of the web or of a discrete disposable article that alters the shape and/or configuration of the web or the discrete article. A "component" of a disposable article, however, refers to a web or a discrete piece that is combined with other components to form a disposable article. An element, for example, may include cutting a continuous web into discrete disposable articles, folding a discrete disposable article into a bi-fold or a tri-fold configuration, etc. A component, however, may include a fastening tape, a landing zone, a topsheet, a backsheet, an absorbent core, an acquisition component, an elastic strand, etc.

A "product feature" is an element or a component of a finished disposable article. A product feature of a diaper such as the one described above may include, for example, an absorbent core 508, a side panel 510, a gasketing leg cuff 536, a barrier leg cuff 538, an elastic waist 514, a back ear 554 or a front ear 552. In a sanitary napkin, for example, a product feature may include an absorbent core 566 or a flap 579. In a pair of shorts, for example, a product feature may include a waist feature, a pocket feature, a button or zipper fly feature, a cuff feature, a hem feature, a pleat feature, etc. In a sheet, a feature may include an elastic corner feature, a hem feature, etc. These examples are meant as merely illustrative and non-limiting examples of product features that may be manufactured in a flexible manufacturing system of the present invention.

A flexible manufacturing system of the present invention may include a hierarchy of groupings such as transformations, corrective measures, transportations, operational units, functional operations and feature sections. In this hierarchy, a "transformation" includes a single, lasting and definite change in a source material, a product, an element or a component of a disposable article. A transformation may include, for example, nipping, ring-rolling, stretching, combining, embossing, applying, etc. A "corrective measure" includes performing a function on the web, a raw material or a component that is temporary or is later changed. A corrective measure may, for example, include heating a web that is later cooled, either through a direct cooling operation performed upon the web, e.g., a water bath or a stream of cool air, or indirectly cooled, e.g., contact with ambient air. A "transportation" may include transporting or positioning a web, a product, an element or a component of a disposable article on a manufacturing line. A transportation may include, for example, drawing or guiding a web, registering a component, etc.

An "operational unit" includes one or more pieces of equipment that perform a single transformation on, a single corrective measure on, or a single transportation of a source material, a web, a product, an element or a component of a disposable article. A operational unit, for example, may include a pair of nip rolls, an adhesive applicator, an omega roll, an initial knife, a conveyor, etc. A "functional operation" includes multiple operational units that transform a source material, a web, a product, an element or a component of a disposable article to perform a particular function. A bonding unit that includes a glue applicator (operational unit 1) and a pair of nip rolls (operational unit 2) that receive a raw material web (source material 1) and transform the raw material web by bonding it to another web (source material 2), for example, performs a bonding function and comprises a functional operation.

A "feature section" includes one or more operational units and/or one or more functional operations that together completely form or assemble a particular product feature. A feature section may include each of the operational units and/or functional operations to form a particular product feature such as, for example, an absorbent core feature 508, a cuff feature 538, a front ear feature 552, a back ear feature 554, a side panel feature 510, an elastic waist feature 514, a fastening feature 516, a fold and form feature, etc. A back ear feature section I shown in FIG. 35 that produces a back ear feature 554 such as shown in FIG. 31, for example, may include a roller system (functional operation 1) that provides a raw material web from a roll to a position parallel to a main web, a cut and slip unit (functional operation 2) that cuts the raw material web into discrete back ear components and places the back ear components on a web in the right location and a bonding unit (functional operation 3) that bonds the ear to the web. A landing zone feature section 60 such as shown in FIGS. 7–10 and 34–37 may include an roller system (functional operation 1) that provides a landing zone raw material web from a roll, a metering system for guiding the landing zone and the backsheet webs (functional operations 2 and 3), a cut and slip unit (functional operation 4) that cuts the landing zone raw material web into discrete landing zone components and places these discrete components on the backsheet, and a bonding unit (functional operation 5) that attaches the discrete landing zone component to the backsheet.

A single functional operation such as a roller system, a cut and slip unit or a bonding unit, however, is not a feature section because it only provides, forms or assembles a portion of a product feature of a finished disposable article. A roller system that provides a raw material web from a roll to a position parallel to a main web, for example, only provides the material to the web. That same roller system in combination with a cut and slip unit that cuts the web into discrete side panels and places them onto a main web and a bonding unit that combines the side panel material with the web, however, together completely assemble the side panel product feature and thus make up a feature section.

Many product upgrades seek to enhance the performance and/or the aesthetics of the product or decrease the cost of the product by changing one or more particular product features. A diaper product, for example, may be upgraded from a single cuff diaper having a gasketing cuff 536 to a multiple cuff diaper by adding a barrier leg cuff feature 538. Alternatively, a product line may manufacture multiple different products on the same line by changing one or more product features. A line may manufacture a unibody design diaper, for example, in which the side panels are created by cutting notches in the web to create leg openings of a diaper. That same line may also manufacture a multi-piece design diaper such as the diaper 550 shown in FIG. 51 in which the side panel feature of the unibody design diaper 500 is replaced by prefabricated back ears and front ears that may be produced off-line at a significant cost savings.

If the equipment that manufactures, attaches or assembles a complete or substantially all of product feature is physically co-located and commonly controlled, changing the production line to alter, replace or remove that feature from a product may significantly reduce the time and costs required for development, testing and line changeover efforts. In one particular embodiment, for example, each operational unit that is, or substantially all the operational units that are, used to manufacture, attach or assemble a particular product feature may be housed in one or more modules dedicated to that feature. These modules may be arranged adjacent to each other in the manufacturing line and may even be commonly controlled.

Although it is important that substantially each operational unit comprising a feature section be physically located in the same area of the line, such as within the one or more modules that comprise that particular feature section, it is not necessary that each operational unit making up a particular functional operation within that feature section be physically grouped together with the other operational unit(s) that together form that functional operation. In the back ear feature section I example, for instance, the bonding unit may include an adhesive applicator such as an adhesive sprayer or glue nozzle that is located upstream of the cut and slip functional operation, in between individual operational units that comprise the cut and slip functional operation or downstream of the cut and slip functional operation. The nip rolls that apply the pressure to bond the back ear to the web, however, are preferably located downstream of the cut and slip functional operation.

Module

Figure 1:
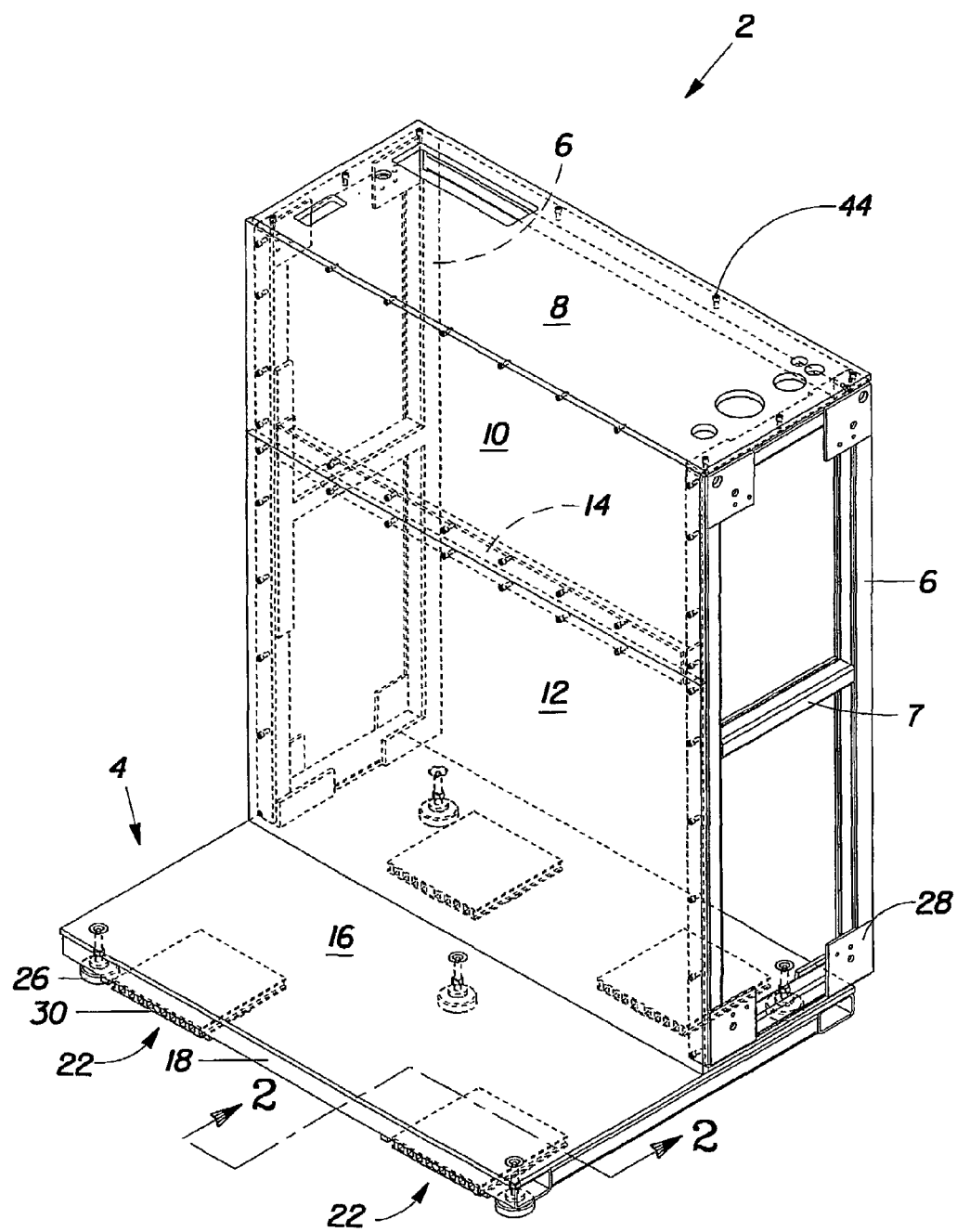
FIG. 1 is a simplified perspective view of a frame construction of a module of the present invention.
Figure 2:
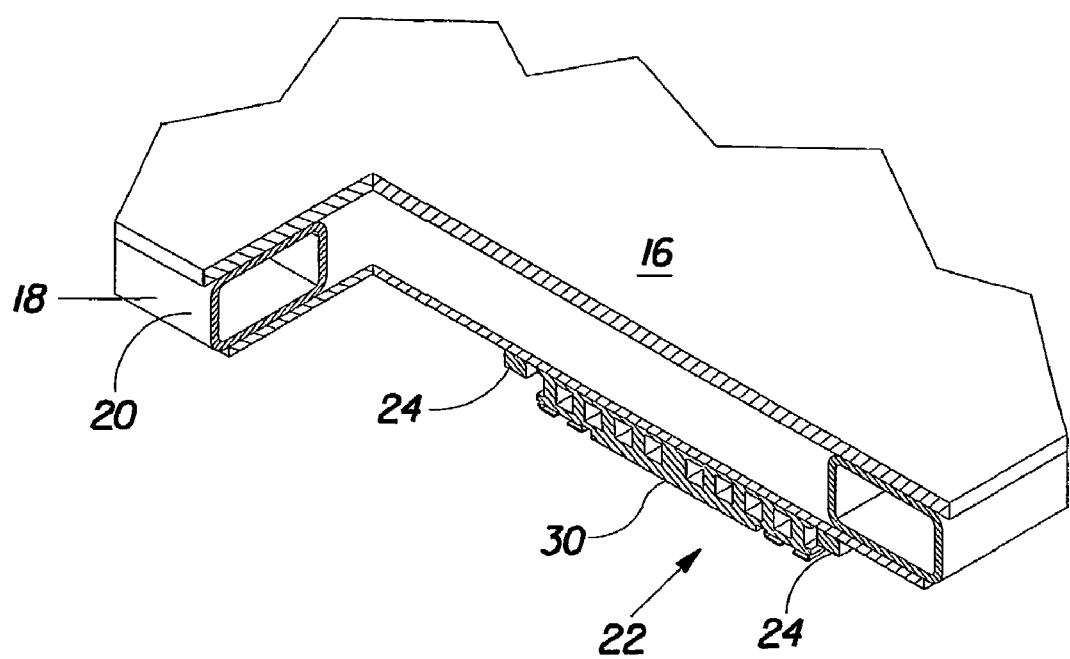
FIG. 2 is an enlarged cutaway view of a base of the module frame shown in FIG. 1.
Figure 12:
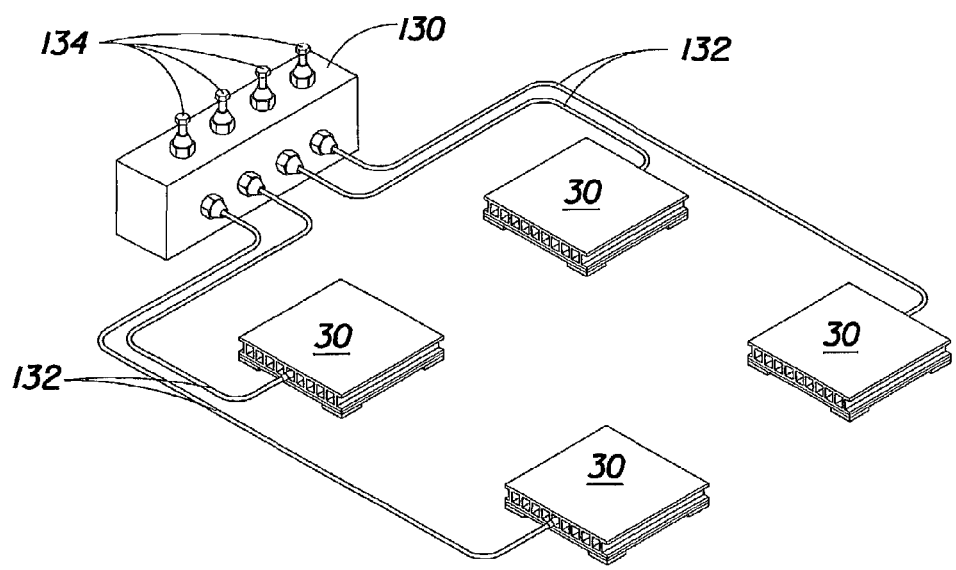
FIG. 12 is a simplified view of a manifold connected to four lifting mechanisms via compressed air lines.

FIGS. 1 and 2 show one embodiment of a module frame 2. The module frame 2 includes a base 4 having a horizontal plate 16 and a perimeterically welded bottom frame 18 formed from a rectangular tube 20. The horizontal plate 16 may be joined to the bottom 18 by welding, bolts, screws, pins or any other means used in the art. The top of the horizontal plate 16 may be connected to two side supports 6 by welding, bolts, screws, pins, etc. The two side supports 6 may be positioned vertically on opposite sides of the horizontal plate 16 and are generally perpendicular to the machine direction. (The term "machine direction" refers to the general direction in which the materials being processed move.) Each side support 6 may form a welded parallelepiped construction having a cross bar 7 and four side plates 28 at the four corners of the side support 6. The two side supports 6 may be connected by a top plate 8 and two vertical plates 10 and 12 such as by using screws 44. For added strength, the vertical plates 10 and 12 may be connected to a cross support 14 which also connects the two side supports 6. The vertical plates 10 and 12 may be of equal size or may be different sizes to accommodate different size operational units. Additionally, the module frame 2 may include one, two, three or more vertical plates such as the vertical plates 10 and 12 shown in FIGS. 1 and 3. The bottom of the horizontal plate 16 may be divided into four regions 22 such as by welded strips 24 for positioning a lifting mechanism 30 (described in more detail below) in each region 22. The module frame 2 may include various numbers of regions 22 and/or numbers of lifting mechanisms 30 depending upon the weight and distribution of the module load and the lifting capability of the lifting mechanisms 30. The lifting mechanisms 30 located under the base 4 may be inflated simultaneously in order to avoid unnecessary tilting of the module and its load. For this, a manifold 130 such as shown in FIG. 12 may distribute air among the lifting mechanisms via compressed air lines 132 connected between the manifold 130 and the lifting mechanisms 30 by adjusting valves 134. Further, the base 4 may include feet 26. In one embodiment, the feet 26 may be individually adjustable in order to level the module 2 and align the module to the rest of the converting line. The module frames may be uniform dimensions or may vary in size. In one embodiment, the width (dimension in the machine direction) may vary, for example, from about 1 meter to about 2.5 meters to allow for relatively easy handling of the module frame 2. In a particular embodiment, the width of the module frames 2 may be standard dimensions such as 1 meter, 1.5 meters, 2 meters, and 2.5 meters in order to provide standard modules that may be used to house various sizes and numbers of operational units, and that may limit the number of modules that need to be kept in an inventory to allow for exchange of any module in the converting line.

The term "module" refers to a single and physically independent container that may contain one or more operational units to allow the one or more operational units to be moved within a flexible manufacturing system of the present invention. The one or more operational units function inside the module such as by manipulating, transforming or temporarily changing a source material in a designed sequence of a manufacturing process. The module 60 illustrated in FIGS. 7–10, for example, contains the following operational units attached to the front of the vertical plates 10 and 12: two unwinds 62 and 64 for unwinding a landing zone material 66; two omega rolls 68 and 70 for metering the landing zone source material 66; an automatic splicer 72 for splicing the landing zone material 66; a dancer 74 for maintaining generally equal tension in the landing zone material 66; an omega roll 76 for feeding the landing zone material 66; a tracking device 78; an adhesive applicator 80 for applying adhesive on the landing zone material 66; an idler 82 and a turning bar 84 directing a backsheet material 86; an omega roll 85 for metering the backsheet material 86; and a tracking device 88 for tracking the backsheet material 86 into a cutting device 90. The backsheet material 86 may be fed from a reel 92 located on a side of the landing zone module 60 as shown in FIG. 36.

Figure 7:
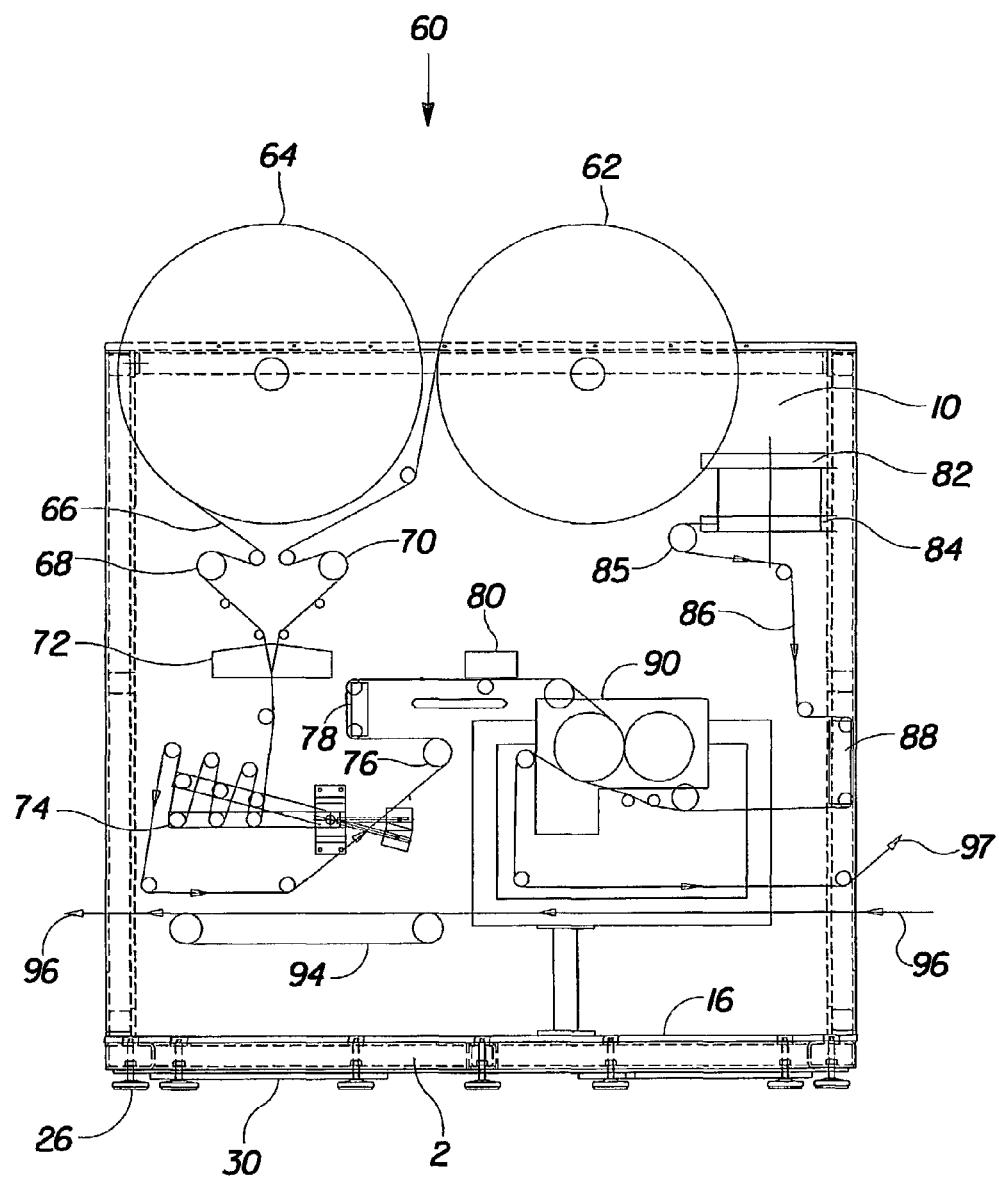
FIG. 7 is a simplified front view from an operator side of one of the modules of the present invention including operational units.
Figure 8:
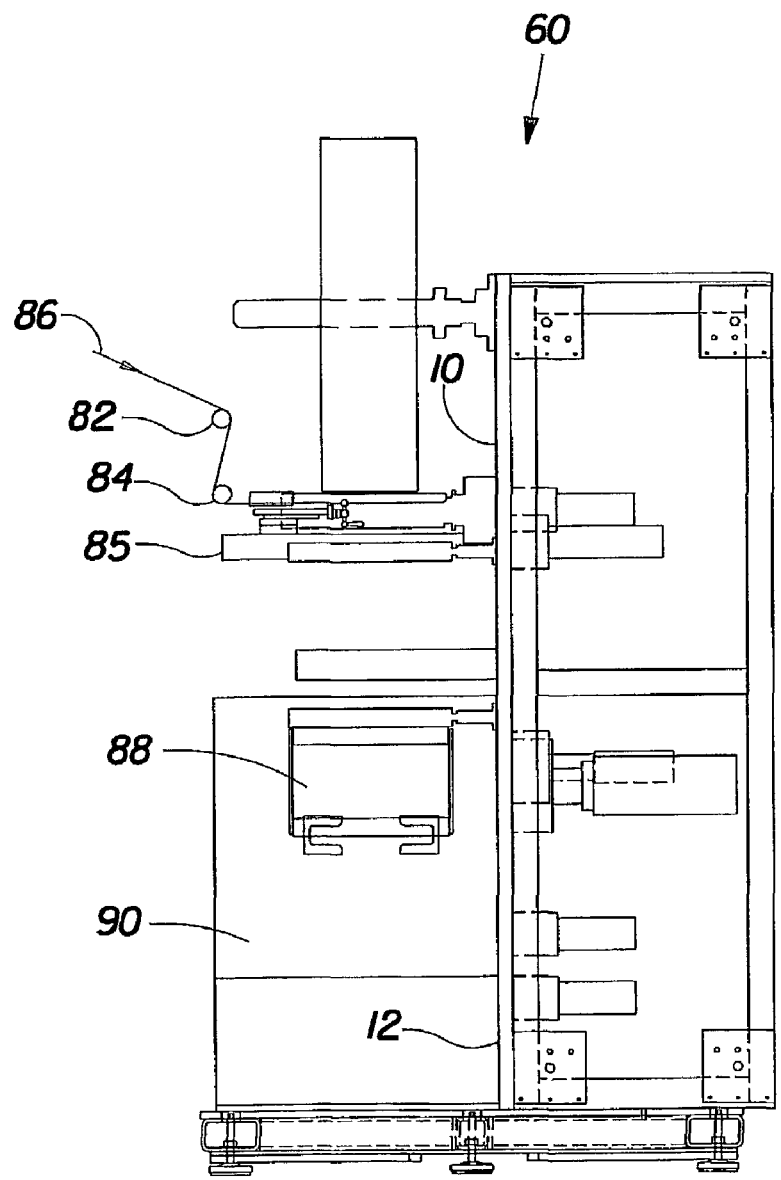
FIG. 8 is a simplified side view of the module shown in FIG. 7.

Some of the operational units, such as heavier ones, may be attached to the horizontal plate 16 or to both the horizontal plate 16 and one or more of the vertical plates 10 and/or 12. Cutting device 90, for example, is shown in FIGS. 7 and 8 connected to both the horizontal plate 16 and the vertical plate 12. The cutting device 90 may, for example, cut landing zone source material 66 and apply it onto a backsheet material 86. In addition, the module 60 may contain a conveyor 94 for conveying a combined material 96 that passes through the module 60 from the upstream operations to the downstream operations on the production line (from right to left in FIG. 7).

Figure 9:
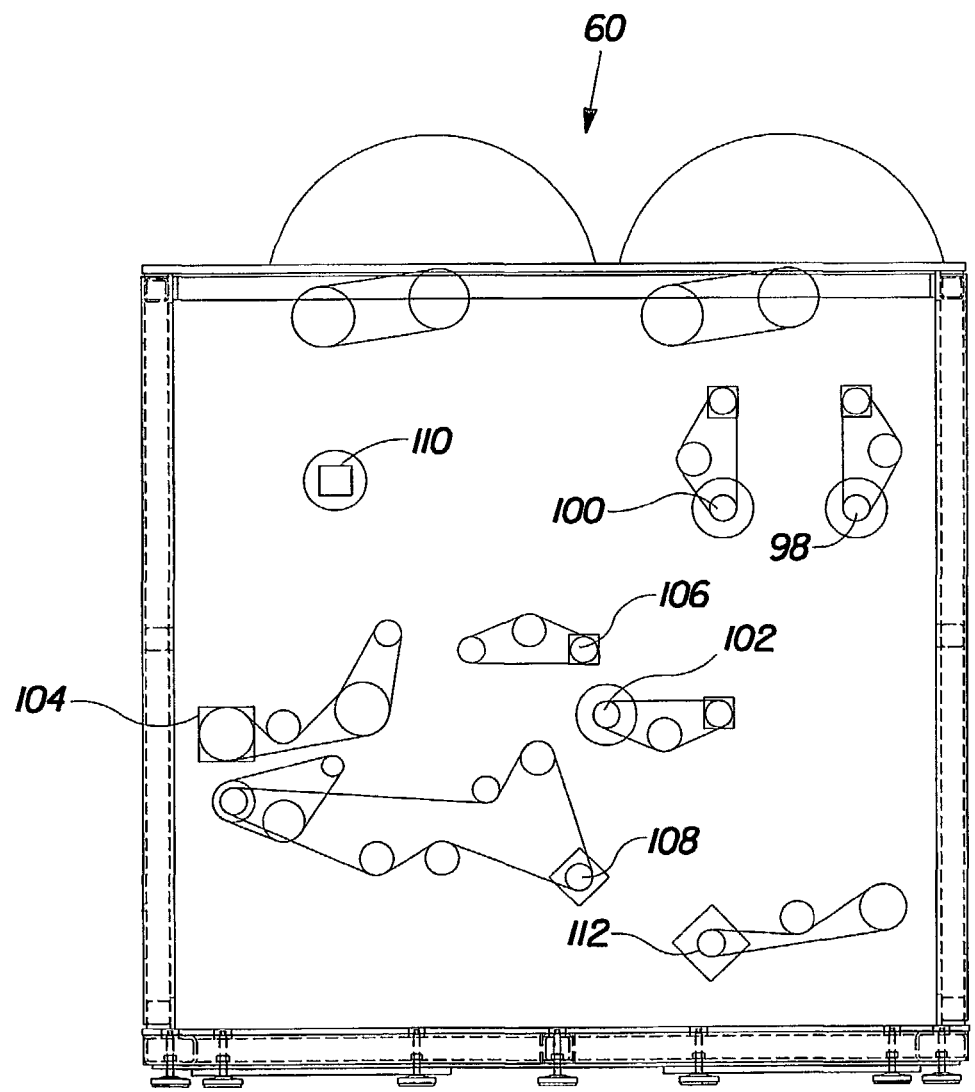
FIG. 9 is a simplified back view from the drive side of the module shown in FIGS. 7 and 8.
Figure 10:
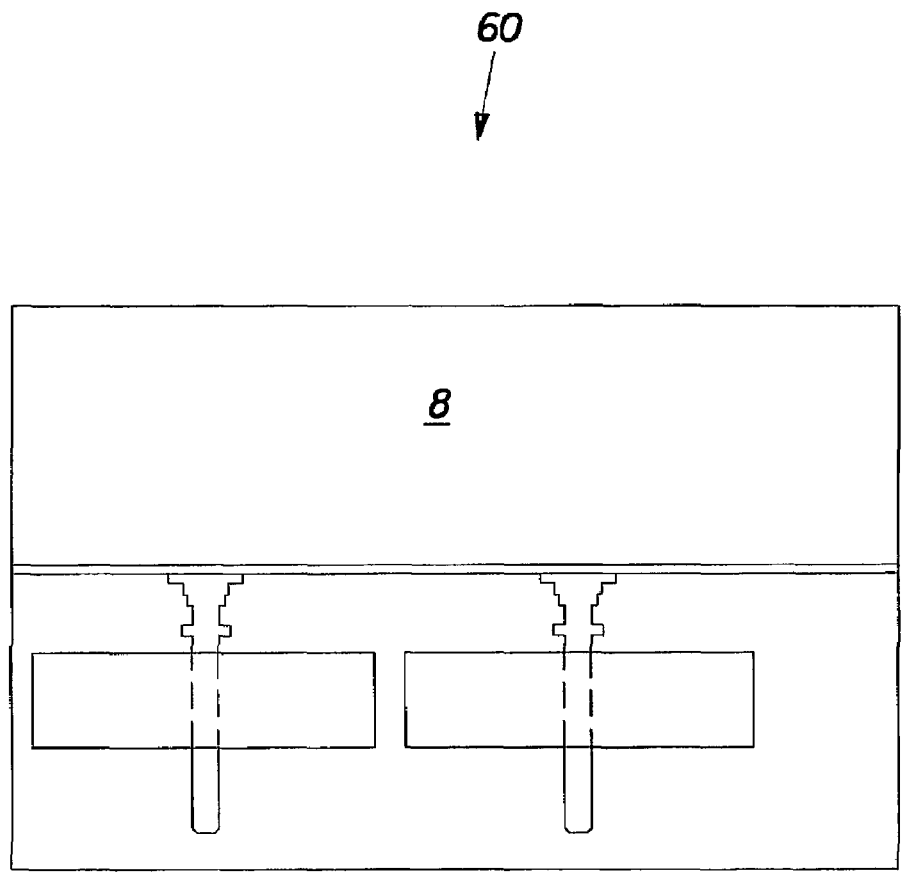
FIG. 10 is a simplified top view of the module shown in FIGS. 7–9.

As shown in FIGS. 8 and 9, electric motors, such as servo motors, dc motors, ac vector drive motors, etc., for driving the operational units may be attached to the back of the vertical plates 10 and/or 12. A "servo motor" may include a digitally controlled position servo motor and/or a digitally controlled velocity servo motor. A position servo motor is an electric motor controlled by regulating the position of an operational unit relative to a position of a reference signal and/or relative to a position of a product or a web. A velocity servo motor is an electric motor controlled by regulating the velocity of an operational unit relative to a velocity of a reference signal and/or relative to a velocity of a product or a web. Referring to FIGS. 8 and 9, the motors shown attached to the back of the vertical plates 10 and 12 are: motors 98 and 100 for the omega rolls 68 and 70, respectively; motor 102 for the omega roll 76; motors 104, 106, and 108 for the cutting device 90; motor 110 for the omega roll 85; and motor 112 for the conveyor 94.

Figure 11:
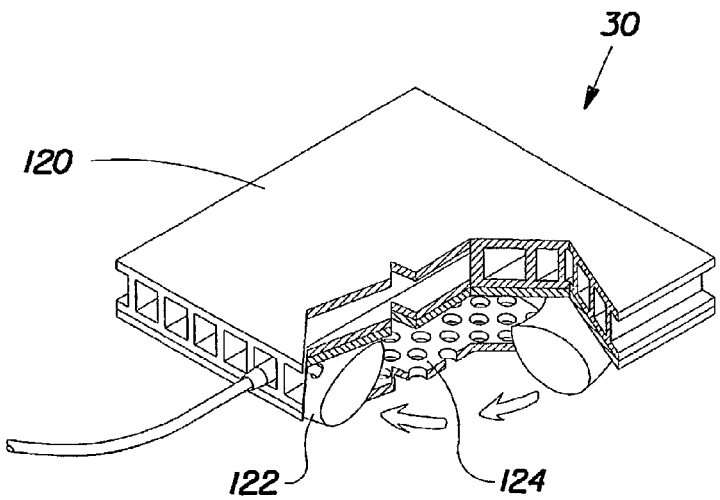
FIG. 11 is a simplified perspective view of a lifting mechanism of the present invention with a partially cut away front corner.

A module may be moved by means of lifting mechanisms 30 inserted under the base 4 as shown in FIGS. 1–2. The lifting mechanisms 30 may be used for smooth movements of loads over gaps in the floor surface by creating a cushion of air between the floor surface and the lifting mechanisms 30 supporting the lifted module. FIG. 11 illustrates the function of the lifting mechanism 30 supporting a load on a chamber plate 120. Compressed air or any other fluid may be pumped into a circular bag 122 which when inflated seals against the floor surface. (The term "air" used herein refers to any combinations of gases, including but not limited to atmospheric air.) When the air pressure in a chamber 124 exceeds the weight of the load located on the chamber plate 120, air generally slowly and evenly escapes between the circular bag 122 and the floor surface creating a cushion of air about 0.003 to 0.005 inches thick. The module floats on the cushion of air and may be moved around the floor for the purpose of arranging and/or re-arranging the production line. A suitable lifting mechanism may be GAPMASTER™ Aero-Caster manufactured by AeroGo, Inc., 1170 Andover Park West, Seattle, Wash. 98188-3909. The combined load capacity of four lifting mechanisms, for example, may be about 28,000 pounds for a 2.5 meter wide module. The ability to move the module may add flexibility to the flexible manufacturing system and allow for a change in a manufactured product in a more efficient manner.

Figure 3:
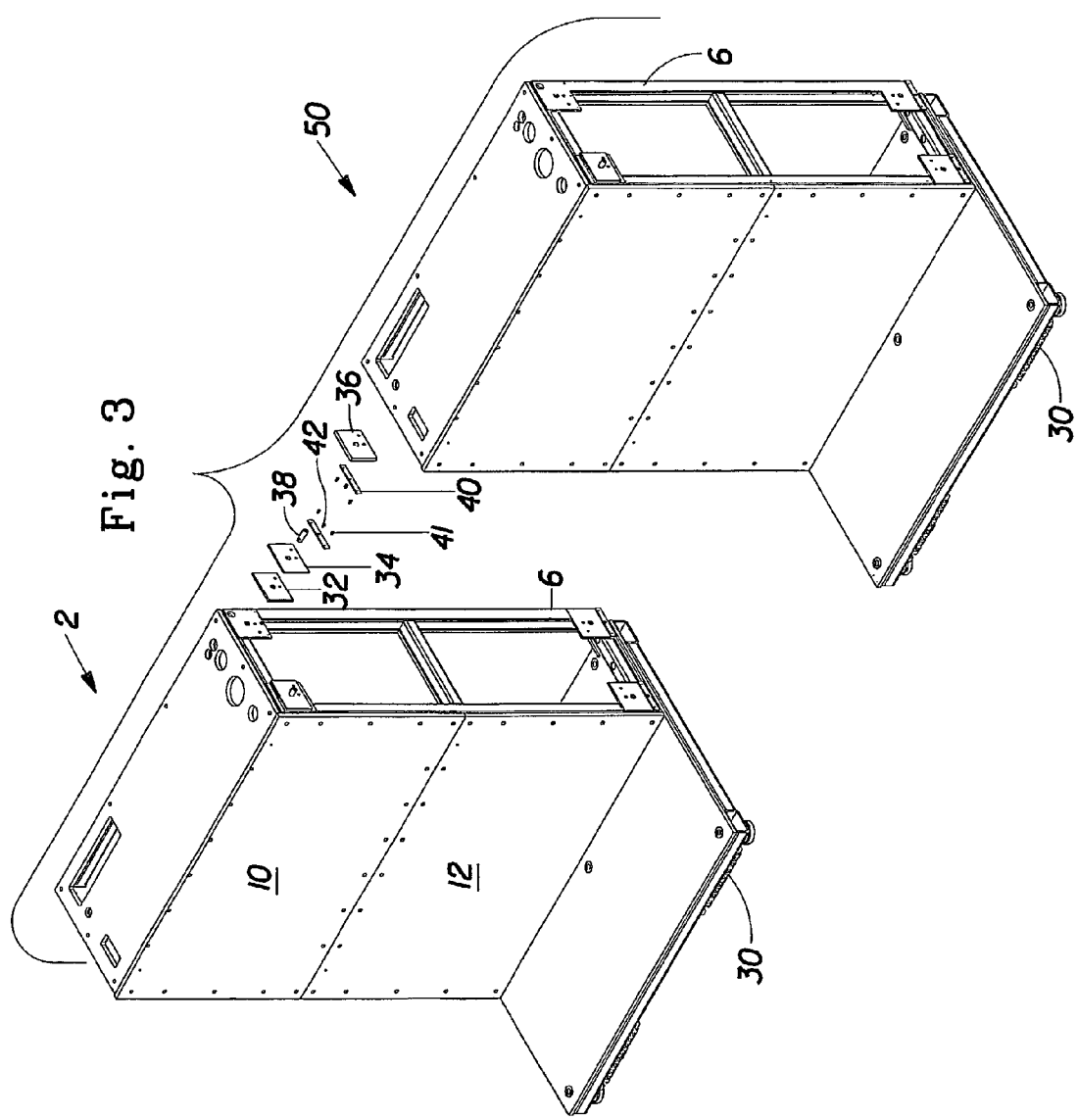
FIG. 3 is a simplified perspective view of two adjacent module frames to be attached to each other and an exploded perspective view of hardware for attaching two adjacent module frames.
Figure 4:
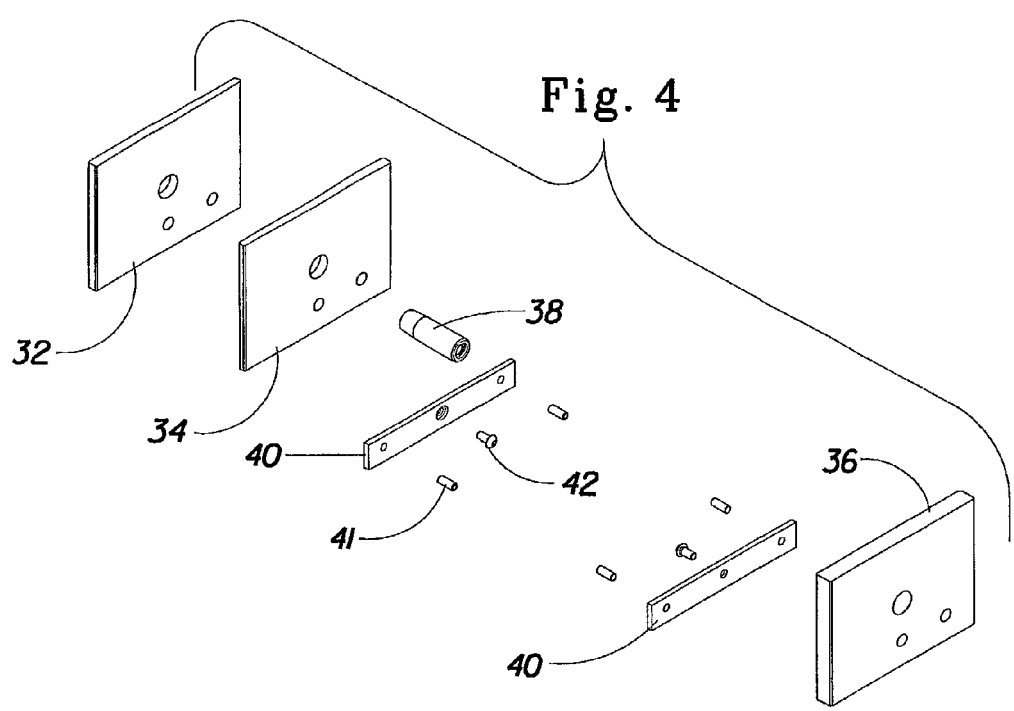
FIG. 4 is an exploded perspective view of the hardware for attaching the two adjacent module frames shown in FIG. 3.
Figure 5:
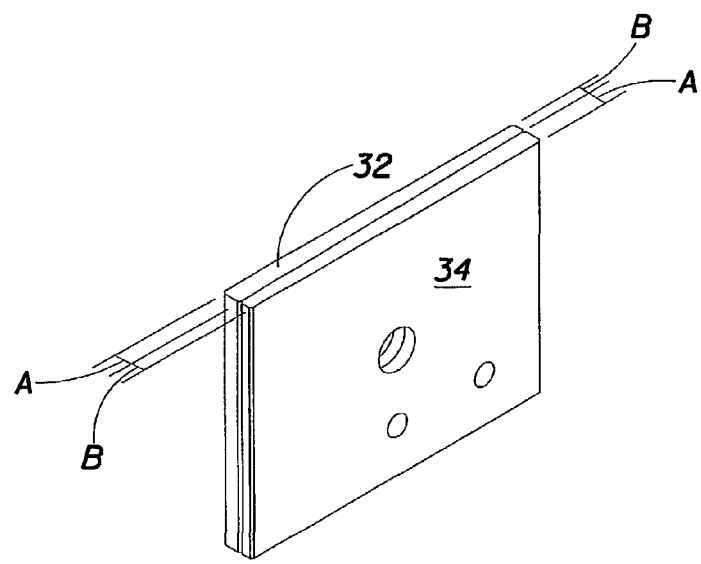
FIG. 5 is an enlarged perspective view of two paired wedges shown in FIG. 4.
Figure 6:
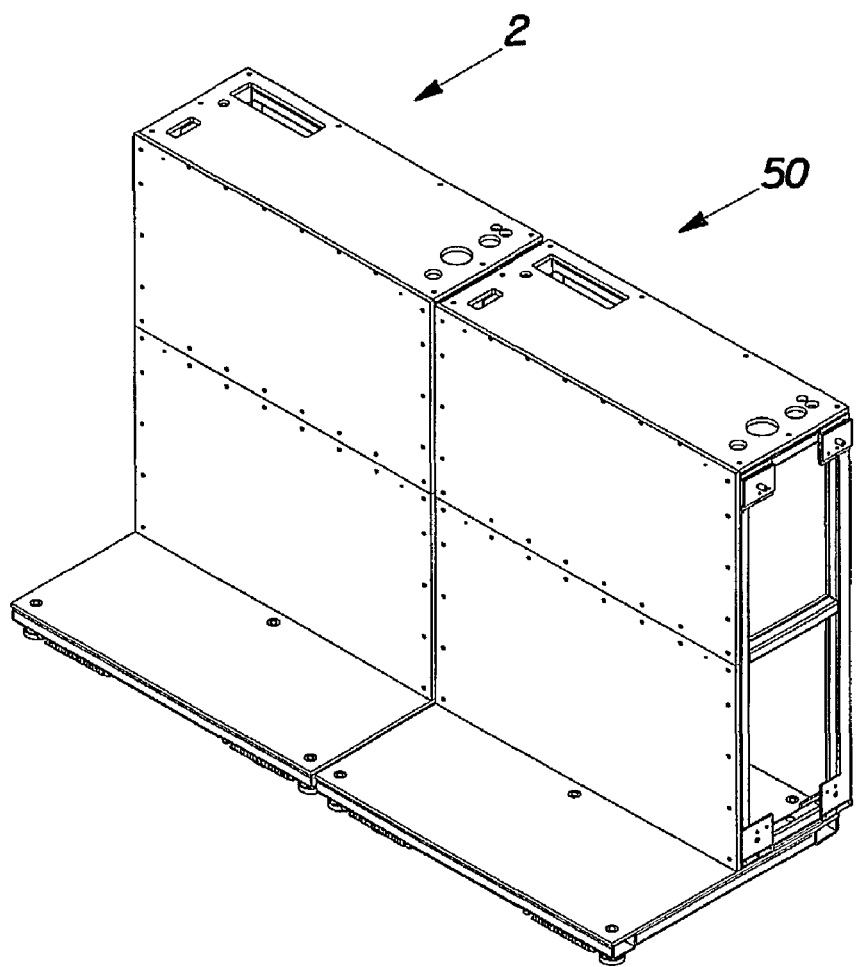
FIG. 6 is a simplified perspective view of the two adjacent module frames shown in FIG. 3 attached to each other.

After a module has been moved into a position adjacent to another module, the modules may be connected to each other at their respective side supports 6 as shown in FIGS. 3 and 6. In one particular embodiment, the side supports 6 may be substantially identical for each module. In this embodiment, the modules may be positioned with a space, such as a 20 mm space, between them in the machine direction, and a spacer 36 or a set of one or more wedges 32 and 34 may be inserted in the space created between the modules. The wedges 32 and 34, if used, may allow for easier insertion into the space between the module frames, especially, when a module frame is positioned between two other module frames. A pin 38 and two bolts may be inserted through the wedges 32 and 34 or through the spacer 36 and the corresponding side plates 28 of each of the connected module frames 2 and 50. An enlarged view of the exemplary connectors is shown in FIG. 4, and a separated view of the exemplary pair of wedges 32 and 34 is shown in FIG. 5. The bolts may be tightened with nuts to ensure a tight connection of module frames 2 and 50 as they are shown in FIG. 6. In one embodiment, one module may be joined to another module at two or more of the four corners of the side supports 6 because two or more pins may provide the alignment of the connected modules. The spacer 36 may be used on one side of the module and wedges 32 and 34 may be used on the opposite side of the module. In one embodiment, the modules may be positioned in a linear fashion along the machine direction, however, the modules may be positioned in any other arrangement. For example, modules may be arranged perpendicular to the machine direction and may assemble one or more product features and feed the product feature(s) into the manufacturing line. The system for aligning the modules including one or more of the wedges 32 and 34, the spacer 36, the pins 38 and the bolts described above is only one embodiment. Other known means of connection and alignment may be used within the scope of the present invention.

Figure 13:
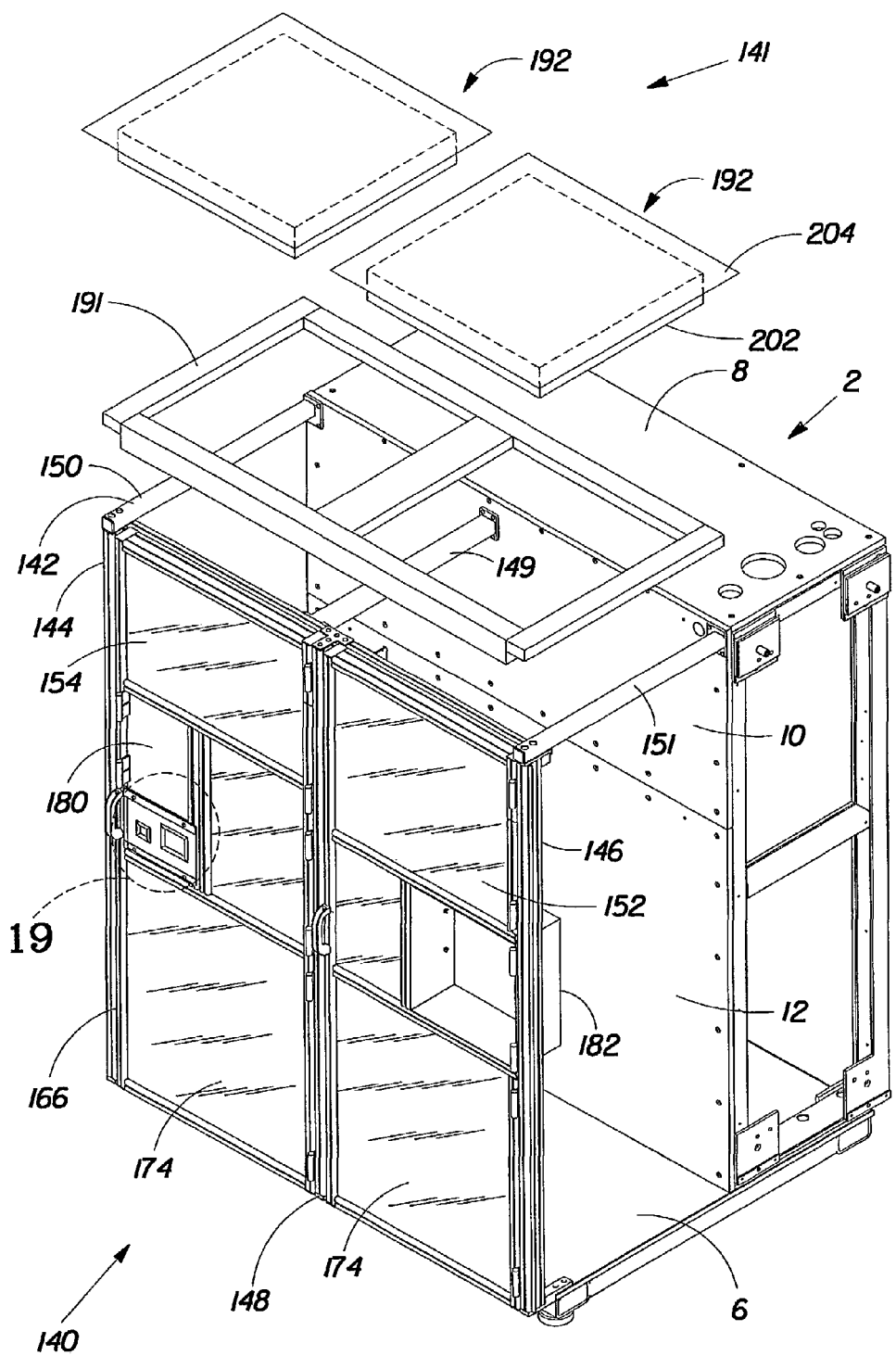
FIG. 13 is a is a perspective view of an embodiment of an enclosure for a sound suppression system enclosing the operator side of a module frame of the present invention.

Enclosure devices may be provided to suppress the noise level in the vicinity of the manufacturing line. FIG. 13, for example, shows a perspective view of one embodiment of an operator side enclosure 140 and a flat roof enclosure 141 both enclosing the operator side of the module frame 2. The operator side enclosure 140 includes a door support structure 142 comprising two end posts 144 and 146 attached to the opposite distal corners of the horizontal plate 16 of the module frame 2 and a mid post 148 located between the end posts 144 and 146. Each post 144, 146 and 148 is attached to the horizontal plate 16. The end posts 144 and 146 may be attached to the horizontal bars 150 and 151, respectively, and the mid post 148 may be attached to the horizontal bar 149. The operator side enclosure 140 may also include two doors 152 and 154 pivotally attached to the end post 146 and the mid post 148, respectively.

FIG. 15 shows a rear view of one embodiment of a drive side enclosure 160 enclosing the drive side of the module frame 2. The enclosure 160 includes two doors 162 and 164 each one pivotally attached to the two opposing side supports 6 of the module frame 2.

Figure 17:
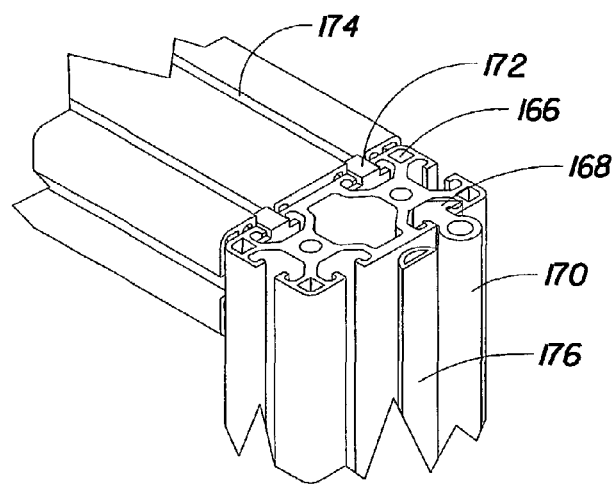
FIG. 17 is an enlarged perspective view of an embodiment of an aluminum extruded frame shown in FIGS. 13, 15 and 16.
Figure 18:
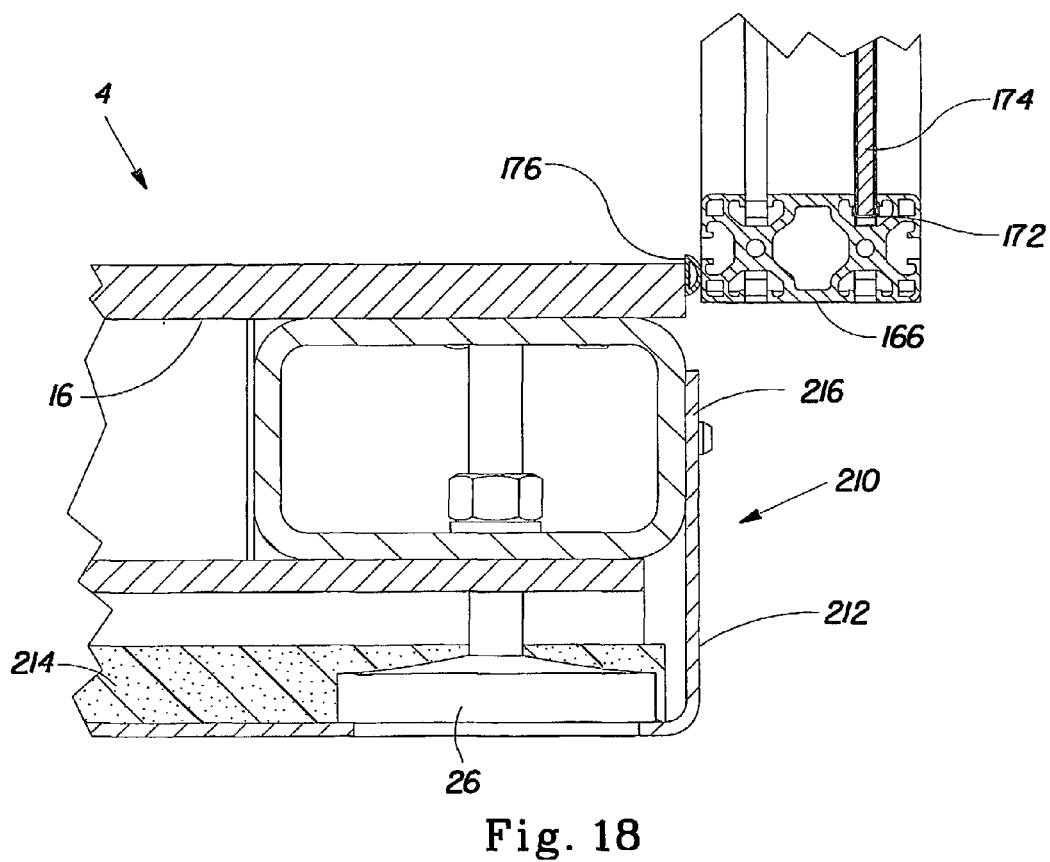
FIG. 18 is an enlarged view of section 18 shown in FIG. 15.
Figure 19:
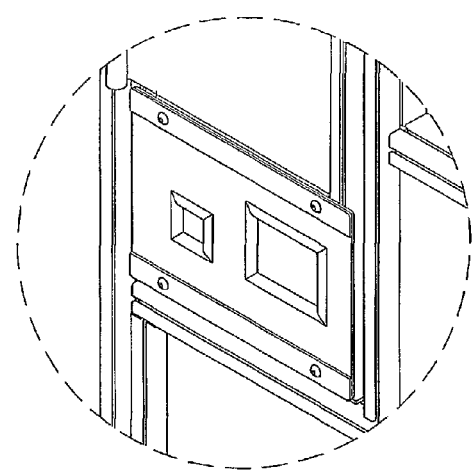
FIG. 19 is an enlarged view of area 19 shown in FIG. 13.

In one embodiment of the present invention, the operator side doors 152, 154 and the drive side doors 162, 164 may be assembled from a commercially available aluminum extrusion frame 166, shown in an enlarged perspective view in FIG. 17. The aluminum extrusion frame 166 may include oppositely located slots 168 suitable for inserting a sponge extrusion seal 170 on one side of the aluminum extrusion frame 166 and a seal 172 enclosing a transparent polycarbonate sheet material 174 on the other side of the aluminum extrusion frame 166. The transparent polycarbonate sheet 174 may be of a thickness from about 6 mm to about 12 mm of Lexan, Makrolon or any other brand. The aluminum extrusion frame 166 and the corresponding seals 170 and 172 may be purchased from Item Industrietechnik and Maschinenbau GmbH of Germany. To all surfaces opposing the doors, a self adhesive gasket 176 may be adhesively attached, as shown in FIGS. 17 and 18. The self adhesive gasket 176 may be purchased from Clean Seal Co. of South Bend, Ind.

Figure 20:
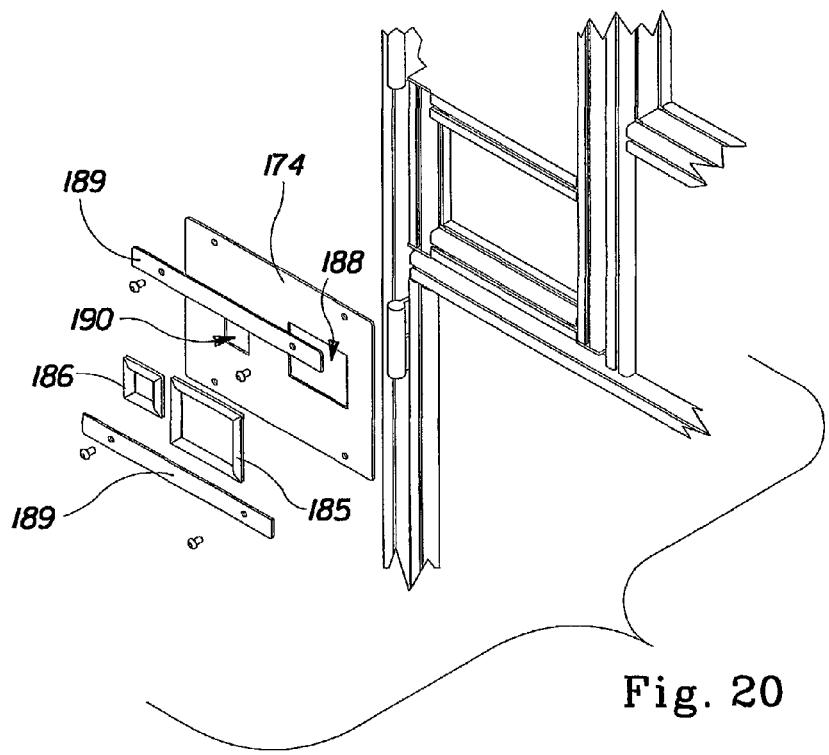
FIG. 20 is an exploded view of area 19 shown in FIGS. 13 and 19.

As shown in FIGS. 13 and 15, the operator side doors 152 and 154 and the drive side doors 162 and 164 may include panel boxes 180, 182 and/or 184 for accepting various control devices described in more detail below. For example the box 180 may be used for an operator interface, the box 182 may be used for a vision system monitor, the box 184 may be used for a junction box such as an electrical junction box or an adhesive junction box, etc. The number and the type of panel boxes may vary. The panel boxes may be pivotally attached to the door frame 166 as shown in FIG. 13 for the panel boxes 180 and 182. The pivotal arrangement enables an operator or maintenance personnel to view the pivoted control device when the door is open for accessing the machine. The self adhesive gasket 176 shown in FIGS. 17 and 18 may be adhesively attached to the panel boxes to insure a tight seal around the perimeter of the panel boxes. Other control devices such as an electrical disconnect switch or an air dump switch may be attached directly to the transparent polycarbonate sheet 174 through seals 185 and 186, respectively, as shown, for example in FIG. 20. The seals 185 and 186 enclose openings 188 and 190, respectively, from both sides of the transparent polycarbonate sheet 174. The operator side doors 152 and 154 and the drive side doors 162 and 164 may be of about the same length as the corresponding module which, for example, may vary from about 1 meter to about 2.5 meters in about 0.5 meter intervals.

Figure 14:
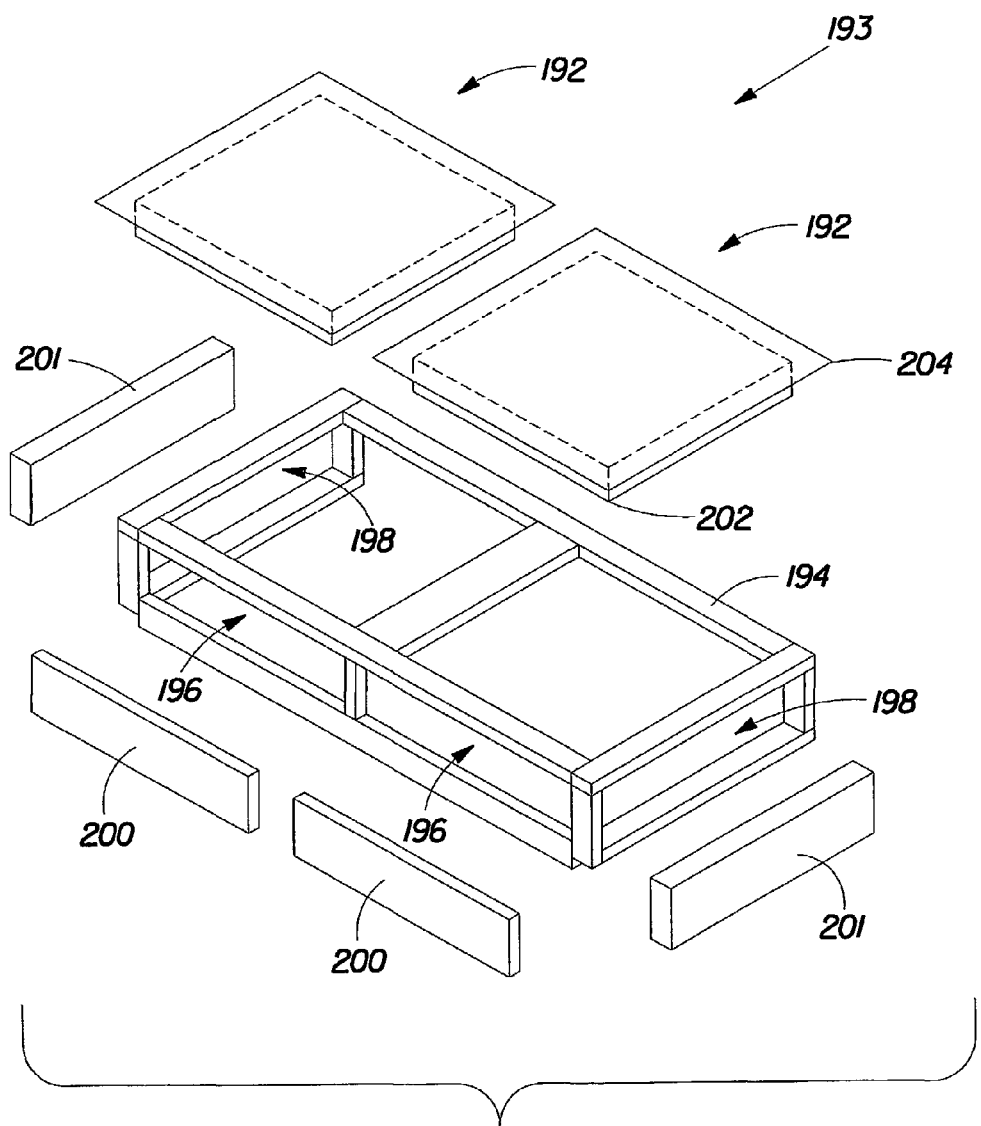
FIG. 14 is an exploded perspective view of a raised roof enclosure.

Other sound suppressing enclosures may include roof enclosures for enclosing the top of the operator side of the module frame 2. One embodiment of a roof enclosure 141 is shown in FIG. 13. In this embodiment, two roof elements 192 may be positioned on a roof platform 191. In another embodiment shown in FIG. 14, a raised roof enclosure 193 may include roof elements 192 located on a platform 194 to create open areas 196 for supplying material webs, optionally, from the operator or from the drive sides of the manufacturing system, or from above the manufacturing system. (The modules may be configured so that material webs can be received from either the operator or the drive side of the module, or from above the module. Rotating a turning bar 180 degrees, for example, may be all that is necessary to change from one side to another side. Each material delivery option may offer a different advantage. Having the materials on the operator side consolidates an operator's work to one side of the machine. The operator may load the materials and monitor the production process more effectively with this arrangement. Locating the materials on the drive side may permit installation in manufacturing plants with narrowly spaced building columns. Having the materials stored above the modules may also conserve floor space in the manufacturing system.) The front opening 196 may be closed by an acoustic absorbent foam

200. The side openings 198 may be closed by an acoustic absorbent foam 201. The roof element 192 may include an acoustic absorbent foam 202 attached to a steel sheet 204. The foams 200–202 may be about 50 mm thick and protected by a perforated steel sheet or a fabric or any other suitable means. For example, the acoustic foams 200, 201 and 202 may be a melamine foam purchased from Illbruck Co. of Minneapolis, Minn. The roof enclosures 141 and 193 may be of about the same length as the corresponding module.

Still another sound suppressing enclosure may include a base enclosure 210 shown in FIGS. 16 and 18. The base enclosure 210 may include a dense containment layer 212 built of sheet steel and an acoustic absorbent foam 214, similar to the foams 200–202 above, and similarly protected by perforated sheet steel or a fabric or any other suitable material. The base enclosure 210 may be inserted under the module frame base 4. The containment layer 212 is formed along one edge to create a vertical wall 216 which may be attached to the module frame base 4, thus closing off the space between the floor and the module frame base 4. The vertical wall 216 may be attached to only one module in order to ensure that when that module is removed, the neighboring base enclosures are not disturbed. Each module may have at least two base enclosures 210 inserted under the module frame base 4 from two opposite sides, preferably from the operator side and from the drive side. There may be a soft compliant synthetic rubber seal for closing the gap between the at least two opposite base enclosures 210. The base enclosure 210 may be the same length as the corresponding module.

Further, end barriers may be used to close a side of a module when the end of the module is exposed at the end of a series of modules. The end barrier may be constructed similar to the roof element 192. Alternatively, if the side of the module needs to be visible, the end barrier may be constructed similar to the operator side doors 152 and 154 and drive side doors 162 and 164 with large transparent polycarbonate sheets 174 as shown in FIG. 13.

Finally, the above enclosures may be complemented with absorbent baffles 220 suspended inside the operator side or the drive side of the module when additional localized sound suppression is needed. The absorbent baffles 220 may be constructed of an acoustic foam 222 enclosed in a frame 224 including perforated sheet steel. Alternatively, the acoustic foam 222 may be enclosed by a protective fabric or any other suitable material. The absorbent baffles 220 may be suspended by hangers 226 constructed of any suitable material.

Control Structure

A flexible manufacturing system of the present invention may include at least one feature section and a control system that controls the operation of the one or more operational units of the feature section(s). An individual operational unit may include one or more motion elements, such as a motor, and/or one or more logical devices, such as a valve, solenoid, relay, gate, sprayer, nozzle, switch, light, lamp, etc. The control system may control the operation of one or more individual operational units and/or synchronize or coordinate the operation of the individual operational units to the rest of the flexible manufacturing system.

The control system may include "local control functions" and "global control functions." A "local control function" refers to a function that is specific to the control within a particular feature section. A local control function, for example, may include motion, drive or logic control of individual operational units within a specific feature section. "Motion control," as used in this application, refers to position control of one or more motors or profiled motion control of one or more motors such as camming or trajectory control. "Drive control" refers to continuous velocity and position control of one or more motors. "Logic control" includes using one or more logic functions to control the actuation of a logical device. A "logic function" may include, for example, combinational logic functions such as "if then else" functions, sequence functions, "jump to subroutine" functions, timer counter functions, etc. A local motion/drive control function, for example, may include controlling the velocity and/or position of a motor in a feature section. A local logic control function may include, for example, using logic functions to control the starting or stopping of an operational unit within a feature section, or actuating a solenoid, a reject gate or a safety disconnect switch within a feature section.

A "global control function" refers to a control function that pertains to synchronizing or coordinating a local control function for a particular feature section to the remainder of the flexible manufacturing system. A global control function may synchronize or coordinate a local control function to the remainder of the flexible manufacturing system, for example, by informing the local control function of an event that occurred outside of the feature section, or by providing the local control function a reference signal that may be used by the local control function to synchronize or coordinate the operation of an operational unit within the feature section to the remainder of the flexible manufacturing system. A global control function may include, for example, a global motion, drive and/or logic control function that synchronizes or coordinates the operation of a local motion, drive and/or logic control function within a feature section with the operation of the rest of the flexible manufacturing system, a global start/stop logic control function that synchronizes or coordinates a local stop or start control function with the starting or stopping of the rest of the flexible manufacturing system, a global reject logic control function that synchronizes or coordinates a local reject logic control function with the rest of the flexible manufacturing system, or a global safety disconnect logic control function that synchronizes or coordinates a local safety disconnect logic control function with the rest of the flexible manufacturing system.

A global motion/drive control function that synchronizes or coordinates local motion/drive control functions is one example of a global control function. In one embodiment, for example, a global motion/drive control function may synchronize the local motion/drive control functions by providing a velocity and/or position reference signal to a local motion/drive control function that, in turn, controls a motor based upon the reference signal such as by a feedback or feed-forward control system. The reference signal may, for example, provide a velocity and/or position reference such as a digital or analog signal that ranges in amplitude, phase angle and/or frequency proportionately with the desired velocity and/or position of the overall flexible manufacturing system or of a product for synchronizing the local motion/drive functions with the overall operation of the flexible manufacturing system. This reference signal may be based upon a mechanical reference, such as a traditional master drive motor or mechanical line shaft, to which the velocity and/or position of motors within one or more feature sections may be matched. Alternatively, the reference signal may be a "virtual" or electronically generated reference signal that is generated by the global motion/drive control function and provided to the local motion/drive control functions to control particular motors within the flexible manufacturing system. A virtual reference signal may be generated by solid state electronic hardware and/or software that may be immune from mechanical disturbances such as backlash or friction.

A global logic control function may also coordinate the operation of local logical control functions. A global logic control function may, for example, provide start and stop signals to local logic control functions to coordinate the local logic functions to the rest of the flexible manufacturing system. A global logic control function may also provide a logic reference signal that allows the local logic controllers to control the timing of logical device operation to the rest of the flexible manufacturing line. Alternatively, a local logic control function may utilize the velocity and/or position reference signal generated by a global motion/drive control function as described above (or, a local motion/drive control function may utilize the velocity and/or position reference signal generated by a global logic control function). In one embodiment, for example, the global logic control function may provide a digital or analog signal that may range in amplitude, phase angle or frequency proportionately with the desired velocity and/or position of the flexible manufacturing system or of a product for coordinating the local logic control function with the operation of the rest of the flexible manufacturing system. As described above with respect to the global motion/drive control function, the logic reference signal may be based upon a mechanical reference or a virtual reference.

As described above, a flexible manufacturing system of the present invention may include one or more feature sections. In one particular embodiment, for example, one or more of the feature sections may be controlled directly by a local feature control function. In this embodiment, the local feature control function may utilize a reference signal provided by a global control function to coordinate the operation of at least one motor and/or one logical device of the feature section to the remainder of the flexible manufacturing line. In a particularly preferred variation of this embodiment, the flexible manufacturing system includes at least two independent feature sections that each include a local control function that is adapted to directly control motors and logical devices for that feature section and to synchronize or coordinate those motors and logical devices to the rest of the flexible manufacturing system by utilizing one or more reference signals. In another variation, the local control function of each feature section may be adapted to directly control the motors and logical devices for that feature section in either a standalone mode or in the event that the feature section is integrated into an overall converting line.

Figure 55:
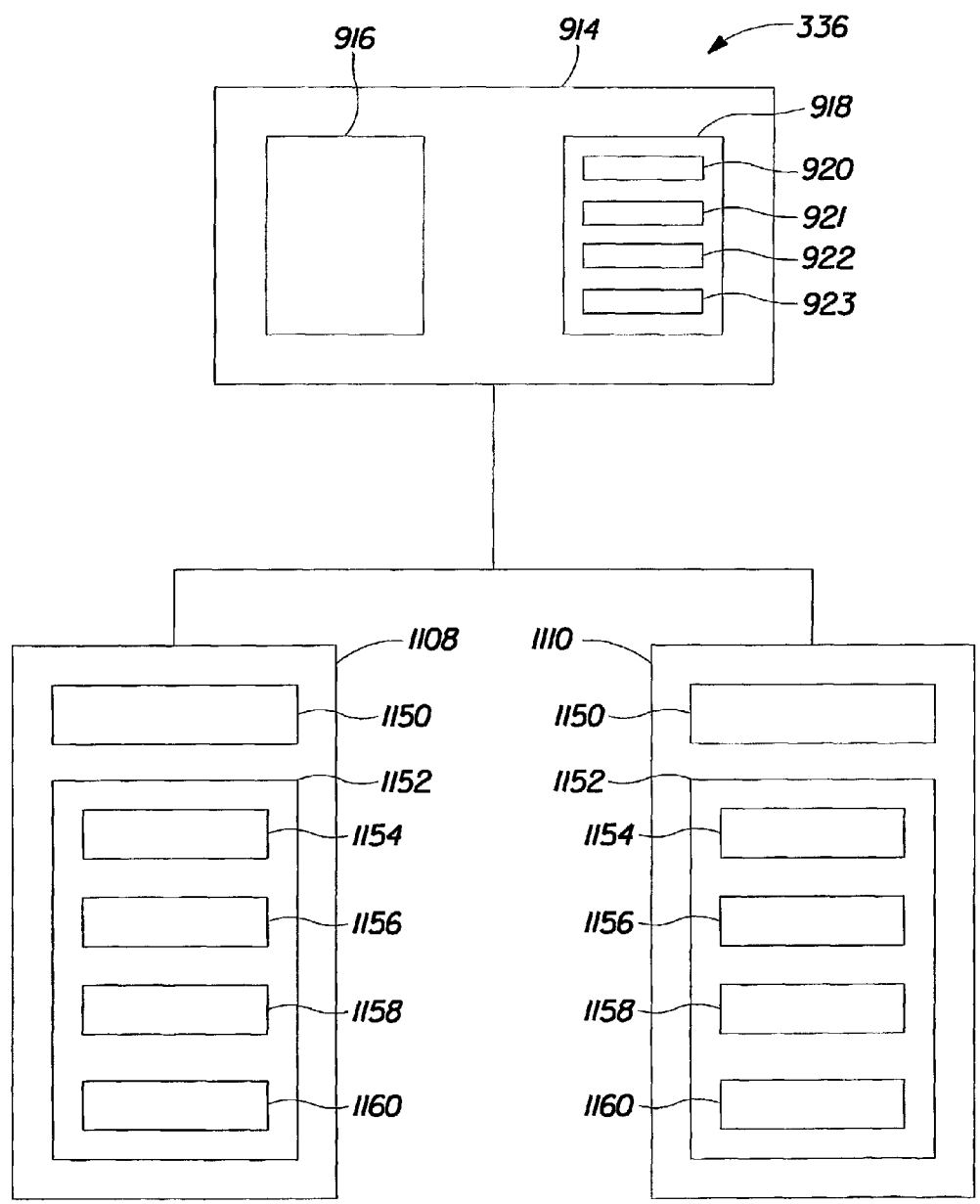
FIG. 55 is an example of one embodiment of a standard central computer panel.

The global control functions and local control functions may be performed by or reside in a central computer, a local controller or a combination of a central computer and one or more local controllers. In one embodiment, the control system may include a central computer that performs global control functions and one or more local controllers that each perform local control functions for a particular feature section. In FIG. 55, for example, exemplary global control functions and local control functions are depicted in the form of a block diagram. In this embodiment, the global control functions reside in the central computer 336, which may comprise software and/or hardware to perform global control functions such as a global motion/drive control function 916 and/or a global logic control function 918. Examples of a global logic control function include a global operator interface control function 920, a global start/stop control function 921, a global reject control function 922, and a global safety disconnect function 923. The local control functions may reside in feature local controllers, such as 1108 and 1110, which may comprise software and/or hardware to perform local control functions such as a feature local motion/drive control function 1150 and/or a feature local logic control function 1152. Examples of a local logic control function include a feature local operator interface control function 1154, a feature local stop/start control function 1156, a feature local reject control function 1158 and a feature local safety disconnect feature control function 1160. In another embodiment, the central computer may perform both the global control functions and the local control functions for controlling the operation of one or more feature sections. In this embodiment, the central computer may comprise an integrated platform with local control software distributed on a per feature basis, i.e., the software performing the local control function for at least one feature section may comprise a separate control routine or data block. Although the separate control routine or data block may include calls to shared subroutines or may include shared data, the separate control routine or data block preferably includes at least one portion that is distinct to a particular feature section so that the control routine or data block for that feature section may be easily located in the event that the feature section is modified, moved within, added to or removed from the flexible manufacturing system. In yet another embodiment, the control system may include two or more local controllers without a central computer. In this embodiment, the local controllers each perform the local control function for a particular feature section. In addition, one or more of the local controllers perform the global control functions for the overall flexible manufacturing system as well as the local control functions for a particular feature section.

Figure 54:
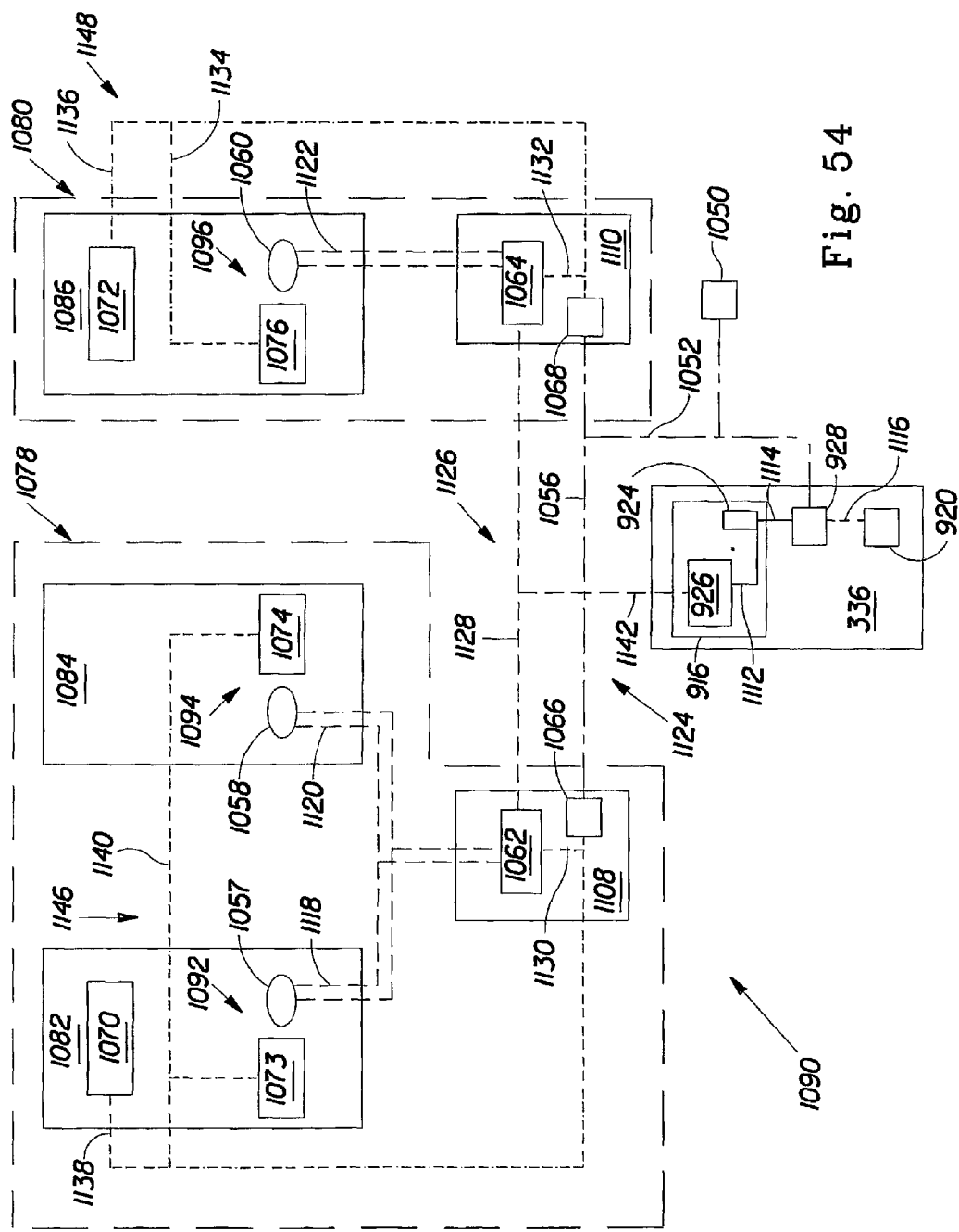
FIG. 54 is a block diagram of a communication network showing a central computer which could be used to synchronize two or more feature sections.

In the embodiment shown in FIGS. 54 and 55, for example, the central computer 336 may perform the global motion/drive control function 916 that synchronizes the operation of local motion/drive control functions 1152. In this embodiment, the central computer 336 may provide a reference signal that a local motion/drive controller may use to synchronize one or more motors that the local motion/drive controller is controlling. A "motion/drive controller" refers to a microprocessor-based system that controls the current, velocity and/or position of one or more motors. A motion/drive controller may also synchronize the operation of one or more motors such as by utilizing a reference signal provided by a global motion/drive control function. The motion/drive controller may, for example, control the velocity and/or position of a servo motor, a dc motor, an ac vector drive motor, etc. A motion/drive controller may also be capable of being integrated into a network of motion/drive controllers that synchronize one or more motors to a master machine velocity and position. The central motion/drive controller 916 may directly control individual motors in a flexible manufacturing system or may provide a velocity and/or position reference signal over a network to one or more local motion/drive controllers. Each local motion/drive controller, such as local motion/drive controllers 1062 and 1064, may utilize the reference signal to synchronize the motor(s) that it directly controls to the rest of the flexible manufacturing system. The central motion/drive controller 916 may, for example, include a master motion/drive reference 924 and a motion/drive control signal converter transmitter 926. The master motion/drive reference 924 may provide a reference signal that may be used to synchronize the operation of a feature section to the rest of the flexible manufacturing system. The master motion/drive reference 924 may be connected to a central motion/drive control signal converter transmitter 926 by a motion/drive reference link 1112 and to a central logic controller 928 by a motion/drive reference link 1114. The motion/drive reference links 1112 and 1114 may, for example, be variable frequency, phase angle and/or amplitude links. The central logic controller 928 may be connected to a central operator interface 920 by a network link 1116.

The global motion/drive control function may generate a virtual reference signal via solid state electronic hardware and/or software, which may be immune from mechanical disturbances such as backlash and/or friction. In one embodiment, the master motion/drive reference 924 may provide a virtual reference velocity and/or position signal for synchronizing the operation of a feature section to the rest of the flexible manufacturing system. The master motion/drive reference 924 may, for example, serve as an electronic encoder or resolver simulator and produce a signal comprising a series of pulses having a frequency that is relative to the desired velocity and/or position of the production line. The pulses may be configured in quadrature such that the master motion/drive reference signal is multiplied by four to obtain a higher resolution and accuracy. The pulses may also be converted into a serial format and transmitted over a network via a serial link to multiple local motion/drive controllers.

In one embodiment, the central computer 336 may include a velocity input preprogrammed into the central computer 336 or may accept a velocity reference input from the central operator interface 920 via the central logic controller 928 or from one or more of the local feature operator interfaces such as 1070 and 1072. In this embodiment, the central computer 336 may convert the velocity reference input into an input signal to the master motion/drive reference 924 using an algorithm in the central logic controller 928. Further, the central computer 336 may vary the input signal provided to the master motion/drive reference 924 or other master machine reference hardware. The algorithm, for example, may vary the input signal provided to the master motion/drive reference 924 while the machine is moving so that the line can ramp up and down to predefined set points pre-programmed in the central computer or entered by the operator on an operator interface 920.

In an alternative embodiment, the master motion/drive reference signal may originate from a master drive motor or from a mechanical line shaft. In one embodiment, the master motion/drive reference signal may be proportional to the velocity and/or position of a master drive motor or a mechanical line shaft in the flexible manufacturing system. The central computer 336 may, for example, receive a motor reference signal such as from an encoder or a resolver mounted on the master drive motor or the mechanical line shaft. The motor reference signal may then be converted to or used as a master motion/drive reference signal and distributed via a network such as the motion/drive control sub-network 1126. A local motion/drive controller, such as the first feature local controller 1062, may use this master motion/drive reference signal to control the velocity of drive motors in that feature section. An exemplary control signal that may be generated as the master motion/drive reference signal is described in U.S. Pat. No. 5,383,988 entitled "Modular Apparatus for Fabricating an Absorbent Article," issued to Thomas R. Herrmann et al. on Jan. 24, 1995, which is incorporated by reference in this application.

A "logic controller" refers to a microprocessor-based system that uses logic functions to control the actuation of and/or synchronization of logical devices such as solenoids, relays, valves, gates, sprayers, nozzles, switches, lights, lamps, etc. In one embodiment, a logic controller may be capable of being integrated into a network of logic controllers to pass information for the purpose of integrated logic control. The central logic controller 928 may directly control individual logical devices in a flexible manufacturing system and/or may provide a reference signal to a network of feature local controllers, such as feature local controllers 1108 and 1110, that directly control the logical devices of the operational units within features of the flexible manufacturing system. The global logic function 918 may be performed by a central logic controller 928. The central logic controller 928 may generate a velocity and/or position reference from pre-defined set points programmed into the central logic controller or from an operator interface, such as the central operator interface 920, and control the reference via software in the central logic controller 928. The central logic controller 928 may be integrated into a logic control network 1124 with the first and second feature local logic controllers 1066 and 1068, respectively, by logic control network links 1052 and 1056. A standard series of software steps that performs functions such as logic control and information processing may be integrated in the logic controllers. In one embodiment, for example, the central and/or local feature logic controllers may include a programmable logic controller ("PLC") in which a standard series of software steps that perform control functions and information processing are integrated into the PLC. In another embodiment, however, the central and/or local feature logic controllers may include a personal computer ("PC"), a mainframe, a micro computer or a mini computer in which flowchart programming techniques may be utilized to perform control functions and information processing.

The central logic controller 928 may function as a network system integrator. Information generated in one or more of the feature local controllers 1108 and/or 1110 may be passed to the central computer 336 via a digital or analog network. The central logic controller 928 may integrate the starting and stopping of one or more feature sections by transmitting signals to and from the one or more feature section local controllers over the network. In addition, the central logic controller 928 may also control a power distribution system and/or integrated safety systems via the network. Further, the central logic controller 928 may monitor and control utilities for supporting operational units, such as adhesive tanks, vacuum systems, compressed air, glycol, etc. The central logic controller 928 may also accumulate production data information, such as a number of products made, a mean time between failure, a line efficiency, etc., and display the information on the main operator interface or transmit the information to the individual feature local controllers.

The central computer 336 may include multiple hardware components that perform distinct control functions, or may comprise a single multi-function computer to perform some or all of the various control functions. The central computer may, for example, include a combination of a an Encoder Signal Reference Simulator (ESRS) manufactured by Rockwell International and a programmable logic controller such as a 1785-L40C PLC-5 manufactured by Rockwell to perform the global motion/drive control function 916. Alternatively, the central computer may include a programmable logic controller ("PLC") to perform the global logic control function 918, and a personal computer ("PC") to perform the global motion/drive control function 916. In this embodiment, for example, either the PLC or the PC may perform the global operator interface function 921. Alternatively, the central computer 336 may include a single multi-function computer system such as a personal computer, mainframe, microcomputer, mini-computer, etc. that performs each of the global motion, drive and logic control functions, and the global data collection and reporting function.

In addition, the various pieces of hardware that may comprise the central computer 336, may be housed in a single panel or may include multiple components in different panels that are located adjacent to each other or distributed throughout the manufacturing system. In one embodiment, for example, the panel that houses a central motion/drive controller may be located close to a master drive motor or a mechanical line shaft if one of these methods of creating a master motion/drive reference signal is used, while the panel that houses the central logic controller may be located in another panel somewhere else along the flexible manufacturing system. The central computer 336 may be housed in one or more control panels such as the central computer control panel 914 shown in FIG. 55. The central computer control panel 914 that houses the central computer 336 may be located on the panel support structure 240 such as shown in FIG. 21 or in another area of the flexible manufacturing system.

Each feature section may include one or more modules and a feature local controller. A feature local controller may include a feature local motion/drive controller and/or a feature local logic controller. FIG. 54, for example, shows a simplified view of one embodiment of a flexible manufacturing system of the present invention including a control system 1090 for two feature sections 1078 and 1080. For ease of illustration, FIG. 54 depicts only a central computer 336 and two feature sections 1078 and 1080. A flexible manufacturing system of the present invention, however, may include one, two, three or more feature sections. In the flexible manufacturing system shown in FIG. 54, the first feature section 1078 includes first and second first feature modules 1082 and 1084, respectively, and the second feature section 1080 includes one second feature module 1086. In this embodiment, the control system 1090 preferably includes a central computer 336, and first feature and second feature local controllers 1108 and 1110 for controlling the operational units of the first and second feature sections 1078 and 1080, respectively. The first feature local controller 1108 may include a first feature local motion/drive controller 1062 and/or a first feature local logic controller 1066. The second feature local controller 1110 may include a second feature local motion/drive controller 1064 and/or a second feature local logic controller 1068. The first feature local controller 1108 and/or the second feature local controller 1110 may also include a local operator interface such as 1070 and 1072.

Each module may comprise one or more operational unit(s): the first and second modules 1082 and 1084 of the first feature section 1078 may comprise a first feature section first operational unit 1092 and a first feature section second operational unit 1094, and the module 1086 of the second feature section 1080 may comprise a second feature section operational unit 1096.

Each operational unit may comprise one or more motor(s) and/or one or more control device(s). (The term "control device" as used in this application refers to devices such as a solenoid, a photo eye, a proximity switch, a temperature sensor, a relay, a small AC motor for driving a web tracking mechanism, or any other control device known in the art.)

The first feature section operational units 1092 and 1094 may comprise first feature section motors 1057 and 1058, and first feature section control devices 1073 and 1074. Similarly, the second feature section operational unit 1096 may comprise a second feature section motor 1060 and a second feature section control device 1076.

The first and second feature local controllers 1108 and 1110 may be integrated into a network with the central computer 336. The network may include, for example, two sub-networks: a motion/drive control sub-network 1126 by which the central motion/drive controller 916 is connected via links 1128 and 1142 to the first feature and second feature local motion/drive controllers 1062 and 1064, respectively, and a logic control sub-network 1124 by which the central logic controller 928 is connected via links 1052 and 1056 to the first feature and second feature local logic controllers 1066 and 1068, respectively. The information transmitted over the motion/drive control sub-network 1126 may, for example, represent the distances that the master drive encoder or a virtual master drive encoder has moved. Information transmitted over the logic control sub-network 1124 may, for example, include machine set points, product quality information, machine status and run condition, etc.

As described above, a feature section includes one or more operational units. Each operational unit may include at least one motor and/or at least one logical device. In one embodiment of the present invention, the motor may be an independently-driven servo motor. In this embodiment, the velocity and position of operational units need not be phased by a common mechanical line shaft. There may be no mechanical coupling between the operational units, and the velocity and position of the operational units may be synchronized by the feature local controller with respect to a common positional and/or velocity reference. The source of the common reference may be any of the master motion/drive references described above.

The motion/drive controllers may be connected to one or more servo motor(s). In the embodiment shown in FIG. 54, for example, the first feature local motion/drive controller 1062 may be connected with the servo motors 1057 and 1058 of the first and second modules 1082 and 1084 of the first feature section 1078 by power and feedback cables 1118 and 1120, and, similarly, the second feature local motion/drive controller 1064 may be connected with the servo motor 1060 located in the module 1086 of the second feature section 1080 by power and feedback cables 1122.

A motor motion/drive control system may include, for example, one or more of the following component(s): a feature section motion/drive controller; an electric motor such as a servo motor, a dc motor an ac vector drive motor, etc.; and/or an electric motor position feedback sensor such as an encoder or a resolver. The feature section motion/drive controllers 1062 and 1064 may include one or more programmable motion/drive controllers and one or more power converter/amplifier. A programmable motion/drive controller may control a motor using a specific control routine or configuration that includes a set of preprogrammed or operator defined control steps or set points. The control steps or configuration may, for example, include instructions on the relative velocity and/or position of one or more motors to a master reference signal. A position feedback sensor for the motor shaft may also be connected to the programmable motion/drive controller. The programmable motion/drive controller may calculate the position of the servo motor shaft relative to a master reference signal using the feedback sensor, and follow preprogrammed instructions to adjust the velocity and/or position of the motor to match the relative velocity and position of the master reference signal. In one embodiment, for example, the master reference signal may include a frequency, amplitude and/or an angle to represent the reference velocity and position for the flexible manufacturing system. A motor power converter/amplifier may control the amount of electrical current applied to the motor to maintain its relative position to the master reference signal. The amount of electrical current required may be determined by the motion/drive controller and may be based on the amount of error calculated between the motor's shaft and the relative velocity and/or position of the master reference. The motion/drive controller may also transmit, via an analog or digital network, to the logic controller information such as status codes, error codes, velocity and position.

In order to assist in line changeovers, product size variations, etc., the programmable motion/drive controller may have several alternative routines from which a line operator may choose to configure the line to assemble a particular product. Alternatively, the control routines may use operator-defined set points to control the operation of various motors in a feature section. In a further embodiment, if the programmable motion/drive controller may be connected to a network as shown in FIG. 54, and the control routines may be replaced, deleted or modified over the network. The network, in one embodiment, may be an ethernet, a Control Net™ product of Rockwell International), a combination of the two, or any other type of network known in the art.

The motor may be mechanically connected to one or more operational unit(s) and electrically connected to the motor power converter/amplifier. The mechanical interface between the motor and the operational unit may be a gear or a pulley set and/or a combination, or it may be a direct link. Operational units that are required to be pitched to a product, i.e., phased once, twice, etc. per product, on the production line may have motors that are configured as "pitched" motor systems to rotate at a velocity that is synchronized with the product pitch. In one embodiment, an operator may synchronize the velocity of the motor with the product pitch by selecting the number of encoder pulses of a line shaft or a master drive motor on the converting line or the number of virtual encoder pulses transmitted over the motion/drive control network that represent a single product pitch at the operator interface. The local motion/drive control function may synchronize the operation of a pitched operational unit to a single product length. For example, a single revolution or linear movement of the pitched operational unit may correspond to an integer number of product lengths, or an integer number of revolutions or linear movements of the pitched operational unit may correspond to a single product length. In one embodiment, a feature local controller may synchronize the rotation or linear movement of the pitched operational unit to a single product length by multiplying the set number of encoder or virtual encoder pulses by the gear ratio for the particular motor that drives that operational unit. The gear ratio is dependent upon the mechanical connection between the motor and the operational unit, and the number of products that may be produced by one rotation or linear movement of the operational unit. The gear ratio may be preprogrammed or set by an operator for a particular motor in a feature section. In an alternative embodiment, the rotational or linear velocity of the operational unit may be synchronized with the product pitch by preprogramming, or by the operator selecting at the operator interface, the number of products that will be produced in a given time frame, e.g., 100 diapers per minute. Operational units that are not required to be pitched to the product may have motors that are mechanically coupled to the non-pitched operational units and may be configured as non-pitched motor systems. The non-pitched operational unit may follow the relative velocity of the master reference. The operator may have the ability to change or adjust the motor velocity of the non-pitched operational unit to compensate for various changes in raw materials and/or a product size, or this may be done through programming.

An independently-driven servo motor allows for more rapid changes in motor velocity and position versus the remainder of the line because software control of the servo motor may be more rapidly changed out than traditional mechanical linkages, gears, belt drives, etc. Using digitally controlled servo motors may also allow for more accuracy in product making because they may provide a higher degree of synchronization and position control over traditional line shaft and/or belt drives, especially in a long drive train. Furthermore, digitally controlled servo motors may also allow for "push button" changeovers that allow an operator to select a product from pre-configured program set points for one or more of the logic and motion/drive control systems to direct the motion/drive of one or more of the servo motors to automatically make the desired product.

As described above, an operational unit may include one or more logical devices. In one embodiment, the local logic control functions may be housed in a feature local logic controller that directly controls the operation of the logical devices for that feature and synchronizes or coordinates the operation of those logical devices with the rest of the flexible manufacturing system. The feature local logic controller may synchronize or coordinate the operation of the local logical devices by using a master logic reference signal that is generated by the central logic controller and transmitted over a network, such as the logic control sub-network 1124, to the feature local logic controller.

The feature local logic controllers may be connected with one or more control devices and/or one or more operator interfaces in a remote local network. The first feature local logic controller 1066 may, for example, be connected with the first feature control devices 1073 and 1074 located in the first and second modules 1082 and 1084 of the first feature section 1078 and with a first feature operator interface 1070 by the first feature remote local network links 1138 and 1140. Similarly, the second feature local logic controller 1068 may, for example, be connected with the second feature control device 1076 located in module 1086 of the second feature section 1080 and with a second feature operator interface 1072 by the second feature remote local network links 1134 and 1136. The feature remote local networks may be a digital internal control network for a feature section. This feature remote local network may originate at a feature local logic controller and connect the operational unit control devices with the logic controller via remote input and output electronic modules. The first feature local logic controller 1066, for example, may be connected to the first feature operational unit control devices 1073 and 1074 via the first feature remote local network 1146. The second feature local logic controller 1068, for example, may be connected to the second feature operational unit control device 1076 via the second feature remote local network 1148. The internal network may also connect the feature local logic controller with its corresponding operator interface such as the first and second feature local logic controllers 1066 and 1068 with the first and second feature operator interfaces 1070 and 1072, respectively. Signals transmitted over a feature remote local network may include, for example, status from control devices located in one or more of the modules included in a feature section.

An example of a local control system including both a local motion/drive control function and a local logic control function is the adhesive control system shown in FIG. 59. A feature section 1202 of the present invention may include one or more adhesive applicators 380 housed in a module 300 of the feature section 1202. The adhesive applicator 380 may be of any type used in the art and may receive adhesive from an adhesive tank 384 via a pump 386, a supply hose 388, a remote meter 390, and a feature adhesive supply hose 392. The remote meter 390 may be driven by a servo motor 1206, which may be controlled by the feature local motion/drive controller 962. The feature local motion/drive controller 962 may include multiple, independent single axis programmable motion/drive controllers 963 such as 1398-DDM-009 controllers manufactured by Rockwell International for each motor that is to be controlled, and/or one or more multiple axis programmable motion/drive controllers such as a 1394-SJT10-T-RL controllers manufactured by Rockwell International that may control multiple motors. The feature local motion/drive controller 962 may control the servo motor 1206 via a drive and feedback control cable 1208. A feature adhesive supply hose 392 may supply the adhesive from the remote meter 390 to the adhesive applicator 380. The temperature of the adhesive in the remote meter 390, the feature adhesive supply hose 392 and the adhesive applicator 380 may be controlled by the feature local logic controller 934 via a power and feedback cable 1210, which may be connected to the local logic controller 934 through an adhesive junction box 382 and remote local network link 1214. The adhesive junction box 382 may have terminal connectors for an electrical power supply and input/output devices for temperature control/feedback signals from the remote meter 390, the feature adhesive supply hose 392 and the adhesive applicator 380. The adhesive junction box 382 may be connected to interface connectors 968 via a power supply cable 1212, and to the feature local logic controller 934 via a remote local network link 1214 to provide a temperature feedback signal to the feature local logic controller 934. The feature local logic controller 934 may be connected, such as by an adhesive stitching control cable 1216, to an electrical-to-pneumatic converter 1218 located in the module 300. The converter 1218 may be connected to the adhesive applicator 380 via compressed air tubing 1220. The converter 1218 may receive compressed air 1222 and provide on/off supply of compressed air to the adhesive applicator 380 for starting and stopping the adhesive flow through the adhesive applicator 380.

In one particular embodiment of the present invention, a standard adhesive control panel 960 may be configured containing standard hardware and/or software for controlling the operation of adhesive applicators throughout the flexible manufacturing system. A standard adhesive control panel 960, for example, may be used for each feature section of the flexible manufacturing system of the present invention that includes an adhesive applicator. The feature-specific hardware and/or software required for controlling a particular adhesive applicator such as adhesive applicator 380 may be included with the feature local logic controller 934, and/or may be added to the standard adhesive control panel 960. Utilizing standard adhesive panels may allow adhesive operational units to be added or removed from a feature section without reconfiguring the feature local controller of the feature section. In this embodiment, for example, the logic controller 934 may be connected to a logic control panel input and output section 966 located in the adhesive control panel 960 via a remote local network link 1224. A standard adhesive control panel 960 is shown schematically in FIG. 58. The adhesive control panel 960 may have a standard design for controlling multiple remote meters by including multiple programmable motion/drive controller and motor power converter/amplifier pairs 962.

The tank control function may be performed by a separate local controller dedicated to controlling one or more adhesive tanks, one or more of the feature local controllers or by the central computer. The tank control function may control the temperature of the adhesive in the tank 384 and in the supply hose 388 in addition to the rate of the adhesive supplied to the remote meter 390 located in the module 300 of the feature section 1202. The adhesive tank 384 may include multiple adhesive chambers that each include at least one pump and may contain different types of adhesives.

A feature local controller may include at least a logic controller and/or a motion/drive controller and/or other elements such as one or more safety circuits and/or one or more power distribution systems. As shown in FIG. 56, for example, a control panel 370 may include a motion/drive controller 932; a logic controller 934; control relays 936; safety relay 938; a programmable cam switch 940, dedicated wire termination points 942; feature interface connectors 944; a logic interface panel 946; power distribution circuit breakers 948; motion/drive controller contactors 950; AC motor contactors 952; and 25VDC power supplies 954. A feature local controller may be housed by one or more control panels or by one or more of the modules of the feature section.

Figure 23A:
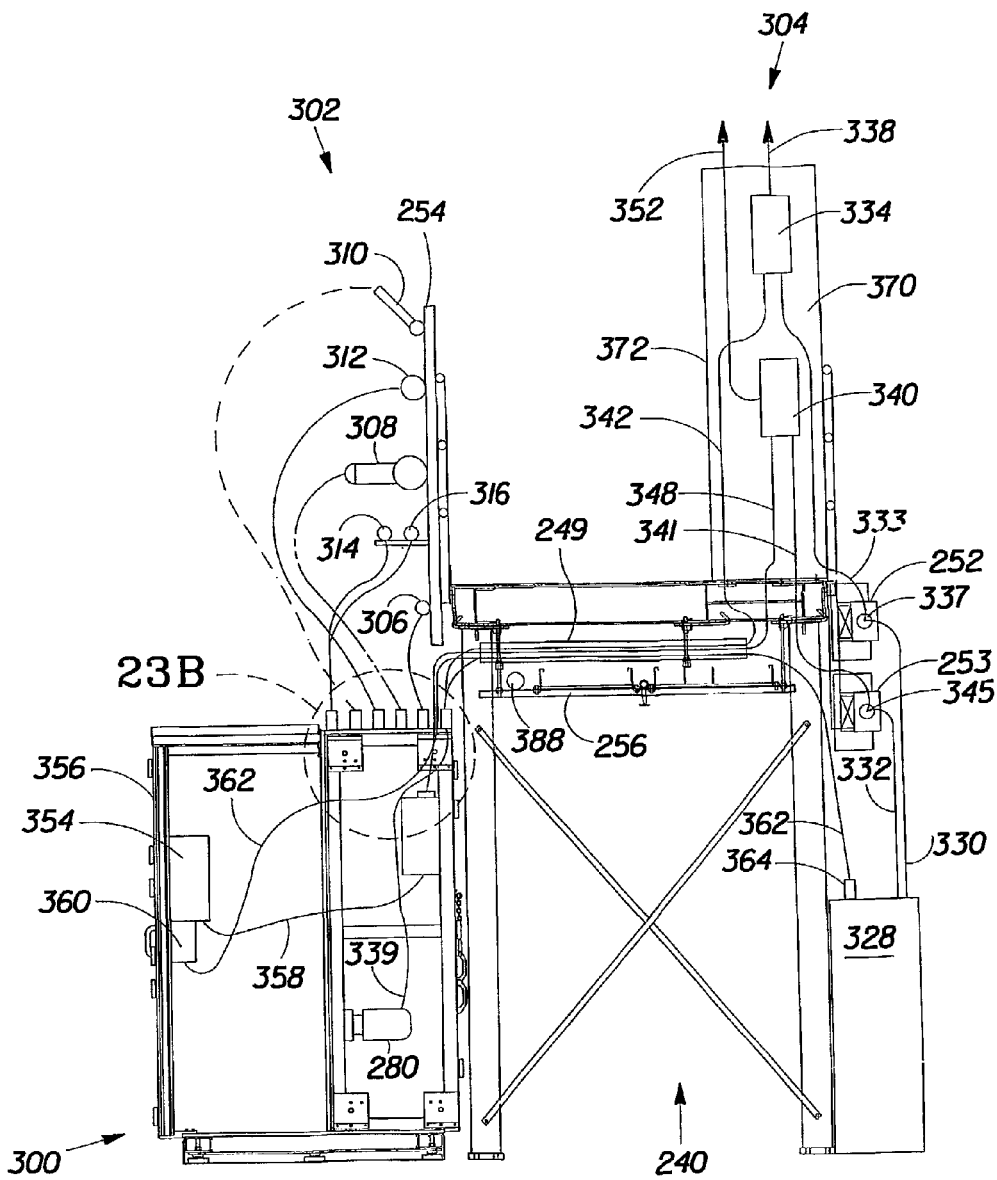
FIG. 23A is a simplified side view of a module connected to electric power and fluid utilities.

In one embodiment of the present invention, a feature local controller may be housed in one or more standard control panels such as described above with respect to the central computer 336. A standard control panel that houses a feature local controller may be located nearby or adjacent to the module(s) of the feature section that the feature local controller controls. As shown in FIG. 23A, for example, a standard control panel 370 may be located on the panel support structure 240 adjacent to the module 300 that it controls. In the event that the module(s) of a feature section are replaced by another feature section, the standard control panel 370 may be reconfigured to operate as the feature local controller for the new feature section and to control the module(s) of the new feature section.

In one embodiment, the flexible manufacturing system of the present invention may include standard main control panels 371 as shown in FIGS. 21 and 56 and standard auxiliary control panels 374 (standard auxiliary control panels 374E and 374F are shown in FIG. 21). Each of the standard control panels may be limited in space so that it may only house control hardware for a fixed number of electric motors, logical devices, etc. In this embodiment, when a feature section consists of more than the fixed number of electric motors, logical devices, etc. that a standard main control panel 371 may house, one or more standard auxiliary control panels 374 may also be used. In addition, a standard adhesive control panel 960, such as shown in FIGS. 21 and 58, and described above, may be used to house the hardware for a particular feature local controller that controls an adhesive system in the feature section. Alternatively, additional standard control panels may be configured to contain the hardware that controls other subsystems of a feature section such as motion/drive or logic control aspects of the feature local controllers.

FIG. 21 shows, for example, a portion of an exemplary flexible manufacturing system of the present invention in which the feature local controllers are housed in standard control panels on a panel support structure 240 adjacent to the modules of the feature sections that the feature local controllers control. The cuff feature section A is shown adjacent to a standard main control panel 371A and a standard adhesive control panel 960A that together comprise the feature local controller for the cuff feature section A. The side panel feature section C is shown adjacent to a standard main control panel 371C and a standard adhesive control panel 960C that together comprise the feature local controller for the side panel feature section C. Next, the landing zone feature section D is shown adjacent to a standard main control panel 371D and a standard adhesive control panel 960D that together comprise the feature local controller for the landing zone feature section D. The fastening feature section E is shown adjacent to a standard main control panel 371E, a standard auxiliary control panel 374E and a standard adhesive control panel 960E that together comprise the feature local controller for the fastening feature section E. Finally, the fold and form feature section F is shown adjacent to a standard main control panel 371F and a standard auxiliary control panel 374F that together comprise the feature local controller for the fold and form feature section F.

Some modules of the flexible manufacturing system of the present invention, however, may perform a collection of process steps that are not directly related to the production of a product feature. The chassis combining in-feed module 622 and the chassis combining module 624, collectively identified as section B of the flexible manufacturing system, for example, do not comprise a feature section for the purposes of the present invention. The operational units in these modules combine webs that form the carrier for the manufacturing line, but do not form a particular product feature. Rather, the operational units within these modules comprise a functional operation of combining multiple webs. In this example, multiple operational units that are not part of a feature section may be located in one portion of the flexible manufacturing system and commonly controlled by one or more local controllers such as the local controllers located in the standard main control panel 371B and standard adhesive control panel 960B for the chassis combining in-feed module 622 and the chassis combining module 624. Alternatively, operational units or functional operations that do not form a feature section may be housed in the modules of a feature section that has space. For example, a side notch device 778 that removes a portion of the web and is described below may be housed in one of the modules of the fastening feature section E and may be controlled by the feature local controller of the fastening feature section E that is housed in standard main control panel 371E, standard auxiliary control panel 374E and standard adhesive control panel 960E.

The term "operator interface" as used in this application refers to a microprocessor-based system that may allow an operator to input data and receive data from a central computer or from a local controller. A flexible manufacturing system of the present invention may include a central operator interface that may be connected to the central computer and one or more local operator interfaces that may be connected to one or more feature local controllers. The central operator interface may obtain information from the central logic controller in the central computer and may integrate the line data from one or more feature local controllers and display the data for the operator. The central operator interface may also distribute the data input from the operator to one or more feature local controllers. An operator interface may also be the origin of one or more machine set points such as motor parameter set points, glue temperatures, and programmable cam limits. The operator interface may also hold a database for other displays on the line, such as electronic annunciation systems.

Figure 52:
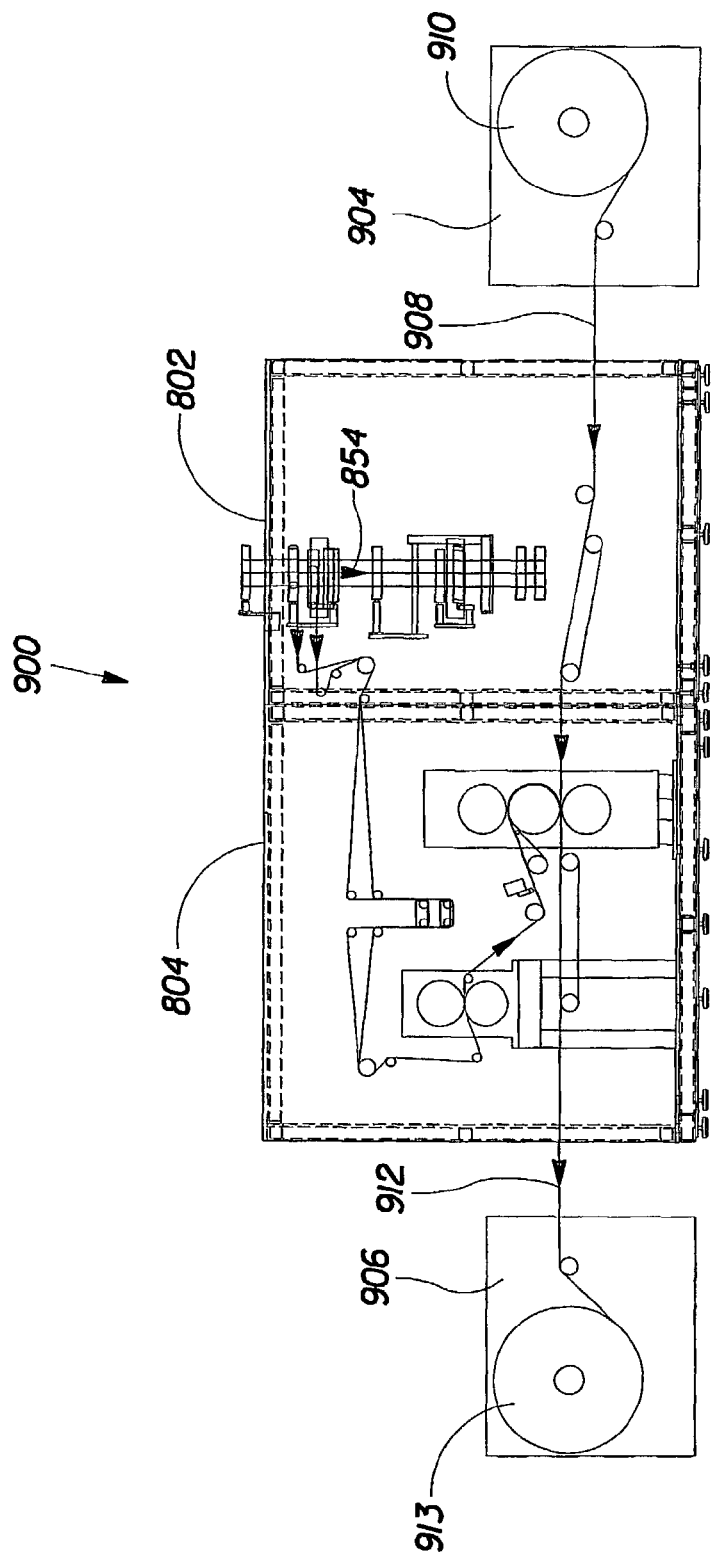
FIG. 52 is a simplified front view from the operator side of a standalone test stand operation.

The central operator interface 920 shown in FIG. 54 and the first feature and second feature operator interfaces 1070 and 1072, respectively, may display for the operator the messages concerning malfunctioning of the manufacturing system such as alarm messages. Some examples of alarm messages may be a number of product rejects, a tissue break, an above tolerance torque on a servo motor, a misalignment of a component, an above tolerance temperature, etc. The alarm messages for a feature section may be displayed on a feature operator interface and/or on a central operator interface. As shown in FIG. 52, for example, the alarm messages for the first feature section 1078 may be displayed on the first feature operator interface 1070, and the alarm messages for the second feature section 1080 may be displayed on the second operator interface 1072. However, the central operator interface 1072 may display the alarm messages related to both feature sections 1078 and 1080. In one embodiment, the alarm messages may be stored in the central logic controller 928 of the central computer 336.

The embodiment shown in FIG. 54, for example, may utilize the following commercial hardware: the master motion/drive reference 924 may be an Encoder Signal Reference Simulator (ESRS) manufactured by Rockwell International; the motion/drive control signal converter transmitter 926 may be an ALEC-4100 Axislink Encoder Converter manufactured by Rockwell; the central logic controller 1114 may be 1785-L40C PLC-5 manufactured by Rockwell; the motors 1073, 1074 and 1076 may be 1326 Servo Motors manufactured by Rockwell; the motion/drive controllers 1062 and 1064 may be 1394-SJT10-T-RL controllers manufactured by Rockwell; the feature local logic controllers 1066 and 1068 may be 1785-L40C15PLC-5 Processors manufactured by Rockwell; the feature operator interfaces 1070 and 1072 may be a 1585THX+1242 manufactured by IDT Cutler Hammer of Ohio; the central main operator interface 920 may be a D735SVPR64DWNT manufactured by IDT Cutler Hammer of Ohio.

Figure 53:
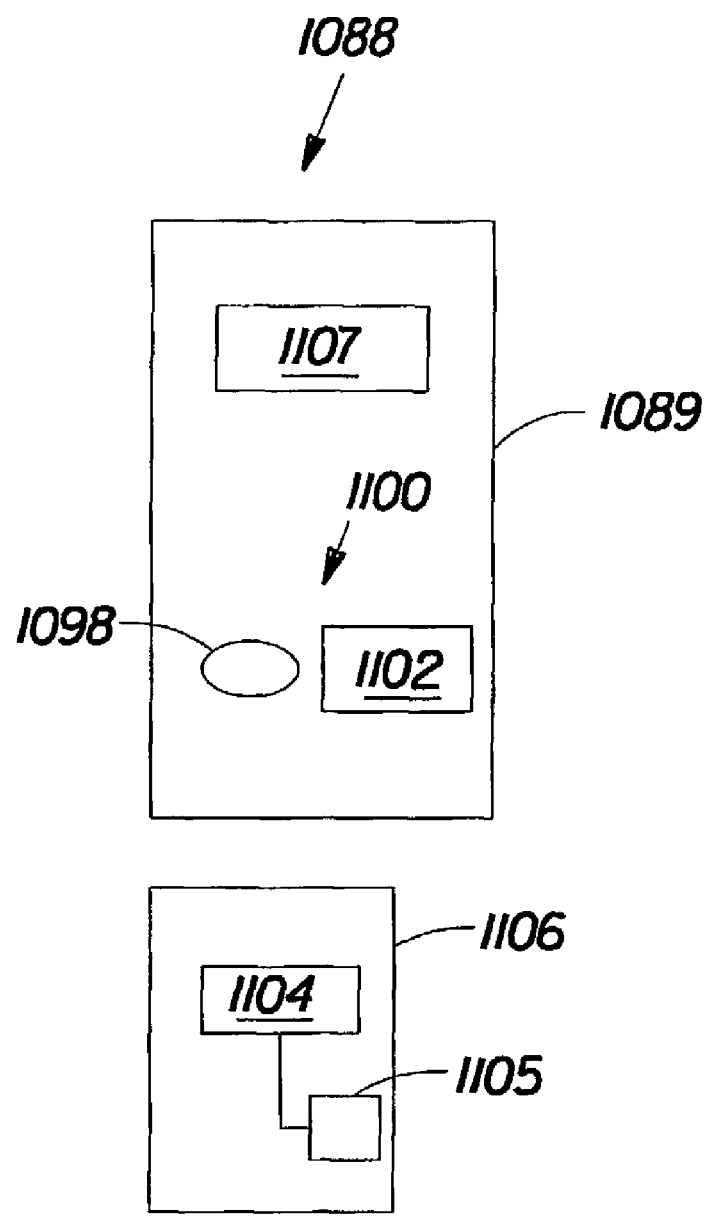
FIG. 53 is a block diagram of a standalone operation or of a feature section that may be added to a manufacturing line.

FIG. 53 illustrates a feature section 1088. The feature section 1088 may be adapted to be an addition to the manufacturing system and/or a substitution of one or more feature sections. The feature section 1088 may be capable of producing a new product feature or a modified product feature. Further, the feature section 1088 may be capable of producing an alternative product feature to one produced by the feature section that is being replaced. In this embodiment, the feature section 1088 may be interchanged with another feature section in order to allow the line to produce a different product or a different variation of a product (e.g., a different size).

FIG. 53 shows that feature section 1088 may include at least one module 1089 and at least one feature local controller 1106. Further, the module 1089 may include at least one operational unit 1100 which may include at least one control device 1102 and/or at least one motor 1098. The feature local controller 1106 may also include at least one motion/drive controller 1104 and at least one logic controller 1105. Still further, the feature section 1088 may include at least one feature operator interface 1107.

When a feature section is removed from or added to the manufacturing system, the alarm files concerning the removed or added feature section may be removed from or added to the central computer 336. See e.g., FIG. 54.

Alternatively, the central computer may contain the alarm files for various feature sections and when the central computer is informed, such as by an operator input, a software flag from the feature local controller or stored within the central computer itself, the central computer may look up the correct alarm file corresponding to that feature section. The term "updating alarm files" may include both the removal and/or the update of the alarm files, or may include informing the central computer of the feature section that is currently connected to the manufacturing system. The alarm files may be updated manually or automatically. Manually updating alarm files may involve, for example, connecting a personal computer 1050 (see e.g., FIG. 54), having logic control software, to the logic control sub-network link 1052 for removing the alarm files stored in the central logic controller 928 or for adding new alarm files into the central logic controller 928. Automatically updating alarm files may involve having the central logic controller 928 read alarm files in every feature local controller of the manufacturing system via the logic control sub-network links 1052 and 1056 after an initialization signal has been provided by the operator from the main operator interface 920 (see e.g., FIG. 54) or from the feature operator interface 1107 (See e.g., FIG. 53).

Panel Support Structure

FIGS. 21, 23A, 24 and 25 show a panel support structure 240 that may support a fluid utility system 302, an electrical power system 304, standard control panels 370, standard main control panels 371, standard auxiliary control panels 374, standard adhesive control panels 960, source material, etc. to provide more operating floor space and improved access to the converting line. The panel support structure 240 may be about the same length as the manufacturing line, and may be located immediately adjacent to the drive side of the line. The panel support structure 240 may be prefabricated in lengths that can be easily shipped to a plant site in standard shipping containers and assembled quickly on the plant site by using commercial hardware as shown in FIGS. 24–29. The prefabricated sections may include one or more platform 242, support columns 244, stairs 246, safety hand rails 248, wireways 249 and 256, two power distribution bus ducts 252 and 253, utility header supports 254, and cross braces 258. The platforms 242 may be of standard lengths, such as about 3.5 and/or about 4 meters.

Figure 25:
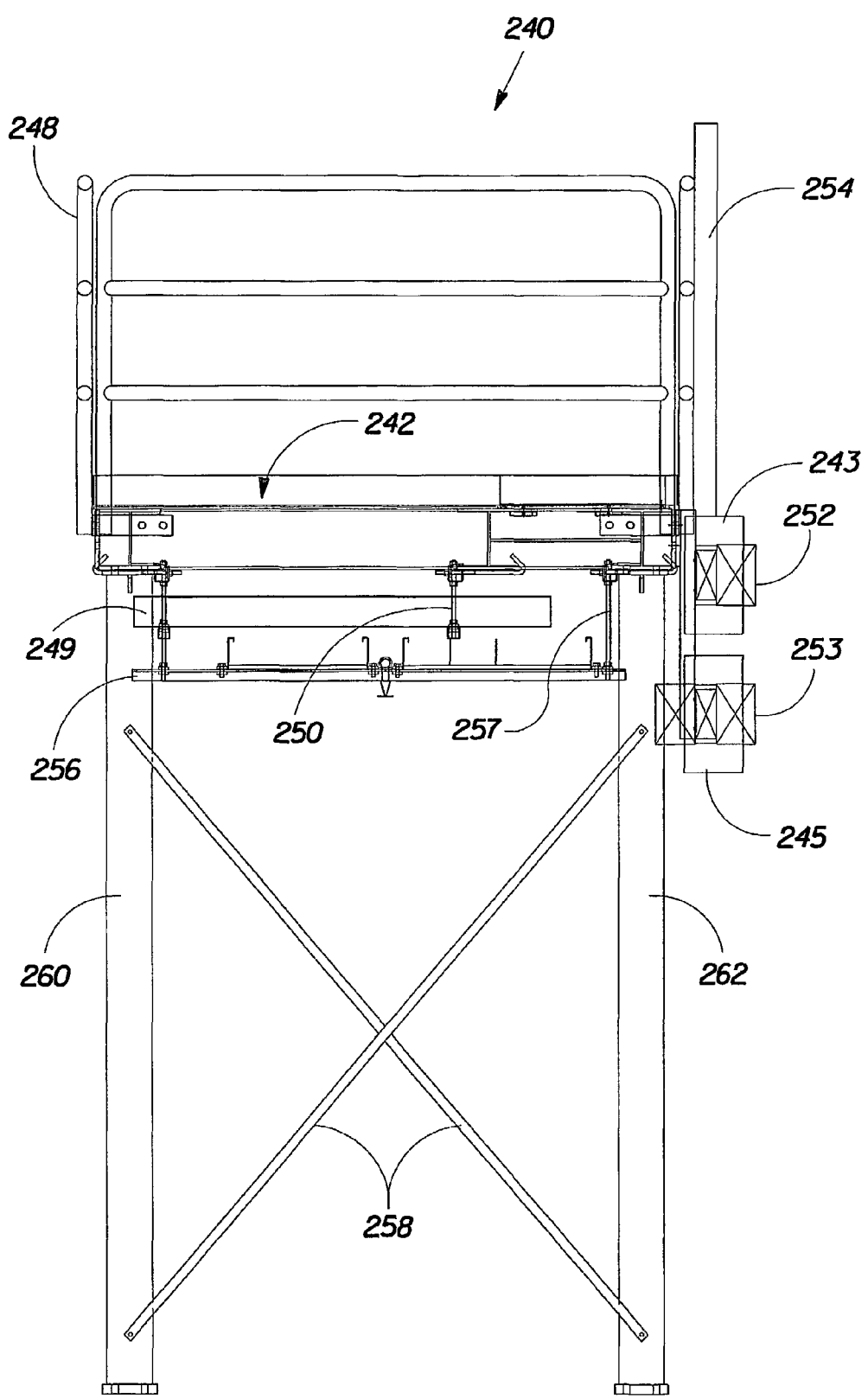
FIG. 25 is a side view of a panel support structure shown in FIG. 24.

There are preferably two rows of columns 260 and 262 supporting the panel support structure 240 as shown in FIG. 25. The row 260 is located along the edge of the panel support structure 240 immediately adjacent to the modules and the row 262 is located along the side distant from the modules. The support columns are preferably of a moveable design and are preferably located adjacent to the connecting line between the modules. This location creates a convenient access to the drive side of the modules by allowing the drive side guard doors 162 and 164 shown in FIG. 15 to be open a full 90 degrees without obstruction. In the event a change such as a product upgrade or product change for the manufacturing line results in a change of a module length, and this results in a column blocking access to one or more modules, it may be desirable to relocate the column to the connecting line location between two modules. To accomplish this quickly, the platform beam 264 to which the support column 244 (FIG. 28) attaches is preferably pre-drilled with a series of holes that allow it to be reattached without further modification to the platform beam 264 or the column 244. The hole pattern may be repeated incrementally in a distance equal to the incremental difference between different size modules used in the converting line. For example, if the modules of a particular converting line are 1.0, 1.5, 2.0 and 2.5 meters in width, the hole patterns may be repeated every 0.5 meters along the panel support structure.

Control panels, such as the standard main control panels 370, the standard auxiliary control panels 374 and the standard adhesive panels 960, may be located on the panel support structure 240 and may be attached to the panel support structure 240 with clamps that eliminate a need to drill holes in the panel support structure 240 and allow easy installation and removal of the panels.

Figure 23B:
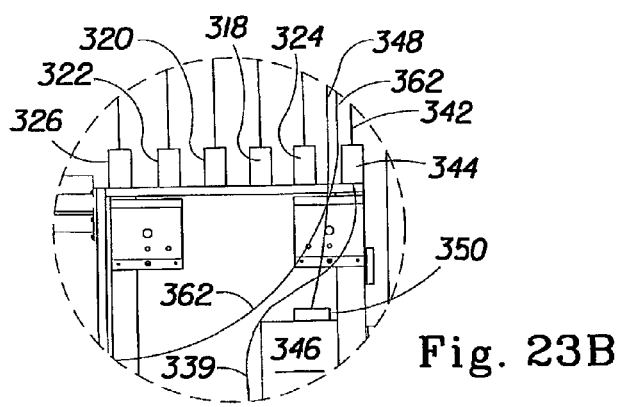
FIG. 23 B is an enlarged view of an area 23B shown in FIG. 23A.
Figure 24:
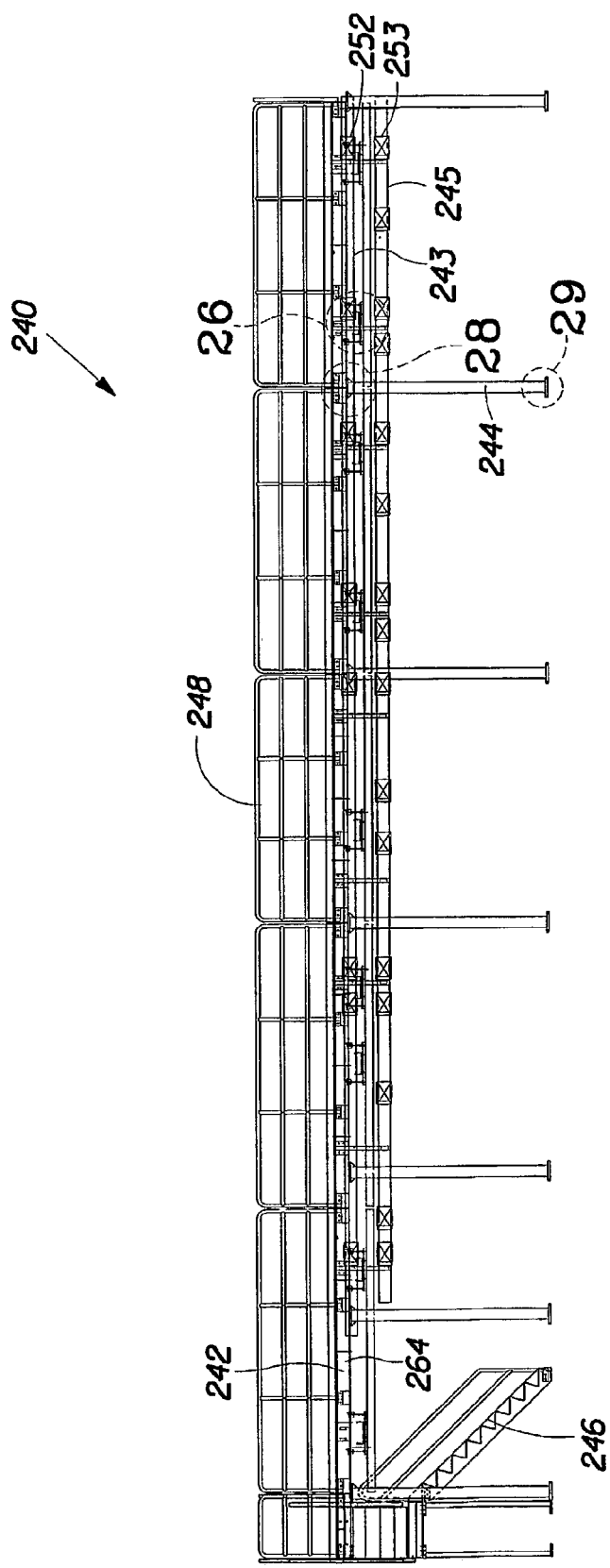
FIG. 24 is a simplified front view of the panel support structure shown in FIGS. 21 and 23A.

As shown in FIGS. 23A and 23B, the utility header supports 254 may be used to support piping for compressed air, vacuum, glycol, etc. directed to parts of the manufacturing line where they are needed. Having them supported independently from the modules and from the control panels enhances the ability to make rapid changes of the modules of the manufacturing line.

Figure 26:
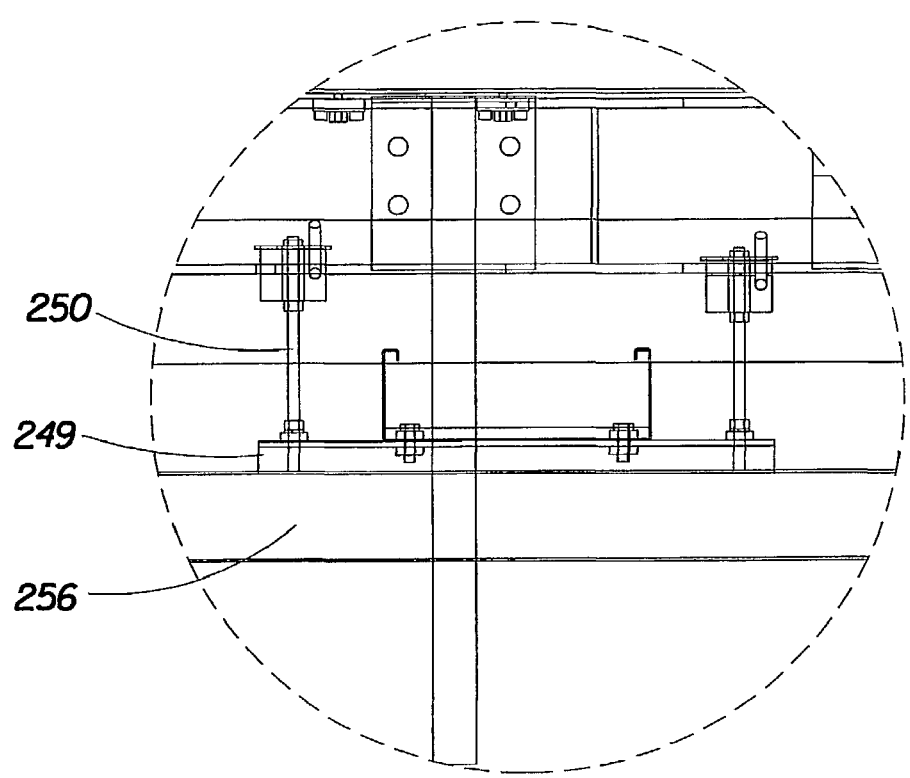
FIG. 26 is an enlarged view of area 26 shown in FIG. 25.
Figure 27:
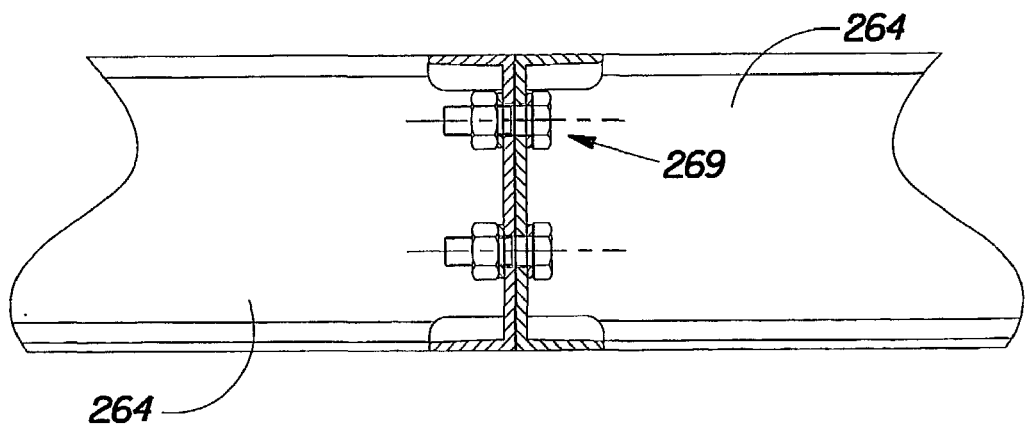
FIG. 27 is an enlarged view of a connection of two platform beams of the panel support structure shown in FIG. 24.
Figure 28:
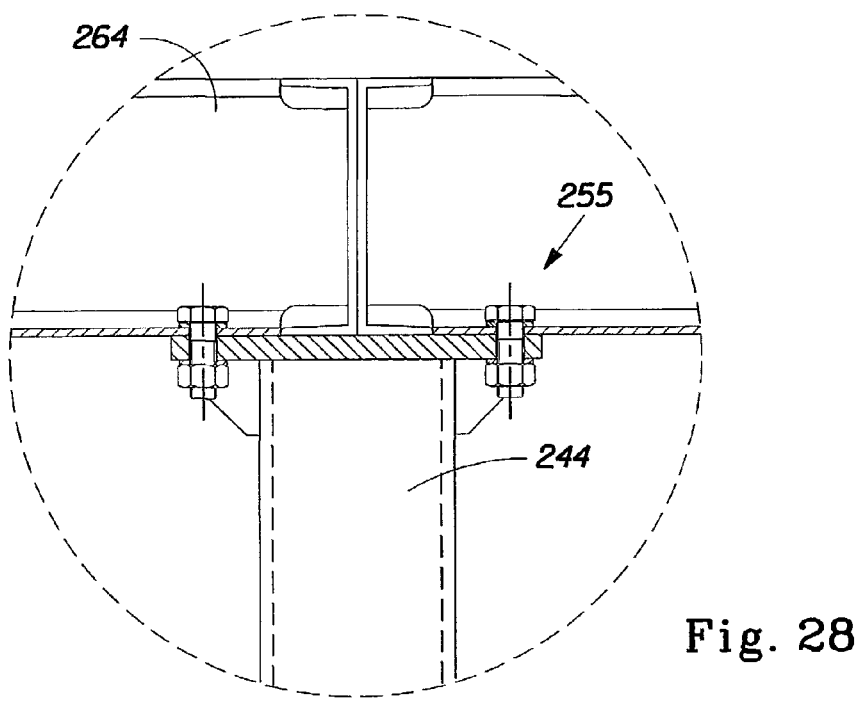
FIG. 28 is an enlarged view of area 28 shown in FIG. 24.
Figure 29:
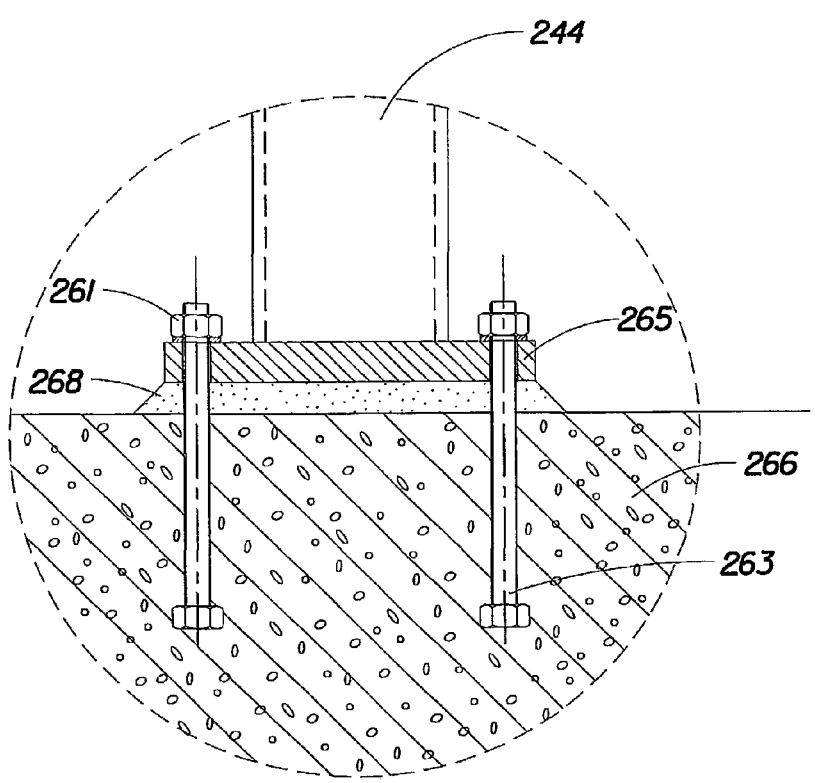
FIG. 29 is an enlarged view of area 29 shown in FIG. 24.

The wireways 249 and 256 may be used to support electrical control cables, power cables, adhesive hoses, etc. that may be run to a particular module as shown in FIGS. 23A, 25 and 26. This approach may save time during the initial installation and whenever a module is removed, added or replaced for an upgrade because operators are not required to disturb or re-pull unrelated cables or hoses.

Multiple power distribution buses, such as the motion power distribution bus 252 and the auxiliary power distribution bus 253, may be mounted independently to the panel support structure 240 These buses may be located near the base of the control panels and run parallel to the manufacturing line.

FIG. 23A illustrates the positioning of a module 300 in relation to the panel support structure 240 and also connections of the module 300 to a fluid utility system 302 and to an electric power system 304. The module 300 may be located adjacent to the panel support structure 240 under a header support 254. The header support 254 is attached to the panel support structure 240 and supports the fluid utility system 302 which may include headers attached to the header support 254 such as the following: a compressed air header 306, a low vacuum header 308, a house cleaning vacuum header 310, a high vacuum header 312, a glycol supply header 314 and a glycol return header 316. The headers may include separate sections of headers connected together to form a continuous header system generally along the full length of the manufacturing line. The headers may be connected via pipe, ducts, hoses or tubes (also called "drops") to quick disconnects located immediately above the module 300 such as shown in FIGS. 23A and 23B. The quick disconnects may include a compressed air quick disconnect 324, a low vacuum quick disconnect 318, a house cleaning vacuum quick disconnect 322, a high vacuum quick disconnect 320, and two glycol quick disconnects 326. The quick disconnects may be operated without tools and shorten the time needed to connect and disconnect the utilities. To minimize the number of connections, it is preferable to have no more than one entry per utility for each module. From that entry, a particular fluid utility is routed inside the module to desired destinations. If a particular utility is not required for a particular module, the header of this utility may be closed off such as with an end cap or a valve.

As shown in FIG. 23A, the electrical power may be supplied from a power distribution center 328 to a motion bus 252 and an auxiliary bus 253 via power cables 330 and 332, respectively. Both the motion bus 252 and the auxiliary bus 253 may be attached to the panel support structure 240. The motion bus 252 may be connected to at least one motor 280 located in the module 300 via a motion/drive controller 334. The motion/drive controller 334 may be connected to the motion bus 252 via a motion power cable 333 and a quick disconnect 337 and to the motor 280 via power and feedback cables 339 and 342, which are preferably connected via a quick disconnect 344 located immediately above the module 300. The motion/drive controller 334 may be also connected to a central computer 336 via a control motor cable 338. The auxiliary bus 253 may be connected to at least one logic controller 340 via a logic power cable 341 and a quick disconnect 345. The logic controller 340 may be connected to an electrical junction bus 346 as shown in FIG. 23B by a remote local network cable 348 and a quick disconnect 350. The logic controller 340 may be also connected to the central computer 336 via a logic control network cable 352. An operator interface 354 may be attached to a guard door 356 and connected to the electrical junction box 346 by a remote local network cable 358. A safety lockout switch 360 may be attached to a guard door 356 below the operator interface 354. The safety lockout switch 360 may be connected to the power distribution center 328 via a safety lockout switch cable 362 and a quick disconnect 364. The remote local network cable 348, the safety lockout switch cable 362, and the power and feedback cables 339 and 342 may be extended through a wireway 249, which may be attached to the panel support structure 240. The wireway 249 may be dedicated to the module 300 or to a particular feature section in order to prevent the cables connecting the module 300 or the particular feature section from being intermingled with cables for other modules or feature sections. This approach may save time during the initial installation and whenever a module or feature section is removed, added or replaced in the manufacturing system.

Both the motion controller 334 and the logic controller 340 may be located in a control panel 370 described in more detail below. The control panel 370 may be located above the floor on the panel support structure 240 and adjacent to the module 300. The front 372 of the control panel 370 may be facing the module 300. This layout creates a direct line of sight between an electrician working at the control panel 370 on the panel support structure 240 and an operator on the floor facing the module 300. This may also allow for better communication and may lead to shorter trouble shooting times and a safer operating environment. More than one control panel may be used for a particular module or feature section if necessary to house the required control equipment for that particular module or feature section.

If a module includes at least one adhesive applicator 380, as shown in FIG. 59, for example, then the module may also be provided with an adhesive junction box 382 which may be located on a right top side of the module 300. The adhesive applicator 380 may receive adhesive from an adhesive tank 384 via a pump 386, a supply hose 388, a remote meter applicator 390, and a feature hose 392. A module may include one or more adhesive applicators supplied with one or more adhesives. Control of these adhesive applicators, for example, may be provided by a standard main control panel 371 and a standard adhesive control panel 960. The standard adhesive control panel 960 as well as the standard main control panel 371 may be located on the panel support structure 240 adjacent to the standard main control panel 371.

Safety Lockout

The manufacturing system of this invention includes a safety lockout system for shutting off the electrical power supply from the manufacturing system and for preventing an inadvertent motion of the manufacturing system during the shutdown. The safety lockout system may be any lockout system used in the art of machine control, however, in one particular embodiment of the invention, the safety lockout system may be an 800 ampere rated lockout system from Moeller Electric Company of Bonn, Germany. This safety lockout system enables having a safety disconnect in every module connected to a 24 volts control cable instead of running heavy power cables (for example, 400 volts) between the modules. The latter option would be more costly and take more physical space. The capability of having a power disconnect at every module provides safety and convenience for the operators and maintenance personnel.

Figure 60:
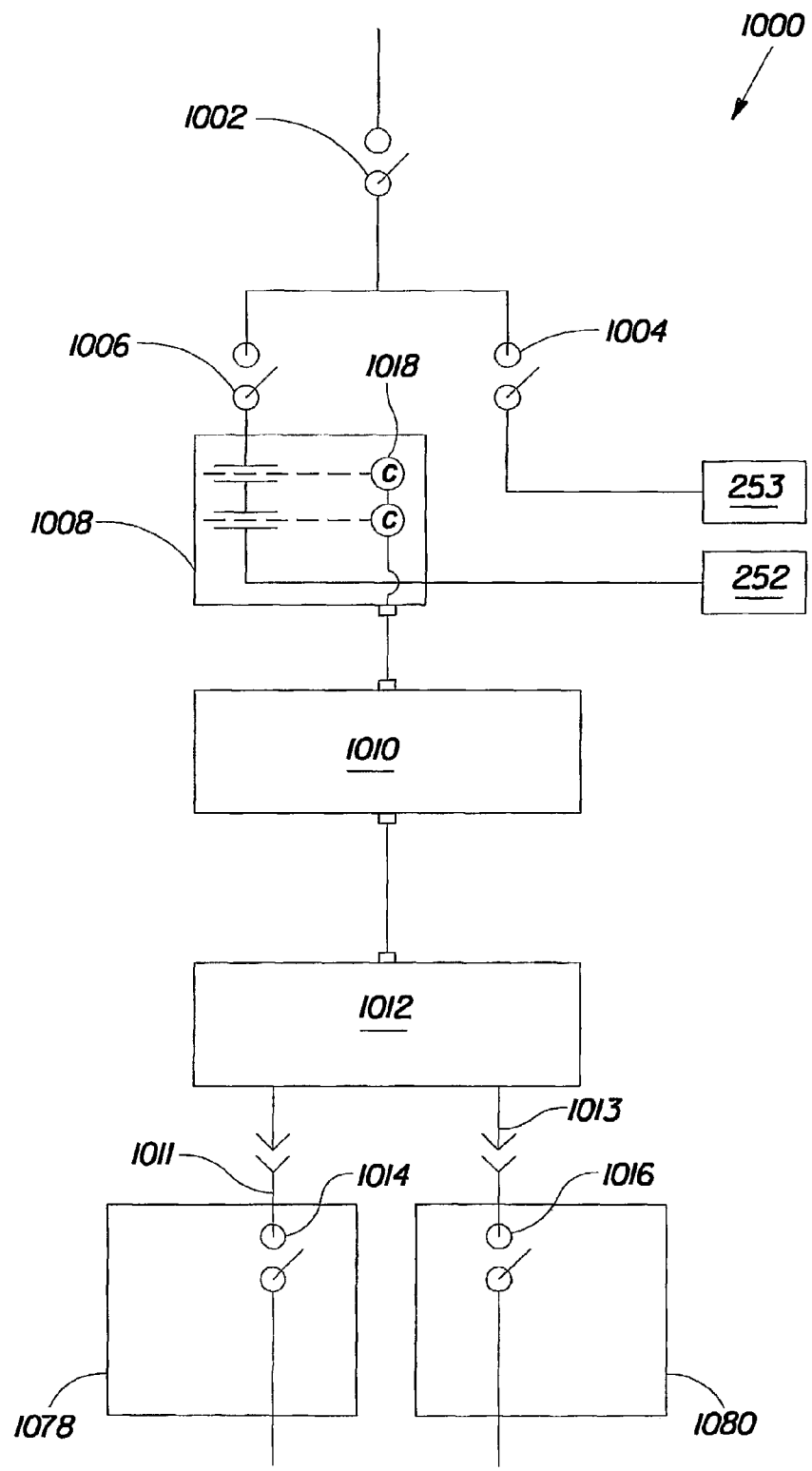
FIG. 60 is a block diagram of a safety lockout system.

FIG. 60 shows a block diagram of one embodiment of a safety lockout system 1000. The safety lockout system 1000 preferably includes a manual main switch 1002, a manual auxiliary bus switch 1004, a manual motion bus switch 1006, motion bus contactor unit 1008, a control unit 1010, a distributor unit 1012, and one or more safety lockout switches 1014, 1016, etc., each providing electric power to a supporting module. The motion bus contactor unit 1008 may provide electric power to a motion bus 252. The power unit 1000 preferably includes contactors 1018 for interrupting the power to the motion bus 252. A manual switch 1004 may serve for interrupting the power to an auxiliary bus 253. Alternatively, the auxiliary bus 253 may include a similar contactor scheme as described above with respect to the motion bus 252. The control unit 1010 may provide a redundant safety monitoring and interlock. The distributor unit 1012 preferably monitors multiple safety switches 1014, 1016, etc. and when one or more of the multiple safety switches is open, the distributor unit 1012 sends a signal to the control unit 1010 informing the control unit 1012 that one or more of the safety switches is open. The control unit 1010, then de-energizes the redundant contactors 1007 to remove power from the motion bus 252.

FIG. 57 shows a preferred embodiment of a power distribution center panel 328 that forms a part of the safety lockout system 1000. The power distribution center panel 328 may include a control unit 1030, a distribution unit 1032, a motion bus contactor unit 1034, a manual motion bus switch 1036, a manual auxiliary bus switch 1038, a manual packing switch 1040, and a manual main switch 1042. Alternatively, the distribution unit 1032 may also be distributed throughout the production line. This may reduce the number and length of cables that need to be run from the individual safety lockout switches 1014, 1016, etc. to the power distribution center panel 328 shown in FIG. 57.

Standalone Operation

FIG. 52 illustrates an example of a two-module feature section being used as a standalone operation 900. The modules may be operated off-line in order to develop product feature upgrades in which the operational units of the feature section may be modified until the product feature is being made as desired. The modules may also be run off-line to test their operation before they are installed in a converting line. Alternatively, the standalone operation 900 may be used as a standalone production center for producing components of a diaper or other disposable article off-line. In this particular example, the back ear in-feed module 802 and the back ear application module 804 are provided with an unwind device 904 and a rewind device 906. The unwind device 904 provides a web material 908 from a reel 910 of the web 908 onto which the back ears 554, as shown in FIG. 31, produced by the modules 802 and 804 from the back ear material 854 may be applied to produce a combined web 912. In one embodiment, the web material 908 may be a product web that includes all the features of a finished disposable article except the feature(s) being assembled by the feature section(s) being run in a standalone mode. The rewind device 906 creates a rear of the combined web 913 including the back ears 554.

The stand-alone operation 900 may be supported by a docking station for supplying power distribution, safety systems, compressed air, vacuum, glycol, adhesive(s) and other utilities as needed. One or more modules of the stand-alone operation 900 may be connected to the docking station similarly as they would have been connected on a manufacturing line and as shown in FIGS. 23A and 23B, and described above.

During standalone mode operation, a feature local controller may control the operation of the operational units in the feature section. The feature local controller may independently synchronize and coordinate the operation of the motors and logical devices in the feature section, or may receive a reference signal from an external source that may be used to simulate the reference signal described above that it would receive in a converting line.

Use of individual modules or feature sections as "test stands" for a portion of a product may eliminate a step from typical product upgrades. For example, a standalone operation including the operational units that form a particular product feature into one feature section that (or a substantially identical feature section that) may ultimately be plugged directly into a production converting line may allow for combining the steps of constructing a high speed test stand that may manufacture a particular product feature being upgraded in isolation at high speeds in order to test the feasibility of high speed manufacturing and constructing a prototype line that is able to make complete prototype products including the particular product feature at high speeds of a typical product upgrade development. Thus, once built and tested, the standalone feature section that may function as the high speed test stand may also be inserted into a prototype line and products including the newly developed product feature may be assembled at high speeds without having to construct or reconstruct a complete prototype line. Further, the standalone feature section(s) may first be utilized as a preliminary machine production unit that may manufacture the feature section being upgraded and/or the entire product incorporating the feature section in order to determine product and process feasibility, then as a high speed test stand and finally inserted into a high speed prototype line. Also, once the product feature upgrade has been successfully produced on a high speed prototype line, the feature section(s), or substantially similar feature section (s), may be inserted into one or more production lines. Even further, where multiple production lines are designed in accordance with the present invention, product upgrades may be easily rolled out over multiple production lines because substantially similar or identical feature sections that have been tested on a pilot line or another production line may be easily inserted into multiple production lines after the testing and debugging of the feature sections have been completed on other lines. Thus, the down time of each production line may be drastically reduced.

Exemplary Line

Figure 33:
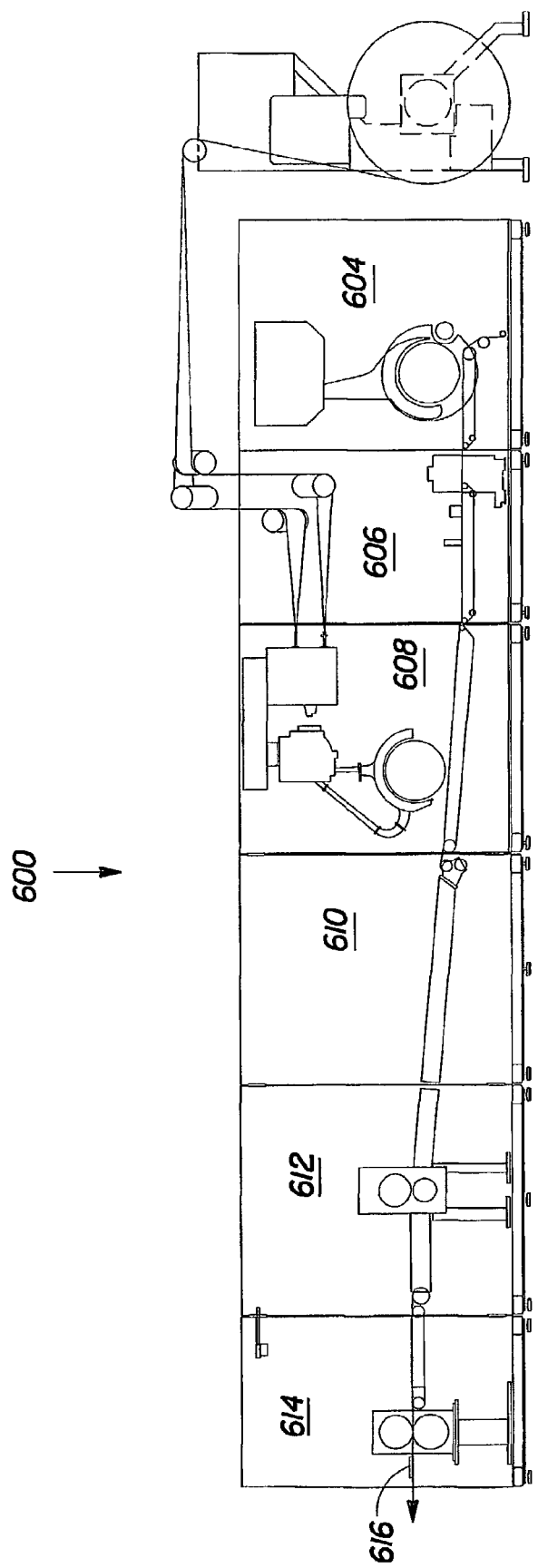
FIG. 33 is a simplified front view from the operator side of a modular absorbent core making operation which could be used for manufacturing absorbent disposable products.

An exemplary modular diaper line for making the diaper 500 shown in FIG. 30 is illustrated schematically in FIGS. 33, 34 and 36. The line comprises fifteen modules and includes an absorbent core making feature section 600 shown in FIG. 33 and a converting operation 602 shown in FIGS. 34 and 36. The absorbent core making feature section 600 comprises six modules: a patch module 604; a tissue module 606; a dry lap module 608; a core folding module 610; a core calendar module 612; and a core cutting module 614. The individual core pads 616 are fed into converting operation 602. The converting operation 602 comprises nine modules as shown in FIGS. 34 and 36: a cuff module 620; a chassis combining in-feed module 622; a chassis combining module 624; a side panel module 626; a landing zone module 60; a fastening tape module 630; a side notch module 632; a folding module 634; and a final forming module 636. The nine modules of converting operation 602 further comprise 5 feature sections and a functional operation.

Figure 38:
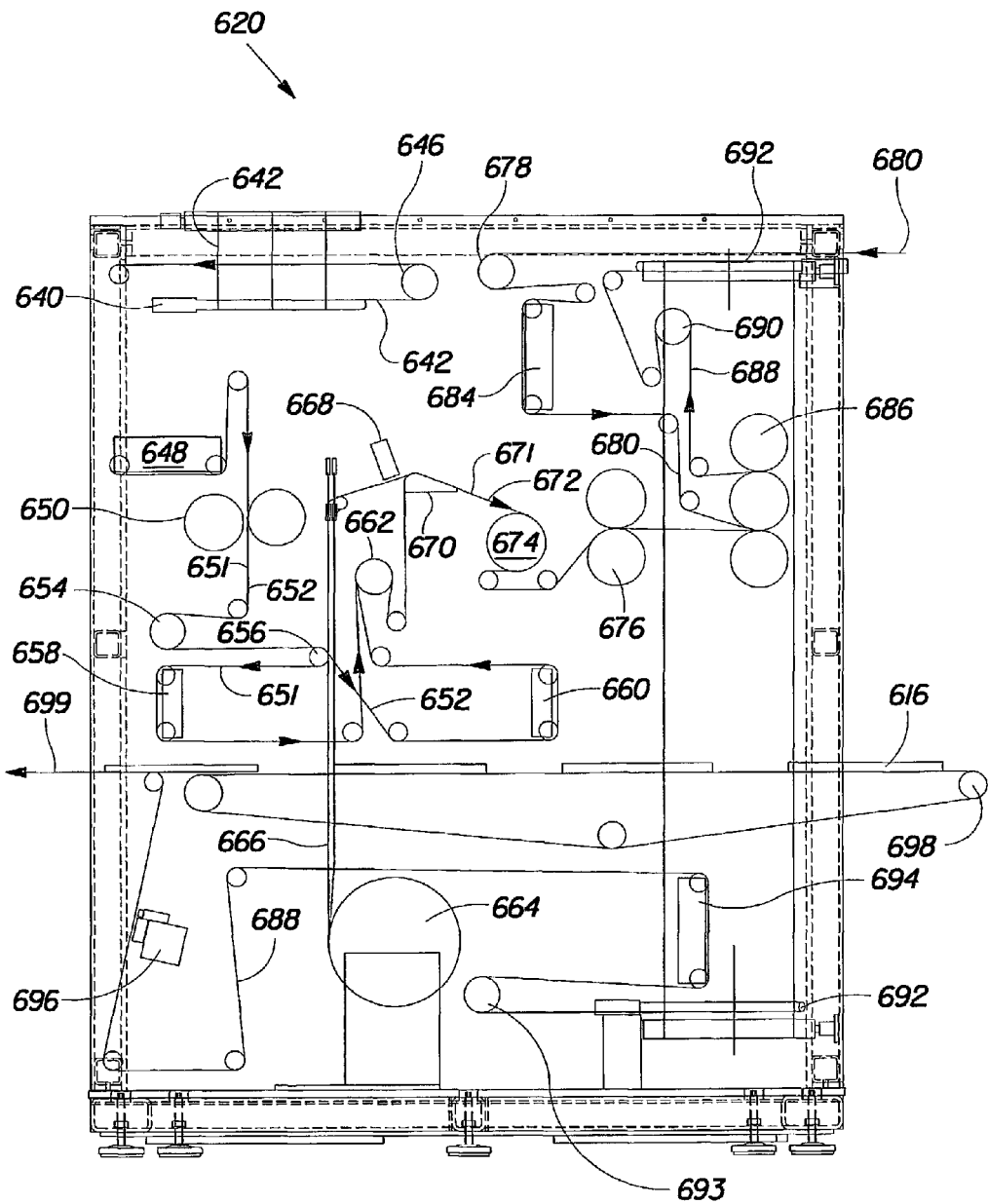
FIG. 38 is a simplified front view from the operator side of the cuff module shown in FIGS. 34–37.

As shown in FIGS. 34, 36 and 38, the cuff feature section A includes cuff module 620. The cuff module 620 comprises a turning bar 640 for turning an cuff material 642 supplied from a reel 644 located on the side of the converter 602 as shown in FIG. 36; an omega roll 646 for metering the cuff material 642; a tracking device 648 for steering the cuff material 642; a slitter 650 for slitting the cuff material 642 into two webs 651 and 652; an omega roll 654 for metering the slit webs 651 and 652; an idler roll 656 for separating the slit cuff material into two webs 651 and 652 ; tracking devices 658 and 660 for steering the slit webs 651 and 652; an omega roll 662 for metering the slit webs 651 and 652; a reel 664 for supplying elastic strings 666; an adhesive applicator 668 for intermittently applying adhesive onto the elastic strings 666; a folding device 670 for applying the elastic strings 666 onto the slit cuff webs 651 and 652, and forming two cuffs 671 and 672; a chill roll 674 for chilling the adhesive; a two-roll cuff forming device 676; an omega roll 678 for metering a topsheet web 680 supplied from a reel 682 located on the side of the converting line as shown in FIG. 36; a tracking device 684 for the topsheet web 680; a 3-roll bond device 686 for bonding the top cuffs 671 and 672 to the top sheet web 680 producing a topsheet/cuff combined web 688; an omega roll 690 for metering the topsheet/cuff combined web 688; upper and lower turning rolls 692 for directing the topsheet/cuff combined web 688; an omega roll 693 for metering the combined material 688; a tracking device 694 for steering the topsheet/cuff combined web 688; an adhesive applicator 696 for applying adhesive onto the topsheet web 680; a pad spacing conveyor 698 for creating a specified space between individual absorbent core pads 616 and transporting the core pads 616 onto the top sheet web 680 of the combined material 688 and resulting in a combined material 699.

Figure 39:
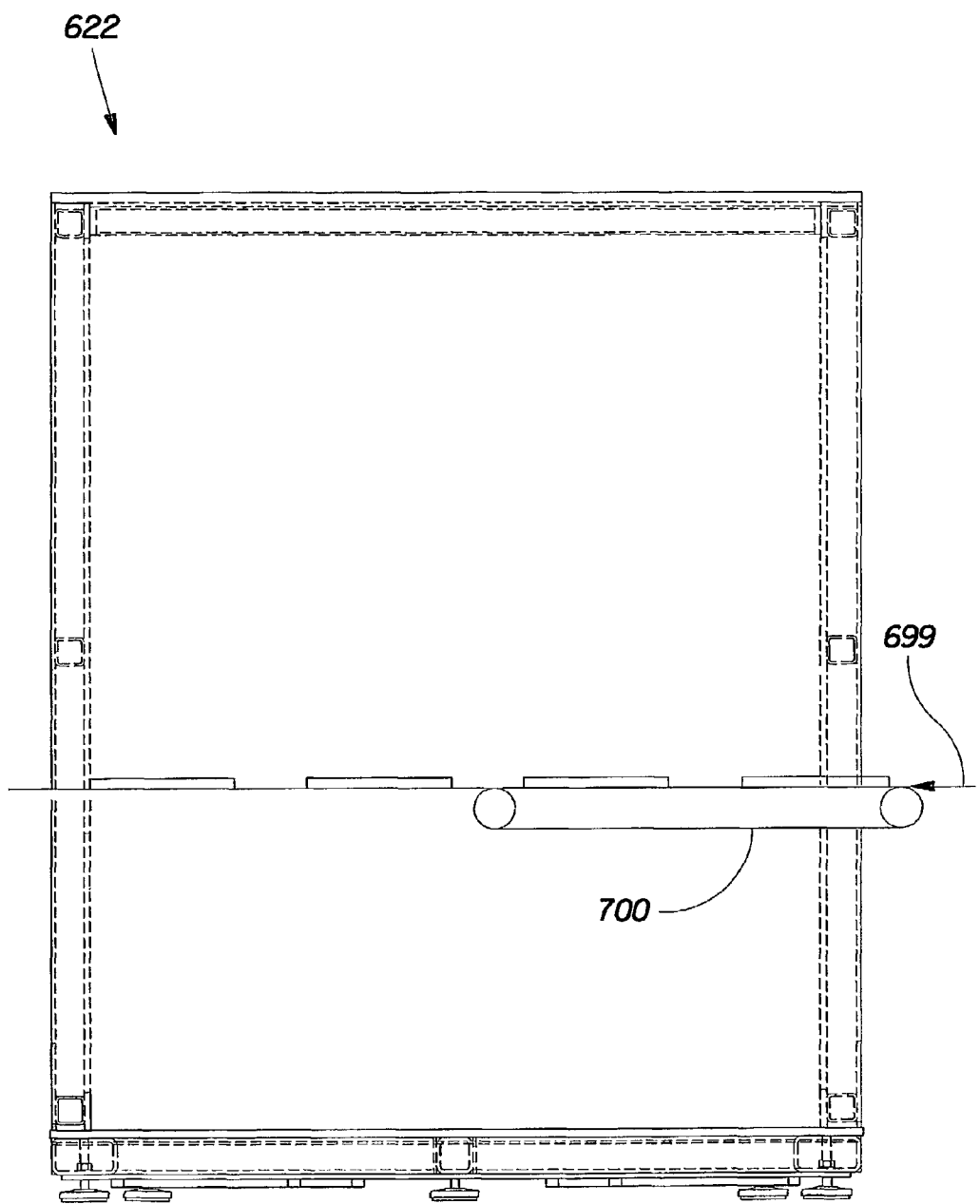
FIG. 39 is a simplified front view from the operator side of the chassis combining in-feed module shown in FIGS. 34–37.
Figure 40:
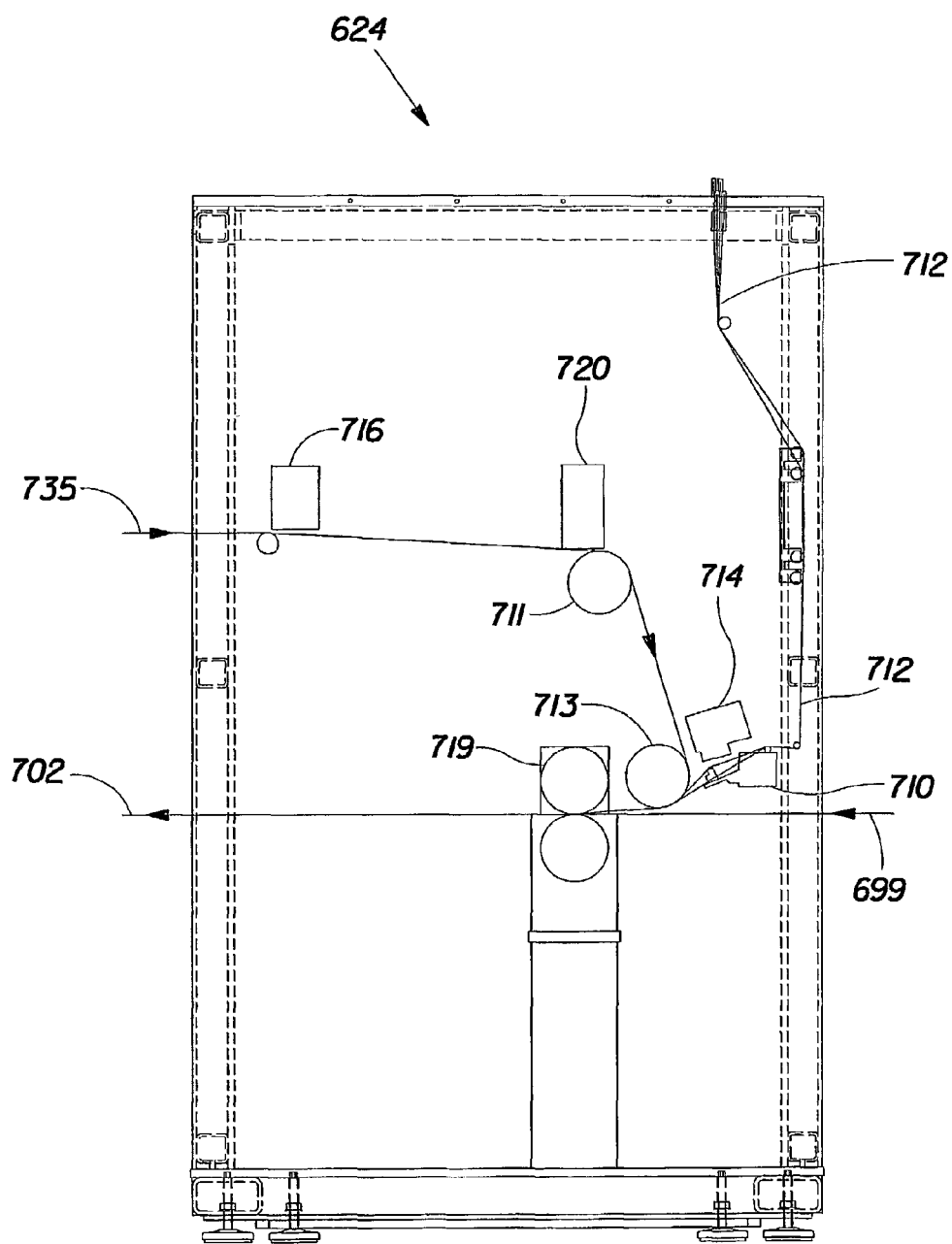
FIG. 40 is a simplified front view from the operator side of the chassis combining module shown in FIGS. 34–37.

The chassis combining in-feed module 622 shown in FIGS. 34, 36 and 39 and the chassis combining module 624 shown in FIGS. 34, 36 and 40 together comprise the chassis combining functional operation B. The chassis combining in-feed module 622 comprises a vacuum conveyor 700 for transporting the combined material 699 from the cuff module 620 comprising the topsheet/cuff web 688 with spaced core pads 616. A suction force created by the vacuum conveyor 700 affects the adhesive bond between the topsheet web 680 and core pads 616.

The chassis combining module 624 comprises a diverter 710 for diverting outer cuff elastics 712 supplied from a box 713 as shown in FIG. 34; an adhesive applicator 714 for applying adhesive onto the outer cuff elastics 712; an adhesive applicator 716 for applying adhesive onto a combined material 735 for bonding the combined material 735 to the core pads 616 located on the web 699 coming from the chassis combining in-feed module 622; and an adhesive applicator 720 for applying an adhesive onto the combined material 735 for bonding the material 735 to the topsheet web 680 of the material 699 and resulting in a combined material 702.

Figure 41:
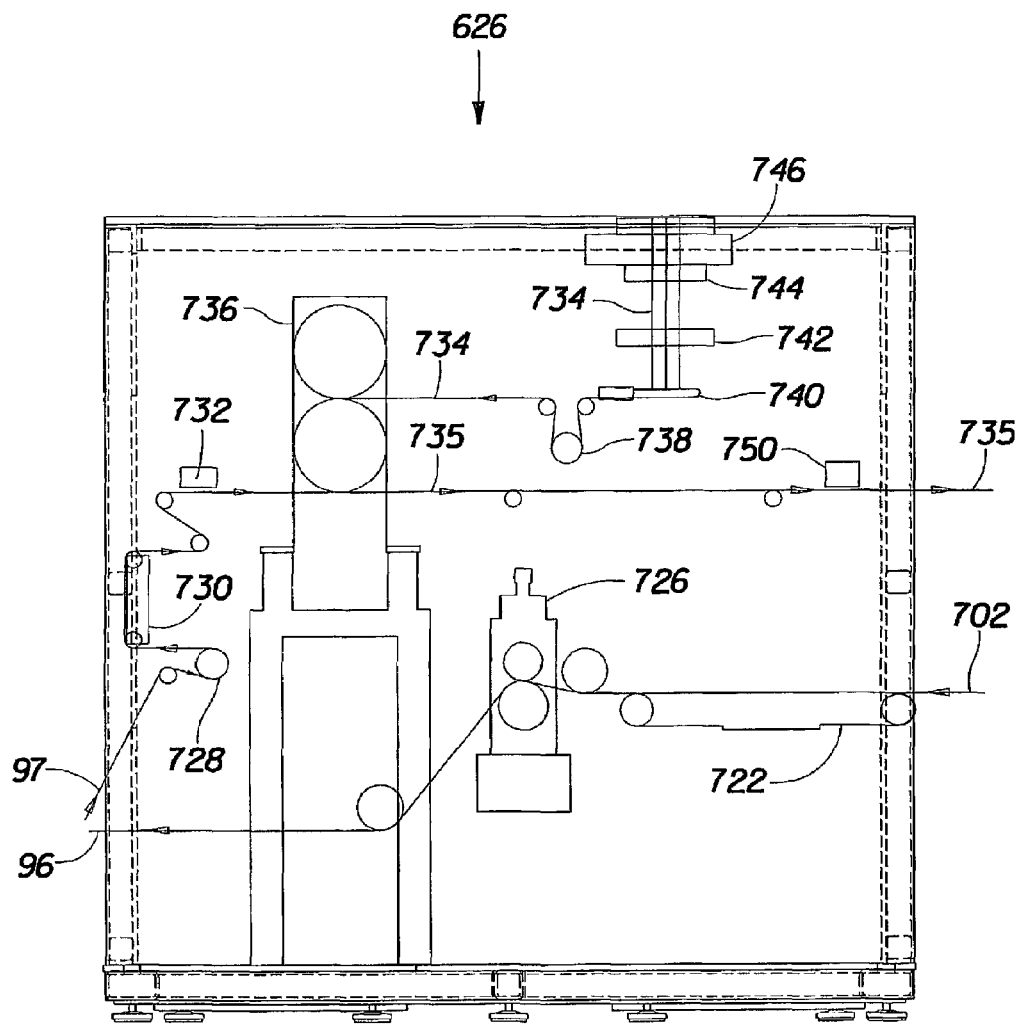
FIG. 41 is a simplified front view from the operator side of the side panel module shown in FIGS. 34 and 36.

The side panel feature section C includes the side panel module 626 shown in FIGS. 34, 36 and 41. The side panel module 626 comprises a vacuum conveyor 722 for transporting the combined web 702 from the chassis combining module 624; an activation device 726 for activating the side panels 510 of diaper 500 shown in FIG. 30 on the web 702 and resulting in a material 96; an omega roll 728 for metering a material 97 coming from the landing zone module 60, which is shown in FIG. 7; a tracking device 730 for steering the material 97; an adhesive applicator 732 for applying adhesive onto the material 97 for bonding the material 97 to a side panel material 734 and resulting in a combined material 735; a cut and slip device 736 for cutting and applying the side panel material 734 onto the material 97, an omega roll 738 for feeding the side panel material 734 to the cut and slip device 736; a turning bar 740 for the side panel material 734; a slitting device 742 for the side panel material 734; a tracking device 744 for steering the side panel material 734; and an omega roll 746 for feeding the side panel material 734. The side panel material 734 may be fed from a reel 748 such as shown in FIG. 36.

As shown in FIGS. 34 and 36, the landing zone feature section D includes the landing zone module 60. The landing zone module 60 is shown in detail in FIGS. 7–10 and is described above.

Figure 42:
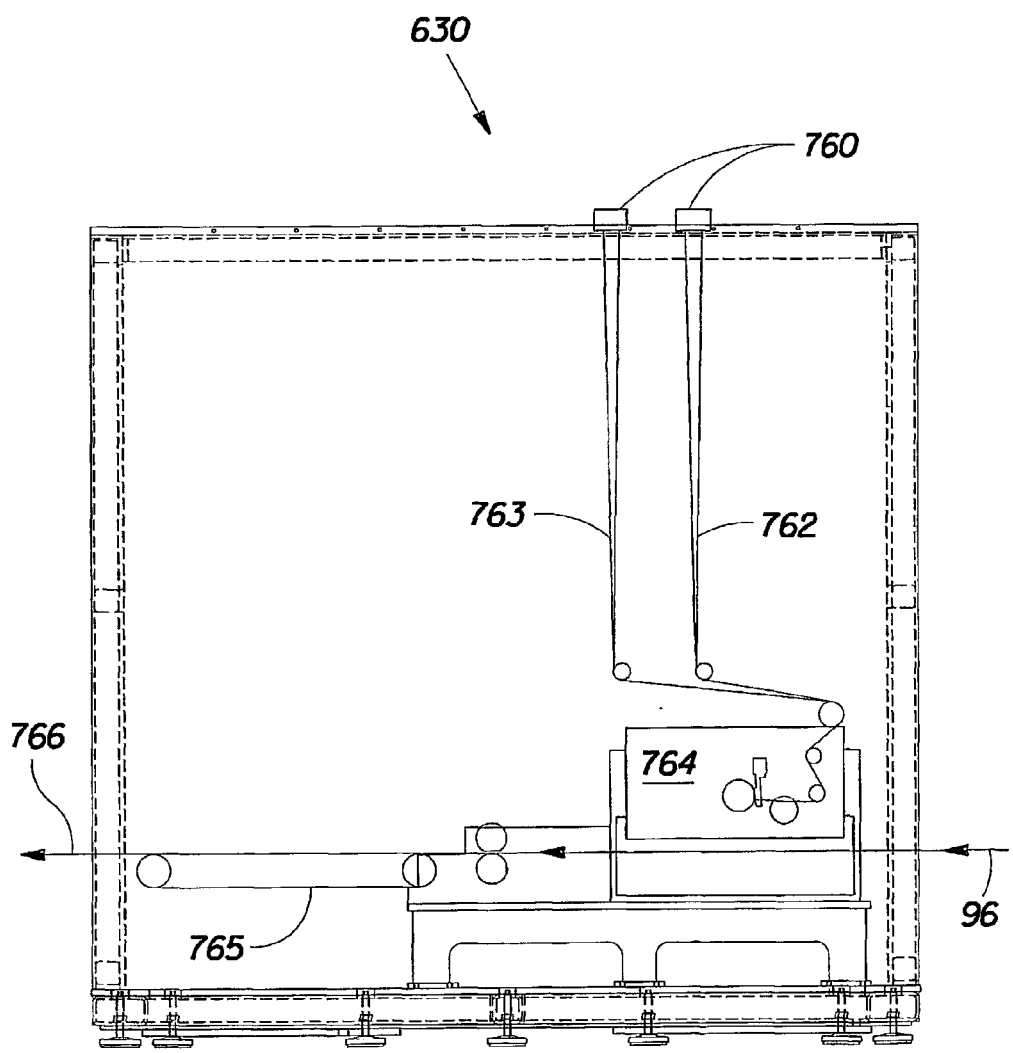
FIG. 42 is a simplified front view from the operator side of the fastening tape module shown in FIGS. 34 and 36.
Figure 43:
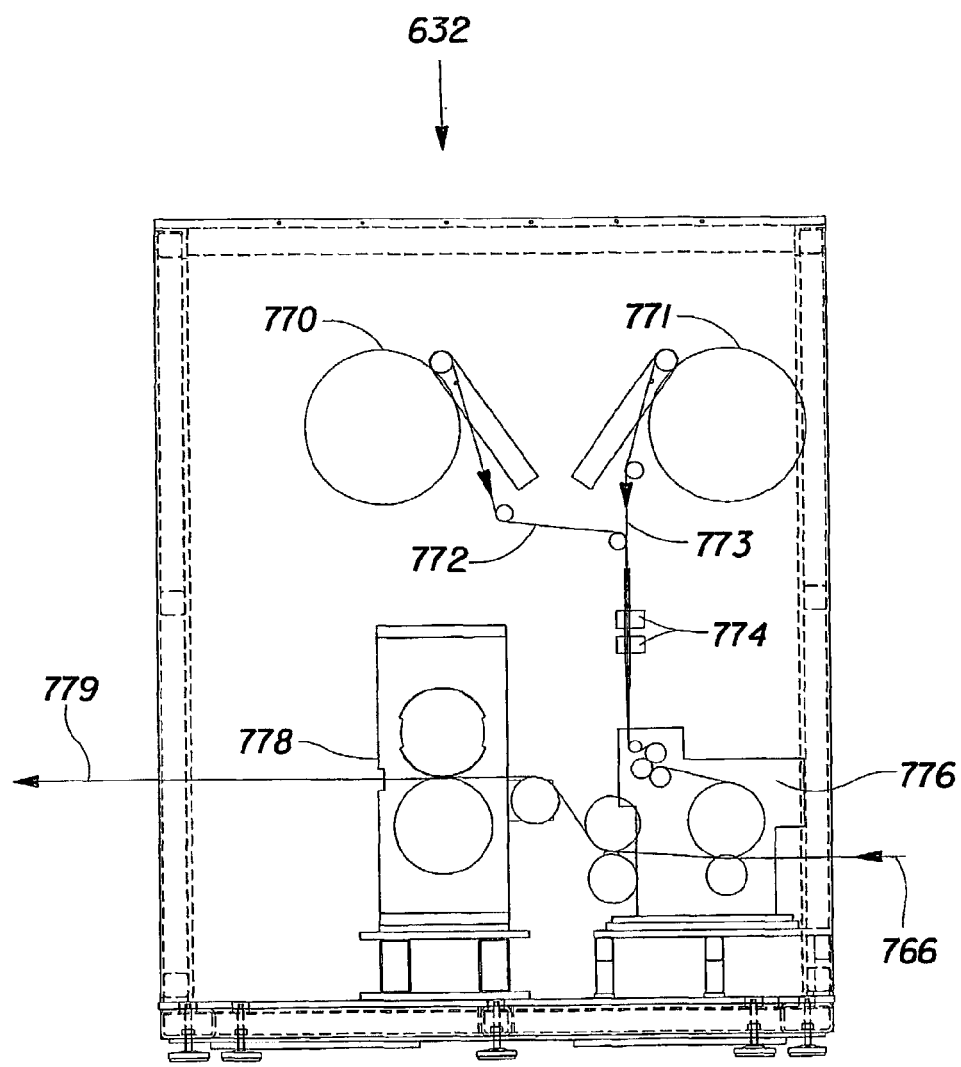
FIG. 43 is a simplified front view from the operator side of the side notch module shown in FIGS. 34 and 36.

The fastening feature section E includes the primary fastening module 630 shown in FIGS. 34, 36 and 42 and the secondary fastening module 632 shown in FIGS. 34, 36 and 43. The primary fastening module 630 comprises a fastening tape delivery device 760 for delivering two webs of primary fastening tapes 762 and 763; a tape applicator 764 for applying the two webs of primary fastening tapes 762 and 763 onto the material 96 and resulting in a material 766; and a vacuum conveyor 765 for transporting the material 766. The secondary fastening module 632 comprises two reels 770 and 771 for supplying two webs of a secondary fastening material 772 and 773; pull rolls 774 for metering the two webs of the secondary fastening material 772 and 773; and an applicator 776 for applying the secondary fastening materials 772 and 773 onto the web 766 and resulting in a web 779. The secondary fastening module 632 may also house a side notch device 778 for making a side notch in the crotch area 520 of the diaper 500 shown in FIG. 30. The side notch device 778 does not add any new material to the web 779, but rather removes a portion of the web to create the side notches of diaper 500. Thus, the side notch operational unit does not form a feature section of the manufacturing line. Although the side notch device 778 may be housed in a separate module from the fastening feature section, as shown in the embodiment shown in FIGS. 34 and 43, the side notch device 778 may be housed in a module of a feature section that includes space and may be commonly controlled along with the feature section itself.

Figure 44:
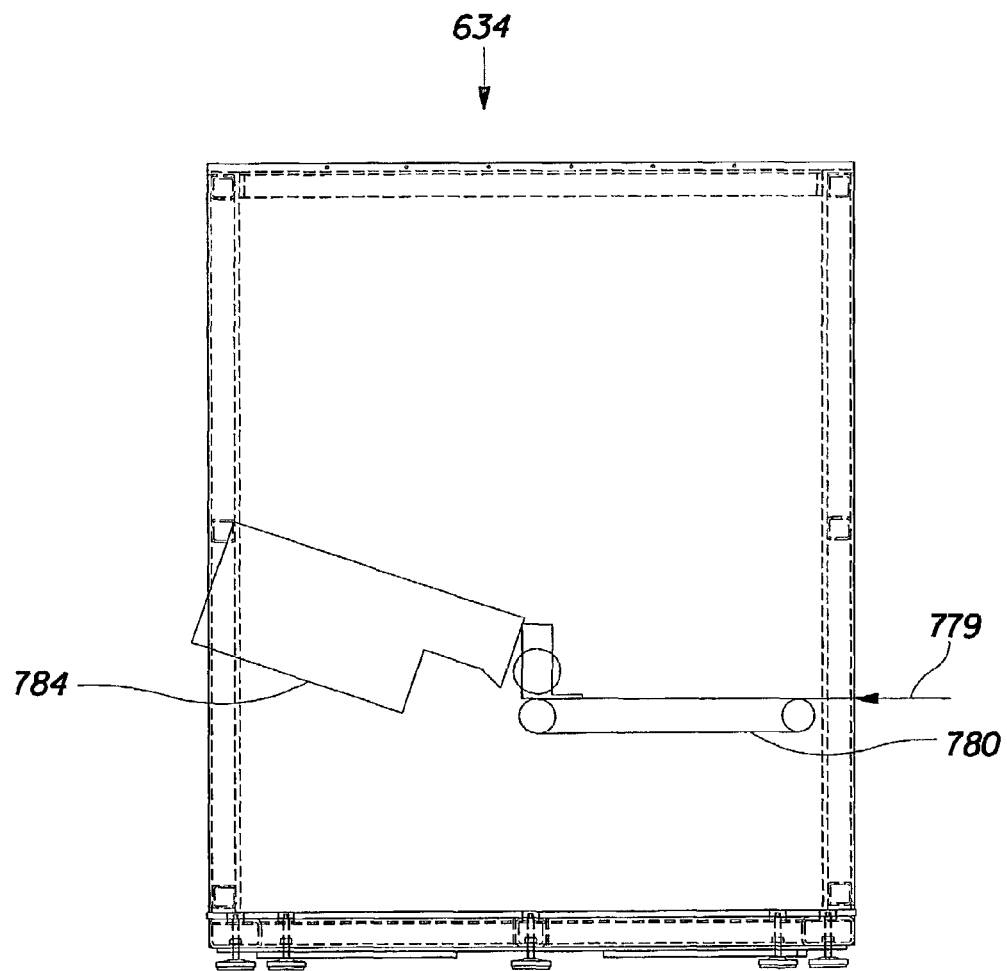
FIG. 44 is a simplified front view from the operator side of the E-fold module shown in FIGS. 34–37.
Figure 45:
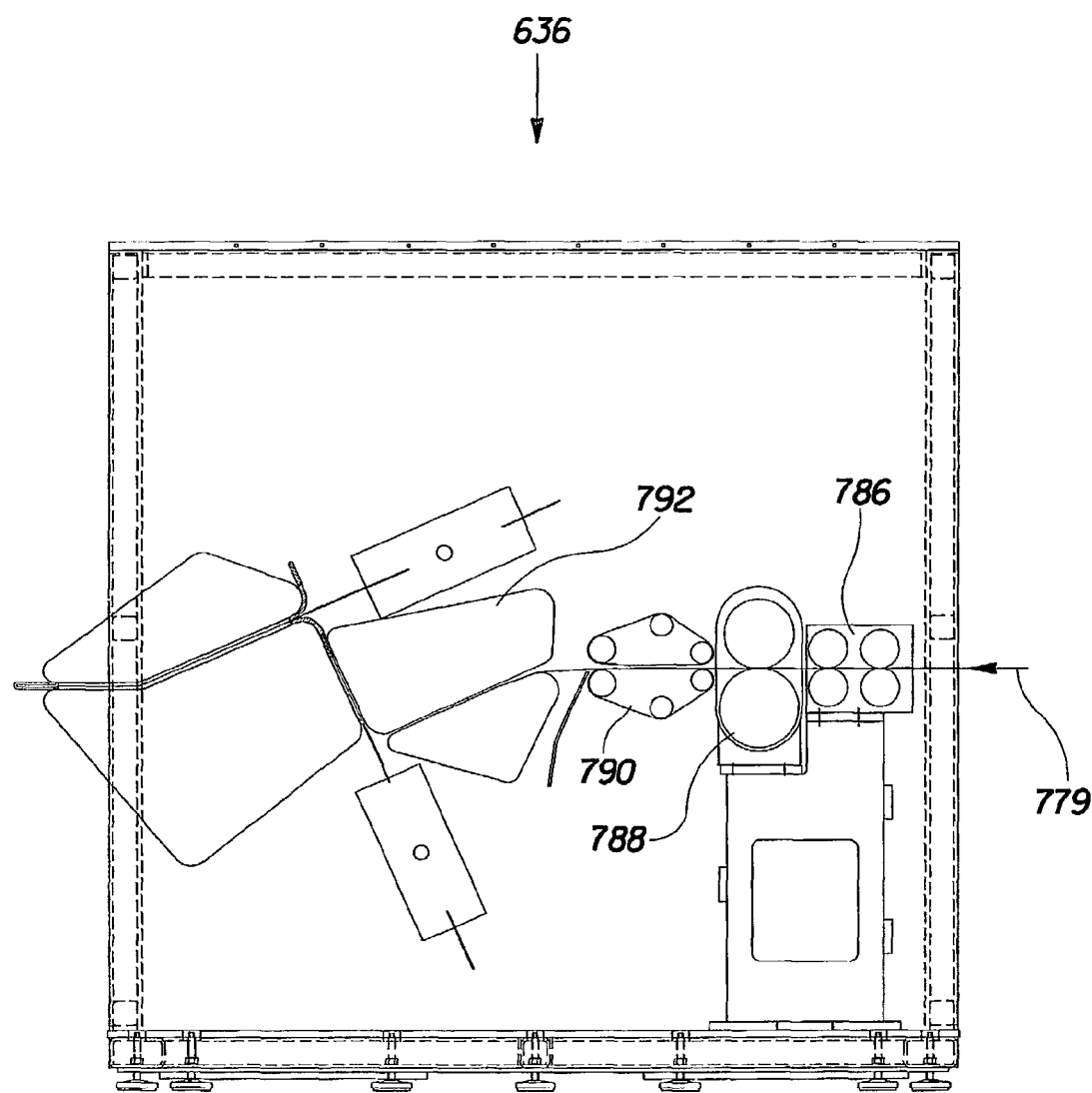
FIG. 45 is a simplified front view from the operator side of the final forming module shown in FIGS. 33 34–37.
Figure 46:
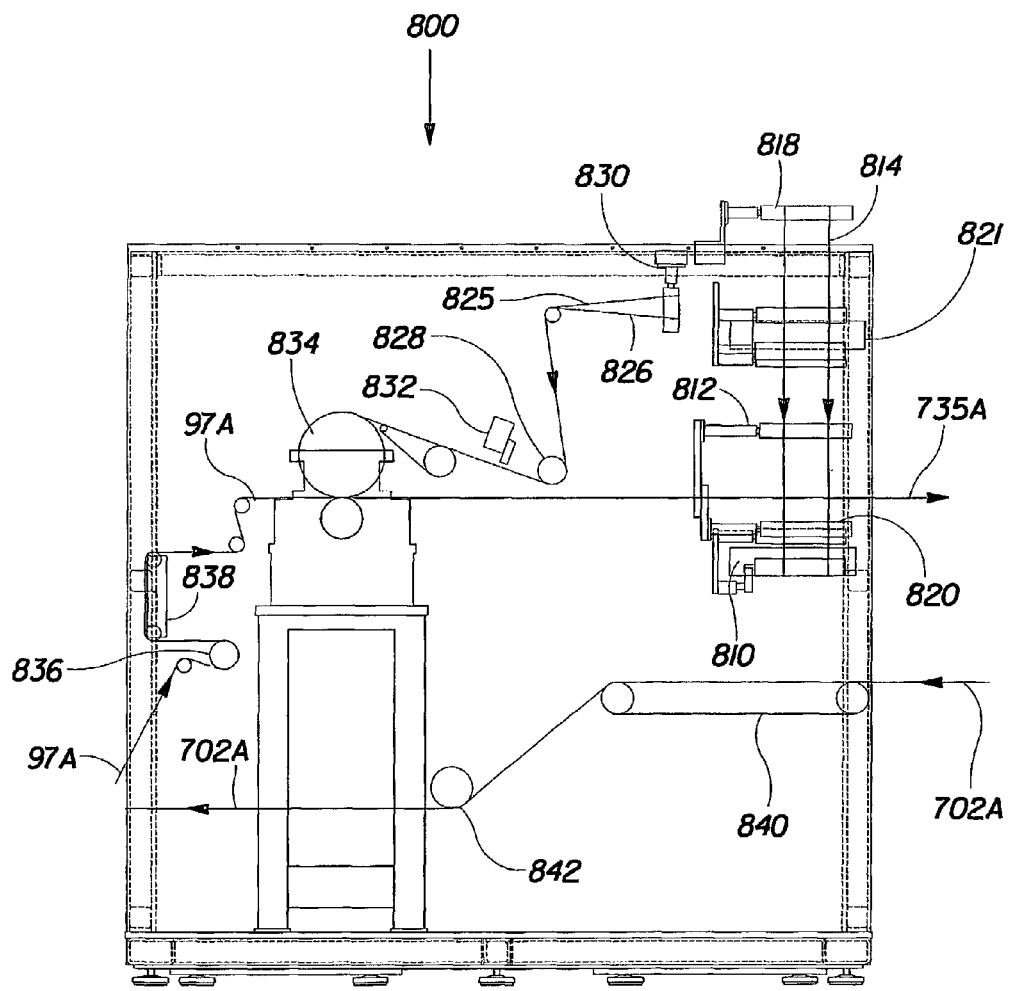
FIG. 46 is a simplified front view from the operator side of the front ear module shown in FIGS. 35 and 37.
Figure 47:
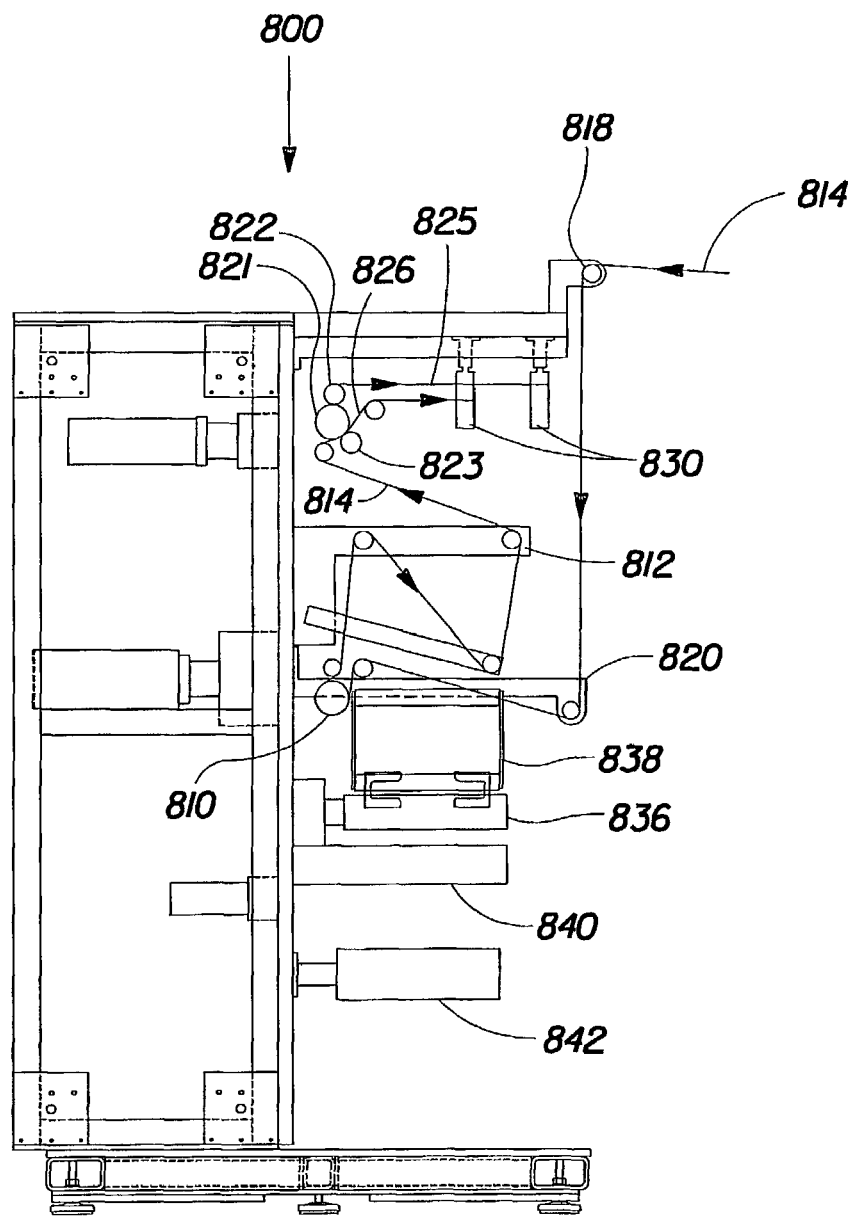
FIG. 47 is a simplified side view of the front ear module shown in FIG. 46.
Figure 49:
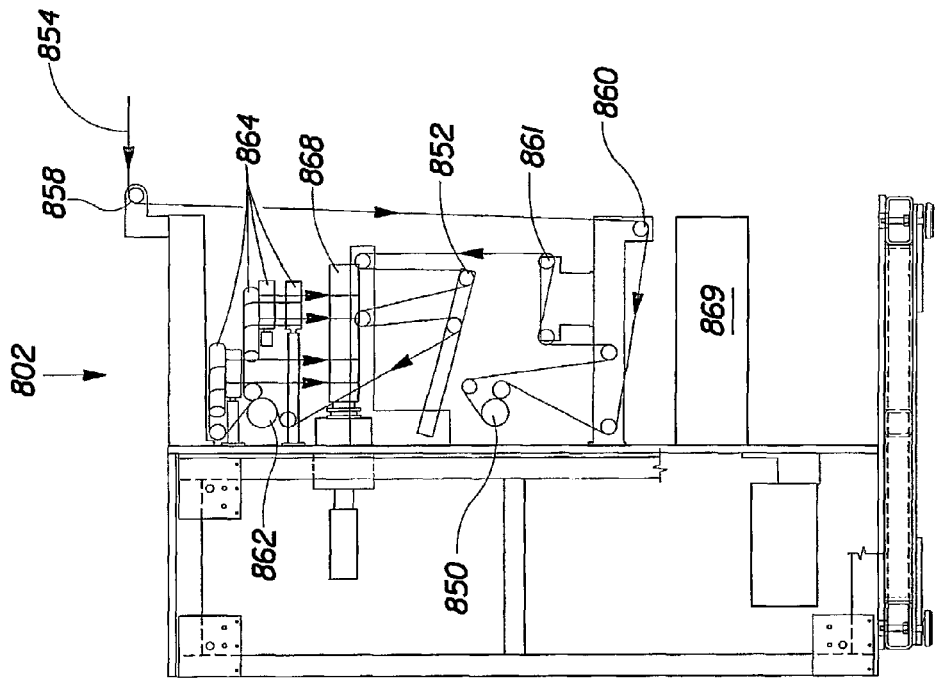
FIG. 49 is a simplified side view of the back ear in-feed module shown in FIG. 48.
Figure 48:
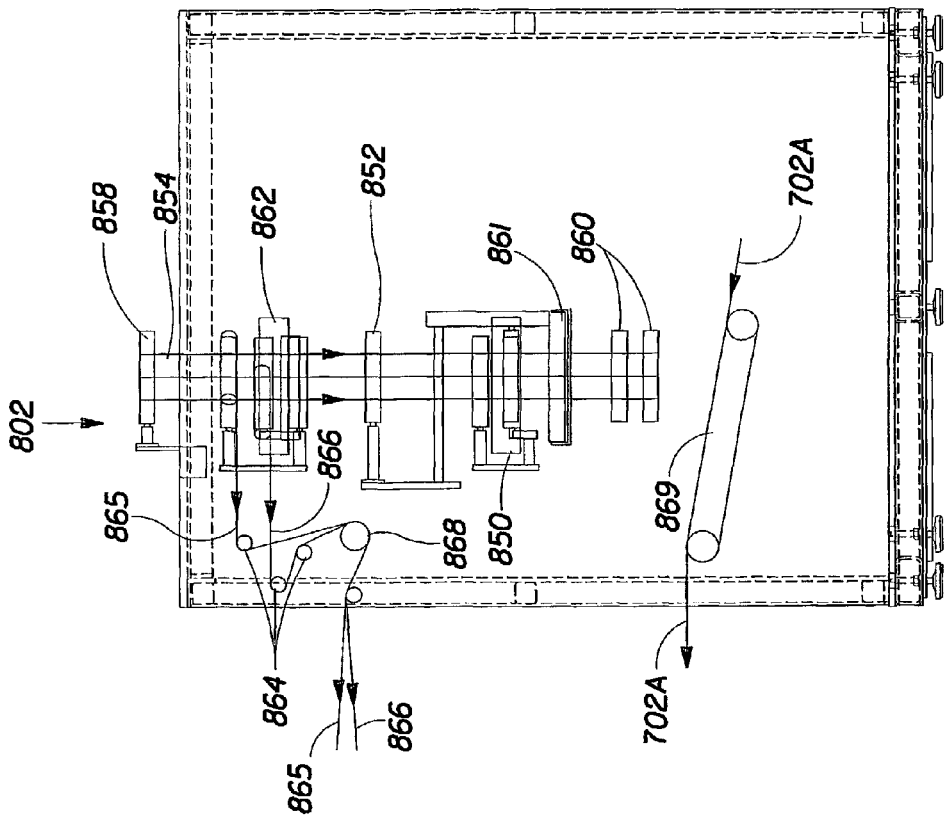
FIG. 48 is a simplified front view from the operator side of the back ear in-feed module shown in FIGS. 35 and 37.

The folding module 634 shown in FIGS. 34, 36 and 44 and the final forming module 636 shown in FIGS. 34, 36 and 45 together comprise the fold and form feature section F. The folding module 634 comprises a vacuum conveyor 780 for transporting the web 779; and a folding device 784 for folding the web 779. The final forming module 636 comprises pull rolls 786 for metering the web 779; a final knife 788 for cutting the web 779 into individual diapers; a discharge conveyor 790 for discharging defective diapers; and a final folding device 792 for bringing the diaper into a final folding shape.

In order to produce another type of diaper, for example the diaper 550 shown in FIG. 31, the converting portion 602 shown in FIGS. 34 and 36 may be changed by removing three modules 626, 630 and 632 and bringing new modules 800, 802 and 804 shown in FIGS. 35 and 37. Specifically, the side panel module 626 may be replaced by a front ear module 800; and both the tape module 630 and the side notch module 632 may be replaced by a back ear in-feed module 802 and a back ear application module 804, respectively. A method for changing modules on a production line is described below.

The front ear feature section H includes the front ear module 800 shown in FIGS. 35, 37, 46 and 47. The front ear module 800 comprises an omega roll 810 and a dancer 812 in combination for metering a front ear material 814 by pulling it from a supply box 816, which is located on the side of the converter 796 as shown in FIG. 37, and through two idler rolls 818; a tracking device 820 for steering the front ear material 814; an omega roll 821 and idler rolls 822 and 823 for splitting the front ear material 814 into two separate front ear webs 825 and 826; an omega roll 828 for metering and pulling the two separate front ear webs 825 and 86 through idler rolls 830; an adhesive applicator 832 for applying an adhesive onto the two separate front ear webs 825 and 826; a cut and slip unit 834 for cutting the two webs 825 and 86 into separate front ears 552, such as shown in FIG. 31, and applying the front ears 552 onto the combined material 97A; an omega roll 836 for metering the material 97A; a tracking device 838 for steering the material 97A into the cut and slip unit 834; and a vacuum conveyor 840 and an idler roll 842 for transporting a combined web 702A from the chassis combining module 624 to the landing zone module 628.

Figure 50:
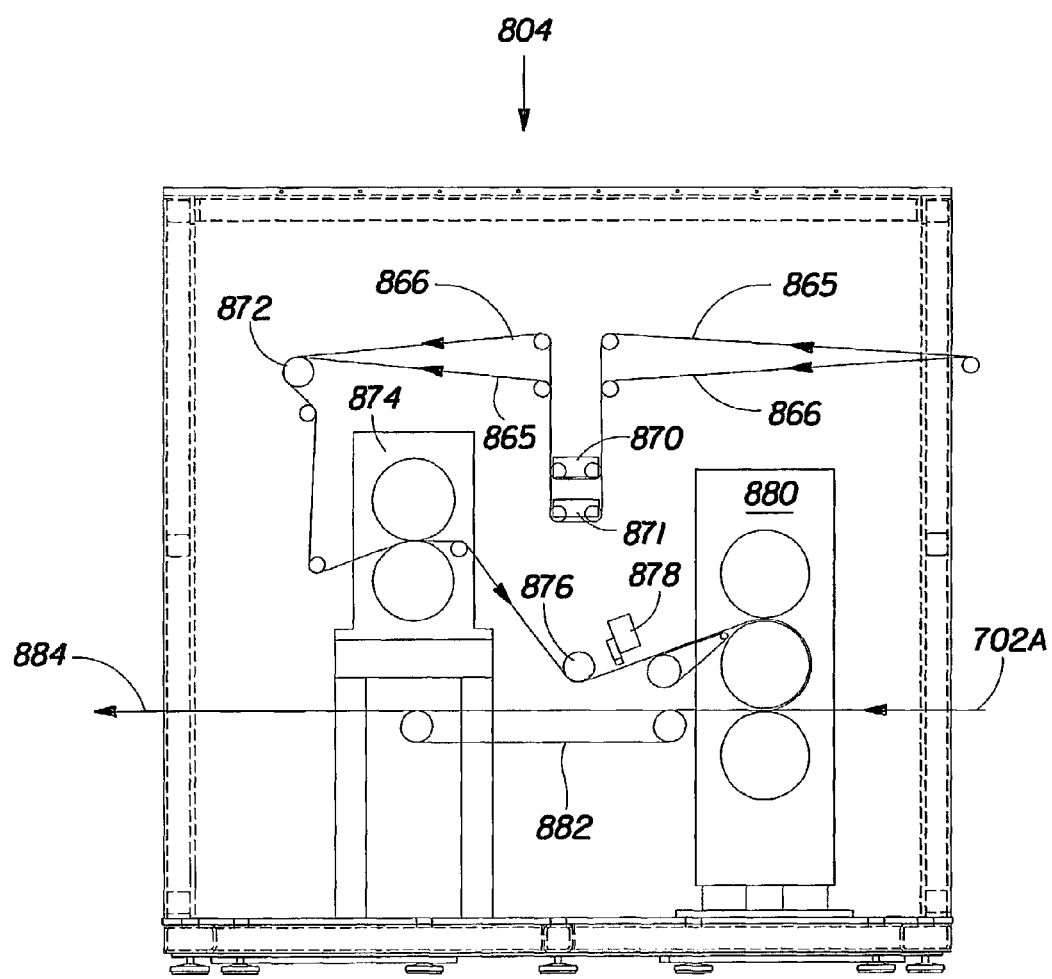
FIG. 50 is a simplified front view from the operator side of the back ear application module shown in FIGS. 35 and 37.

The back ear in-feed module 802 shown in FIGS. 35, 37, 48 and 49 and the back ear application module 804 shown in FIGS. 35, 37 and 50 together comprise the back ear feature section I. The back ear in-feed module 802 comprises an omega roll 850 and a dancer 852 in combination for metering a back ear material 854, which includes the fastening tapes 516 shown in FIG. 31, by pulling the back ear material 854 from a supply box 856, located on the side of the converter 796 as shown in FIG. 37 and through an idler roll 858; a tracking device 860 for steering the back ear material 854; a second tracking device 861 for steering the back ear material 854; an omega roll 862 for metering the back ear material 854; rollers 864 for splitting the back ear material 854 into two separate webs 865 and 866; an omega roll 868 for metering the two separate webs 865 and 866 to a back ear application module 864; and a conveyor 869 for transporting the combined web 702A from the front ear module 800 through the landing zone module 60 to the back ear application module 804.

The back ear application module 804 comprises two tracking devices 870 and 871 for steering the two separate back ear webs 865 and 866; an omega roll 872 for metering the two separate back ear webs 865 and 866; a cutting device 874 for trimming the two back ear webs 865 and 866; an omega roll 876 for metering the two back ear webs 865 and 866; an adhesive applicator 878 for applying an adhesive onto the two back ear webs 865 and 866; a cut and slip device 880 for cutting and applying the back ears 865 and 866 onto the combined web 702A coming from the back ear in-feed module 802; and a conveyor 882 for transporting a material 884 including attached back ears 554 as shown in FIG. 31.

Figure 51:
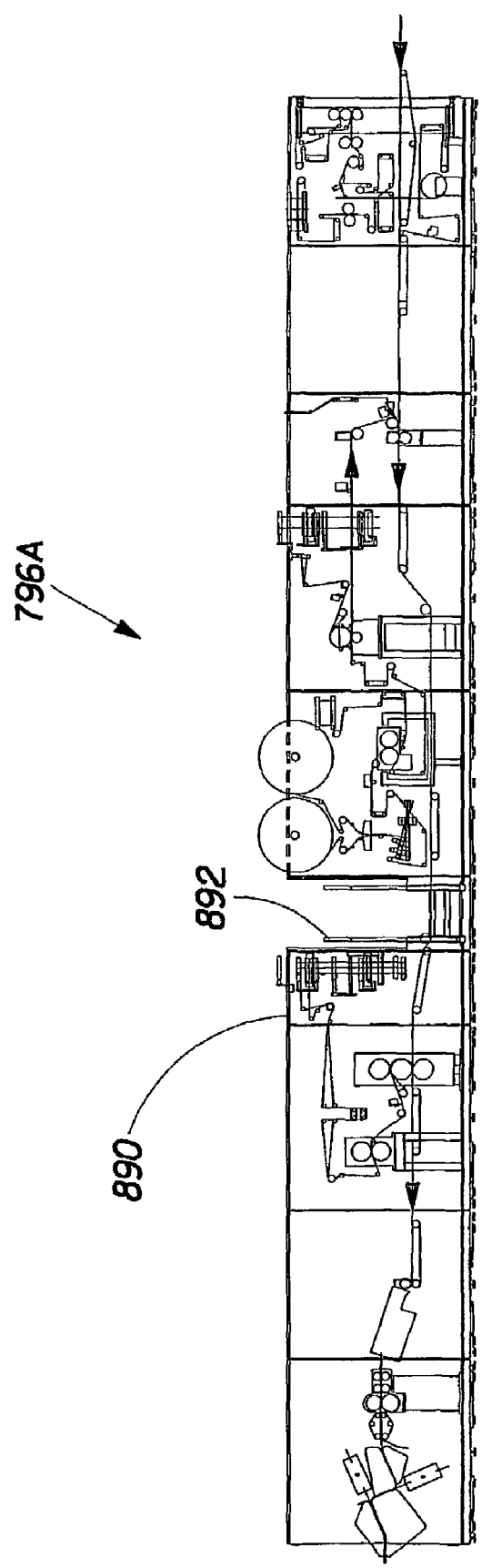
FIG. 51 is a simplified front view from the operator side of a modular converting operation shown in FIG. 35 including a cross-over module.

In another example shown in FIG. 51, a module can be used as a cross-over module 892 to create a cross-over path between both sides of the converting line 796A. In this example the back ear in-feed module 802 of the converting line 796 shown in FIG. 35 is replaced by another back ear in-feed module 890 and a cross-over module 892.

Exemplary Product Upgrade

An exemplary product upgrade of a manufacturing line such as the one shown in FIGS. 35 and 37 may include changing a multiple-layer back ear 854 of the diaper shown in FIG. 31 so that it is extensible. In this example, the back ear 854 may be made extensible such as described in U.S. Pat. No. 5,151,092 entitled "Absorbent Article With Dynamic Elastic Waist Feature Having a Predisposed Resilient Flexural Hinge" issued to Kenneth B. Buell et al. on Sep. 29, 1992, and U.S. Pat. No. 5,518,801 entitled "Web Materials Exhibiting Elastic-Like Behavior" issued to Charles W. Chappell et al. on May 21, 1996, each of which is incorporated by reference. In the manufacturing line shown in FIGS. 35 and 37, for example, the back ear in-feed module 802 or the back ear applicator module 804, which together form the back ear feature section I, may be modified to include operational units that make the back ear 854 of the diaper 550 extensible. The new back ear feature section may be tested off-line until the back ear feature section is assembling back ears that have an acceptable extensibility and is applying the back ears to a web in a satisfactory manner. Then, the existing back ear in-feed module 802 in the manufacturing line may be replaced by the new back ear in-feed module that provides an extensible back ear web to the back ear application module 804.

Methods Of Line Change

The manufacturing system of this invention may provide flexibility for removing at least one feature section from the manufacturing system and/or adding another feature section to the manufacturing system. For example, if there is a need to change a product design that involves a change in a design of a particular product feature, a feature section of the manufacturing system producing that product feature may be removed from the manufacturing system and another feature section adapted for producing the new product feature may be used to replace the removed feature section. The added feature section may physically fit or not fit in the space vacated by the removed feature. If the added feature section physically fits into the space, then no change in the position of adjacent feature section(s) may be necessary. However, if the added feature section physically does not fit into the space, then a change in position of adjacent feature section(s) may be necessary. Further, if there is a need to add a new product feature to a product, a new feature section may be added to the manufacturing system. Adding a new feature may or may not involve a change in position of adjacent feature section(s).

Referring to FIGS. 1–6, 11–12, 23A, 23B and 60, removing a module from a manufacturing line may involve all or some of the following steps (not necessarily in the order listed below):

1) Lock out the motion bus 252, the auxiliary bus 253, and the safety lockout switch 360.
2) Disconnect the power and feedback cables 342 such as via the quick disconnects 344.
3) Disconnect the logic control network cable 348 from the electrical main junction box 346 such as via the quick disconnect 350.
4) Disconnect the house cleaning vacuum such as via quick disconnect 322.
5) Disconnect the low vacuum such as via quick disconnect 318.
6) Disconnect the high vacuum such as via quick disconnect 320.
7) Disconnect the glycol supply and return such as via quick disconnects 326.
8) Disconnect the compressed air supply such as via quick disconnect 324.
9) Disconnect and remove the adhesive supply hose(s) 388.
10) Disconnect and remove the safety lockout switch cable 362 from the power and distribution center panel 328 such as via a quick disconnect 364.
11) Set up lifting mechanism manifold 130 and thread air lines 132 to the module.
12) Insert lifting mechanisms 30 into regions 22 under the module.
13) Remove bolts and pins 38, spacers 36, and wedges 32 and 34 from the module.
14) Measure and record the height of feet 26 on the module from the floor to the bottom of the horizontal plate 16.
15) Secure the module. For example, a person may be placed on the operator side and on the drive side of the module.
16) Activate the lifting mechanism and remove the module from the line. For example, the lifting mechanisms 30 may be inflated, and the module may be slowly pushed out of the line.
17) Move the module out of the way and lower the module. The lifting mechanism 30, for example, may be slowly deflated.

Referring to FIGS. 1–6, 11–12, 23A, 23B and 60, inserting a module into a manufacturing line may, for example, involve all or some of the following steps (not necessarily in the order listed below):

1) Lock out the module's motion bus 252, the auxiliary bus 253, and the safety lockout switch 360.
2) Adjust the height of the feet of the module being inserted to the height of the feet 26 of the replaced module.
3) Insert lifting mechanisms 30 into regions 22 under the module.
4) Secure the module. For example, a person may be placed on the operator side and on the drive side of the module.
5) Activate the lifting mechanism. For example, the lifting mechanisms 30 may be inflated.
6) Guide the module into an aligned position on the manufacturing line.
7) Lower the lifting mechanism. For example, the lifting mechanisms 30 may be deflated and removed.
8) Adjust the feet 26 of the module to ensure that the vertical plates 10 and 12 of the module being inserted and of the adjacent module(s) are parallel and that the modules are at the same elevation.
9) Insert spacers 36 and wedges 32 and 34 and secure the module with bolts and pins 38.
10) Connect the house cleaning vacuum such as via quick disconnect 322.
11) Connect the low vacuum such as via quick disconnect 318.
12) Connect the high vacuum such as via quick disconnect 320.
13) Connect the glycol supply and return such as via quick disconnects 326.

14) Connect the compressed air supply such as via quick disconnect 324.
15) Connect the adhesive supply hose(s) 388.
16) Connect the safety lockout switch cable 362 to the power distribution center 328 such as via a quick disconnect 364.
17) Connect the logic control network cable 348 to the electrical main junction box 346 such as via a quick disconnect 350.
18) Connect the power and feedback cable 342 such as via the quick disconnects 344.
19) Unlock the motion bus 252, the auxiliary bus 253, and the safety lockout switch 360.
20) Load module software into the motion controller 334 and the logic controller 340.
21) Push the start button on the operator interface 354 or the main operator interface 630.

This may automatically home the drives.

Standard control panels such as standard control panels 370 shown in FIG. 56 may be reconfigured to perform as a control panel for a different feature section, or may be added to, replaced in or removed from a flexible manufacturing system of the present invention. If a feature section is replaced by another feature section, often the standard control panels for the feature section that is being removed may be reconfigured as control panels for the new feature section. In this case, software and/or hardware in the standard control panels may be replaced or reconfigured in order to control the operation of the new feature section. Alternatively, if a new feature section is inserted into the flexible manufacturing system and no spares already exist along the line that may be configured as control panels for that feature section, one or more new standard control panels such as a standard main control panel 370N, a standard auxiliary panel 374N and/or a standard adhesive panel 960N may be installed to support the new feature section such as shown in FIGS. 56 and 58. New standard control panel(s) may also need to be installed in different locations along the flexible manufacturing system than the panel(s) being replaced. If it is necessary to remove an existing standard control panel and to install a new standard control panel, all or some of the following steps, for example, may be performed (not necessarily in the order listed below):

1) Lock out the module's motion bus 252, auxiliary bus 253 and safety lockout switch 360.
2) Disconnect the electrical power cable 333 from the motion bus 252 such as via a quick disconnect 337.
3) Disconnect the electrical power cable 341 from the auxiliary bus 253 such as via a quick disconnect 345.
4) Disconnect the remote local network cable 348 from the electrical main junction box 346 such as via a quick disconnect 350.
5) Disconnect the control motion cable 338 from the motion controller 334 inside the standard control panel 370.
6) Disconnect the logic control network cable 352 from the logic controller 340 inside the standard control panel 370.
7) Disconnect the power and feedback cable 342 such as via the quick disconnect 344.
8) Remove the standard control panel 370.
9) Install a new standard electric panel 370N.
10) Connect the power and feedback cable 342 such as via the quick disconnect 344.
11) Connect the logic control network cable 352 from the logic controller 340 inside the new standard control panel 370N.
12) Connect the control motion cable 338 from the motion controller 334 inside the new standard control panel 370N.
13) Connect the remote local network cable 348 from the electrical main junction box 346 such as via the quick disconnect 350.
14) Connect the electrical power cable 341 from the auxiliary bus 253 such as via the quick disconnect 345.
15) Connect the electrical power cable 333 from the motion bus 252 such as via the quick disconnect 337.
16) Unlock the motion bus 252, the auxiliary bus 253, and the safety lockout switch 360.
17) Load module software into the motion controller 334 and the logic controller 340 of the new standard control panel 370N.
18) Push the start button on the operator interface 354 or the main operator interface 920.

This may automatically home the drives. If an existing standard control panel is to be removed but a new standard control panel is not to be added, steps 1–8 may be sufficient. Alternatively, if a new standard control panel is to be added, but no existing standard control panels are to be removed, steps 9–18 may be sufficient.

When replacing a module with a module that has a different length than the original module or when modules are rearranged and the location of module to module connections are changed, the panel support structure 240 shown in FIGS. 24–29 may require reconfiguration of the panel support structure 240. The reconfiguration may involve changing the location of one or more columns 244, changing the location of the wireway 249, and/or relocating or adding the header support 254 shown in FIG. 23A.

Changing a location of a column may, for example, involve all or some of the following steps (not necessarily in the order listed below):

1) Before removing the column to be removed or replaced, position a new column under the panel support structure 240 in the new location.
2) Align the new column with the correct pre-drilled holes in the beam 264.
3) Place a shim, such as a 25 mm thick shim, under the new column.
4) Bolt the top of the new column to the beam with bolts 255.
5) Drill holes, such as the four holes shown, into the floor.
6) Insert bolts 263, such as adhesive threaded rod anchor bolts, through the base plate 265 and into the four holes in the floor.
7) Grout under the new column and secure nuts 261 onto the base plate 265.
8) Tighten the bolts 255 at the top of the new column.

Once the new column is secured in place, it may be safe to remove the old column causing to allow free movement of the doors of new module. The removal of the old column may, for example, involve all or a portion of the following steps (not necessarily in the order listed below):

1) Remove the grout 268 from under the old column.
2) Cut the four bolts 263 attaching the old column to the floor.
3) Unscrew the bolts 255 at the top of the old column from the beam 264 and remove the old column.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method for configuring a flexible manufacturing system for producing disposable articles in relation to a surface on which the flexible manufacturing system is located, the flexible manufacturing system comprising a plurality of operational units for forming the disposable articles, a central computer for providing a reference signal to synchronize said operational units, an electrical power system for driving said operational units, and a utility system for supplying at least one utility to said operational units, said method comprising the steps of:

1) providing a first feature section, said first feature section comprising at least one first feature module including at least one first feature operational unit, and at least one first feature local controller housed in a first standard control panel for controlling said at least one first feature operational unit, said at least one first feature module being connected to said electrical power system and to said utility system, said at least one first feature module being capable of receiving at least one lifting mechanism;

2) providing a second feature section, said second feature section comprising at least one second feature module including at least one second feature operational unit, and at least one second feature local controller housed in a second standard control panel for controlling said at least one second feature operational unit and a second feature operator interface capable of providing a change in said disposable articles, said at least one second feature module being adjacent and connected to said at least one first feature module, said electrical power system and to said utility system, said at least one second feature module being capable of receiving at least one lifting mechanism;

3) providing a third feature section being capable of being attached to at least one of said first feature section, said third feature section comprising at least one third feature module including at least one third feature operational unit, said at least one third feature module being capable of being connected to said at least one said second feature module, said electrical power system and to said utility system, said at least one third feature module being capable of accepting at least one lifting mechanism;

4) positioning said at least one lifting mechanism under said at least one first feature module on said surface;

5) disconnecting said electric power system and said utility system from said at least one of said first feature module;

6) detaching said at least one first feature module from said at least one second feature module;

7) providing compressed fluid to said at least one lifting mechanism for creating a cushion of compressed fluid between said at least one lifting mechanism and said surface so as to lift said at least one first feature module above said surface;

8) moving said at least one first feature module out of said flexible manufacturing system so as to provide a vacant space;

9) positioning at least one lifting mechanism under said at least one third feature module on said surface;

10) providing compressed fluid to said at least one lifting mechanism for creating a cushion of compressed fluid between said at least one lifting mechanism and said surface so as to lift said at least one third feature module above said surface;

11) moving said at least one third feature module into a position where it can be attached to said flexible manufacturing system;

12) attaching said at least one third feature module to said at least one second feature module; and 13) connecting said at least one third feature module to said electrical power system and said fluid utilities system.

2. The method of claim 1, further comprising the step of:

14) reconfiguring said first standard control panel to operate as a third feature local controller for controlling said at least one third feature operational unit.

3. The method of claim 1, wherein said third feature section further comprises a third feature control panel for driving said at least one third feature operational unit, and the method further comprising the steps of:

15) disconnecting at least one said first feature control panel and second feature control panel from said flexible manufacturing system; and 16) connecting said third feature control panel to said flexible manufacturing system.

4. The method of claim 1 wherein said third feature section includes at least one adhesive applicator, said method further comprising the step of providing an adhesive supply hose for supplying an adhesive to said adhesive applicator.

* * * * *

UNITED STATES PATENT AND TRADEMARK OFFICE
CERTIFICATE OF CORRECTION

PATENT NO.   : 6,990,715 B2
DATED        : January 31, 2006
INVENTOR(S)  : Vincent Bardina Liu et al.

It is certified that error appears in the above-identified patent and that said Letters Patent is hereby corrected as shown below:

Column 9,
Line 13, delete "comer" and insert -- corner --.

Column 13,
Line 50, delete "comers" and insert -- corners --.

Column 19,
Line 31, delete "preprogrammed" and insert -- pre-programmed --.

Column 21,
Line 6, delete "microcomputer," and insert -- micro-computer, --.

Signed and Sealed this

Eleventh Day of April, 2006

JON W. DUDAS
*Director of the United States Patent and Trademark Office*